United States Patent
Finn et al.

(10) Patent No.: US 10,513,567 B2
(45) Date of Patent: Dec. 24, 2019

(54) POLYCATIONS AND METHODS OF MAKING AND USING THEREOF

(71) Applicant: Georgia Tech Research Corporation, Atlanta, GA (US)

(72) Inventors: M. G. Finn, Atlanta, GA (US); Jennifer Marie Beveridge, Atlanta, GA (US); Allison Frances Geoghan, Atlanta, GA (US); Zhishuai Geng, Atlanta, GA (US)

(73) Assignee: Georgia Tech Research Corporation, Atlanta, GA (US)

( * ) Notice: Subject to any disclaimer, the term of this patent is extended or adjusted under 35 U.S.C. 154(b) by 0 days.

(21) Appl. No.: 15/610,354

(22) Filed: May 31, 2017

(65) Prior Publication Data

US 2018/0030165 A1   Feb. 1, 2018

Related U.S. Application Data

(60) Provisional application No. 62/343,317, filed on May 31, 2016, provisional application No. 62/393,684, filed on Sep. 13, 2016.

(51) Int. Cl.
| | |
|---|---|
| C08F 8/32 | (2006.01) |
| C07D 495/08 | (2006.01) |
| C08F 120/60 | (2006.01) |
| A01N 25/10 | (2006.01) |
| C09D 5/14 | (2006.01) |

(52) U.S. Cl.
CPC .............. *C08F 8/32* (2013.01); *A01N 25/10* (2013.01); *C07D 495/08* (2013.01); *C08F 120/60* (2013.01); *C09D 5/14* (2013.01)

(58) Field of Classification Search
CPC . C08F 26/06; C08F 8/32; C08G 73/06; C08G 73/0605; C08G 73/0622; C08G 73/0666; C08G 73/0683
See application file for complete search history.

(56) References Cited

U.S. PATENT DOCUMENTS

| | | | | |
|---|---|---|---|---|
| 3,644,415 | A * | 2/1972 | Weil | C07F 9/6561 |
| | | | | 204/157.7 |
| 4,366,073 | A * | 12/1982 | McLaughlin | C09K 8/24 |
| | | | | 166/305.1 |
| 4,477,644 | A * | 10/1984 | Sutton | C08G 18/3874 |
| | | | | 264/328.2 |
| 2009/0047517 | A1 | 2/2009 | Caruso et al. | |

(Continued)

OTHER PUBLICATIONS

Accurso, PMSE Preprints, vol. 101, Fall 2009, Aug. 16-20, p. 479-480. (Year: 2009).*

(Continued)

*Primary Examiner* — Robert C Boyle
(74) *Attorney, Agent, or Firm* — Meunier Carlin & Curfman LLC

(57) ABSTRACT

Disclosed are polycationic polymers. The polycationic polymers can include a plurality of positively charged centers, each of which is formed by condensation of cyclic bis-electrophile (e.g., a 9-thia/aza/selenabicyclo[3.3.1]nonyl electrophile) with a nucleophile. The resulting polycationic polymers can efficiently bind nucleic acids. The polycations can also exhibit properties of cytotoxicity and DNA transfection with interesting structure-activity characteristics.

5 Claims, 23 Drawing Sheets

Specification includes a Sequence Listing.

(56) References Cited

OTHER PUBLICATIONS

Weil, E. D.; Smith, K. J.; Gruber, R. J., Transannular Addition of Sulfur Dichloride to Cyclooctadienes. J. Org. Chem. 1966, 31, 1669-1679.
Corey, E. J.; Block, E., New Synthetic Approaches to Symmetrical Sulfur-Bridged Carbocycles. J. Org. Chem. 1966, 31, 1663-1668.
Lautenschlaeger, F., The Reaction of Sulfur Dichloride with cis,cis-1,5-Cyclooctadiene. Can. J. Chem. 1966, 44, 2813-2817.
Converso, A.; Burow, K.; Marzinzik, A.; Sharpless, K. B.; Finn, M. G., "2,6-Dichloro-9-thiabicyclo[3.3.1]nonane: A Privileged, Bivalent Scaffold for the Display of Nucleophilic Components". J. Org. Chem. 2001, 66, 4386-4392.
Converso, A.; Saaidi, P.-L.; Sharpless, K. B.; Finn, M. G., Nucleophilic Substitution by Grignard Reagents on Sulfur Mustards. J. Org. Chem. 2004, 69, 7336-7339.
Yang, H.; Das, N.; Huang, F.; Hawkridge, A. M.; Arif, A. M.; Finn, M. G.; Muddiman, D. C.; Stang, P. J., Incorporation of 2,6-Di(4,4'-dipyridyl)-9-Thiabicyclo[3.3.1]nonane into Discrete 2D Supramolecules via Coordination-Driven Self-Assembly. J. Org. Chem. 2006, 71, 6644-6647.
Accurso, A. A.; Cho, S.-H.; Amin, A.; Potapov, V. A.; Amosova, S. V.; Finn, M. G., "Thia-, Aza-, and Selena[3.3.1]bicyclononane Dichlorides: Rates vs Internal Nucleophile in Anchimeric Assistance". J. Org. Chem. 2011, 76, 4392-4395.
Vincent, J. A. J. M.; Schipper, P.; de Groot, A.; Buck, H. M., Neighboring group participation of sulfur in carbonium ions. Observation of a sulfurane-like intermediate. Tetrahedron Lett. 1975, 16, 1989-1992.
Lehman, M. R.; Thompson, C. D.; Marvel, C. S., Quaternary Ammonium Salts from Halogenated Alkyl Dimethylamines. III. Omega-Bromo-Heptyl-, -Octyl-, -Nonyl- and -Decyl-dimethylamines. J. Am. Chem. Soc. 1933, 55, 1977-1981.
Nemoto, N.; Xu, X.; Sanda, F.; Endo, T., Cationic Ring-Opening Polymerization of Cyclic Monothiocarbonates: Varying the Polymer Main Chain by Neighboring Group Participation. Macromolecules 2001, 34, 7642-7647.
Zussman, M. P.; Tirrell, D. A., Backbone-assisted reactions of polymers. . Poly[(chloromethyl)thiirane]. Macromolecules 1981, 14, 1148-1153.
Dust, J. M.; Secord, M. D., Kinetic and spectroscopic studies of the hydrolysis of bis (2,4-dinitrophenyl ether)s of poly (ethylene glycol). J. Phys. Org. Chem. 1995, 8, 810-824.
Karmalkar, R. N.; Kulkarni, M. G.; Mashelkar, R. A., Pendent chain linked delivery systems: I facile hydrolysis through anchimeric effect. J. Controlled Rel. 1996, 42, 185-193.
Zhao, H.; Yang, K.; Martinez, A.; Basu, A.; Chintala, R.; Liu, H. C.; Janjua, A.; Wang, M. L.; Filpula, D., Linear and branched bicin linkers for releasable PEGylation of macromolecules: Controlled release in vivo and in vitro from mono-and multi-PEGylated proteins. Bioconjugate Chem. 2006, 17, 341-351.
Greenwald, R. B.; Yang, J.; Zhao, H.; Conover, C. D.; Lee, S.; Filpula, D., Controlled release of proteins from their poly(ethylene glycol) conjugates: Drug delivery systems employing 1,6-elimination. Bioconjugate Chem. 2003, 14, 395-403.
Boudreaux, C. J.; Bunyard, W. C.; McCormick, C. L., Controlled activity polymers. XI Hydrolytic release studies of hydrophilic copolymers with labile esters of model allelopathic phenols. J. Controlled Rel. 1997, 44, 185-194.
Kitaura, T.; Tomioka, H.; Fukatani, N.; Kitayama, T., Anchimeric assistance on sequence regulation in partial modification of isotactic poly(propargyl methacrylate) by click reaction. Polym. Chem. 2013, 4, 887-890.

Samal, S. K.; Dash, M.; Van Vlierberghe, S.; Kaplan, D. L.; Chiellini, E.; van Blitterswijk, C.; Moroni, L.; Dubruel, P., Cationic polymers and their therapeutic potential. Chem. Soc. Rev. 2012, 41, 7147-7194.
Russ, V.; Elfberg, H.; Thoma, C.; Kloeckner, J.; Ogris, M.; Wagner, E., Novel degradable oligoethylenimine acrylate ester-based pseudodendrimers for in vitro and in vivo gene transfer. Gene Ther. 2007, 15, 18-29.
Luo, D.; Saltzman, W. M., Synthetic DNA delivery systems. Nat Biotechnol 2000, 18, 33-37.
Green, J. J.; Langer, R.; Anderson, D. G., A Combinatorial Polymer Library Approach Yields Insight into Nonviral Gene Delivery. Acc. Chem. Res. 2008, 41, 749-759.
Knorr, V.; Russ, V.; Allmendinger, L.; Ogris, M.; Wagner, E., Acetal Linked Oligoethylenimines for Use as pH-Sensitive Gene Carriers. Bioconjugate Chemistry 2008, 19, 1625-1634.
Kim, Y. H.; Park, J. H.; Lee, M.; Kim, Y.-H.; Park, T. G.; Kim, S. W., Polyethylenimine with acid-labile linkages as a biodegradable gene carrier. J. Controlled Rel. 2005, 103, 209-219.
Lin, C.; Zhong, Z.; Lok, M. C.; Jiang, X.; Hennink, W. E.; Feijen, J.; Engbersen, J. F. J., Novel Bioreducible Poly(amido amine)s for Highly Efficient Gene Delivery. Bioconjugate Chem. 2006, 18, 138-145.
Thanou, M.; Florea, B. I.; Geldof, M.; Junginger, H. E.; Borchard, G., Quaternized chitosan oligomers as novel gene delivery vectors in epithelial cell lines. Biomaterials 2002, 23, 153-159.
van der Aa, L. J.; Vader, P.; Storm, G.; Schiffelers, R. M.; Engbersen, J. F. J., Intercalating quaternary nicotinamide-based poly(amido amine)s for gene delivery. J. Controlled Rel. 2014, 195, 11-20.
Zhi, D.; Zhang, S.; Cui, S.; Zhao, Y.; Wang, Y.; Zhao, D., The Headgroup Evolution of Cationic Lipids for Gene Delivery. Bioconjugate Chem. 2013, 24, 487-519.
Abboud, J.-u. M.; Notario, R.; Bertran, J.; Sold, M., One Century of Physical Organic Chemistry: The Menshutkin Reaction. In Progress in Physical Organic Chemistry, John Wiley & Sons, Inc.: 2007; pp. 1-182.
Williams, S. R.; Borgerding, E. M.; Layman, J. M.; Wang, W.; Winey, K. I.; Long, T. E., Synthesis and Characterization of Well-Defined 12,12-Ammonium Ionenes: Evaluating Mechanical Properties as a Function of Molecular Weight. Macromolecules 2008, 41, 5216-5222.
Williams, S. R.; Long, T. E., Recent advances in the synthesis and structure-property relationships of ammonium ionenes. Progress in Polymer Science 2009, 34, 762-782.
Zelikin, A. N.; Litmanovich, A. A.; Paraschuk, V. V.; Sybatchin, A. V.; Izumrudov, V. A., Conformational Changes of Aliphatic Ionenes in Water-Salt Solutions as a Factor Controlling Stability of Their Complexes with Calf Thymus DNA. Macromolecules 2003, 36, 2066-2071.
Kugel, A.; Stafslien, S.; Chisholm, B. J., Antimicrobial coatings produced by "tethering" biocides to the coating matrix: A comprehensive review. Progress in Organic Coatings 2011, 72, 222-252.
Abraham, R. J.; Warne, M. A.; Griffiths, L., Proton chemical shifts in NMR .10. Bromine and iodine substituent chemical shifts (SCS) and an analysis of the contributions to the SCS in halocyclohexanes. J. Chem. Soc. Perkin Trans. 2 1997, 2151-2160.
Layman, J. M.; Borgerding, E. M.; Williams, S. R.; Heath, W. H.; Long, T. E., Synthesis and Characterization of Aliphatic Ammonium Ionenes: Aqueous Size Exclusion Chromatography for Absolute Molecular Weight Characterization. Macromolecules 2008, 41, 4635-4641.
Diaz, D. D.; Converso, A.; Sharpless, K. B.; Finn, M. G. 2,6-Dichloro-9-thiabicyclo[3.3.1]nonane: Multigram Display of Azide and Cyanide Components on a Versatile Scaffold. Molecules 2006, 11, 212-218.
Chatterjee, B.; Noveron, J. C.; Resendiz, M. J. E.; Liu, J.; Yamamoto, T.; Parker, D.; Cinke, M.; Nguyen, C. V.;Arif, A. M.; Stang, P. J. J. Am. Chem. Soc. 2004, 126, 10645-10656.
International Search Report and Written Opinion issued in Application No. PCT/US2017/035291, dated Sep. 6, 2017.
Binder, et al., 'Click' Chemistry in Polymer and Materials Science. Macromol. Rapid Commun. 28, 2007, 15-54.

U.S. PATENT DOCUMENTS

| | | | |
|---|---|---|---|
| 2009/0264317 A1 | 10/2009 | Ofir et al. |
| 2011/0294384 A1 | 12/2011 | Locklin et al. |
| 2014/0238939 A1 | 8/2014 | Kasher et al. |

(56) References Cited

OTHER PUBLICATIONS

Lakshmi, et al., Bacterial Adhesion onto azidated poly(vinyl chloride) surfaces. J of Biomed. Mat. Res. Part A 61:1, 2002, 26-32.
Geng, et al., Fragmentable Polycationic Materials Based on Anchimeric Assistance. Chem. Mat. 28:1, 2016, 146-152.
PUBCHEM CID 223672. Create Date Mar. 26, 2005.

* cited by examiner

POLYCATIONS AND METHODS OF MAKING AND USING THEREOF

CROSS-REFERENCE TO RELATED APPLICATIONS

This application claims benefit of U.S. Provisional Application No. 62/343,317, filed May 31, 2016, and U.S. Provisional Application No. 62/393,684, filed Sep. 13, 2016, both of which are hereby incorporated herein by reference in its entirety.

STATEMENT REGARDING FEDERALLY SPONSORED RESEARCH OR DEVELOPMENT

This invention was made with Government Support under Grant No. CHE 1011796 awarded by the National Science Foundation. The Government has certain rights in the invention.

BACKGROUND

Cationic polymers have many unique biological, chemical, and mechanical properties. It is well known that cationic polymers can condense DNA or proteins or proteins for gene or drug delivery. Polycations can be used as an antimicrobial agent to disrupt the membranes of bacteria. However, cationic polymers present cell toxicity and tend to bind proteins that restricts their biomedical applications. For antimicrobial materials, killed microbes can accumulate on the surfaces and decrease their antimicrobial activities.

Despite the usefulness of cationic polymers for biomedical applications, there exists a need for new polymeric materials that offer the advantageous properties of cationic polymers without suffering from their associated disadvantages. The present invention seeks to fulfill this need and provides further related advantages.

SUMMARY

Disclosed herein are polycationic polymers. The polycationic polymers can include a plurality of positively charged centers, each of which is formed by condensation of a cyclic bis-electrophile, such as 9-thia/aza/selenabicyclo[3.3.1] nonyl electrophile, with a nucleophile. The resulting polycationic polymers can efficiently bind nucleic acids. The polycations can also exhibit properties of cytotoxicity and DNA transfection with interesting structure-activity characteristics.

For example, provided herein are polycations defined by Formula I below

Formula I

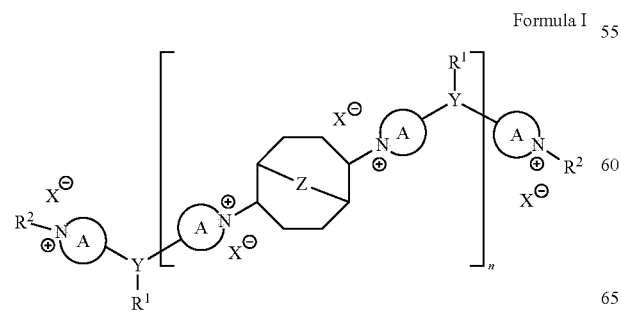

where Z represents, individually for each occurrence, S, Se, or $NR^3$; A represents, individually for each occurrence, a heterocyclic ring comprising a cationic nitrogen center; X represents, individually for each occurrence, an anion; Y is absent, or represents, individually for each occurrence, a linking group; $R^1$ is absent, or represents, individually for each occurrence, halogen, hydroxy, amino, cyano, azido, hydrazone, alkyl, alkenyl, alkynyl, alkoxy, aryl, heteroaryl, alkylaryl, alkylheteroaryl, cycloalkyl alkylcycloalkyl, heterocycloalkyl, alkylheterocycloalkyl, alkylthio, alkylsulfinyl, alkylsulfonyl, alkylamino, dialkylamino, alkylcarbonyl, alkoxycarbonyl, alkylaminocarbonyl, dialkylaminocarbonyl, peptidyl, polyamino, or polyalkyleneoxy; $R^2$ is absent, or represents, individually for each occurrence, alkyl, alkenyl, alkynyl, alkoxy, aryl, heteroaryl, alkylaryl, alkylheteroaryl, cycloalkyl alkylcycloalkyl, heterocycloalkyl, alkylheterocycloalkyl, peptidyl, polyamino, or polyalkyleneoxy; $R^3$ represents, individually for each occurrence, alkyl, alkenyl, alkynyl, alkoxy, aryl, heteroaryl, alkylaryl, alkylheteroaryl, cycloalkyl alkylcycloalkyl, heterocycloalkyl, alkylheterocycloalkyl, peptidyl, polyamino, or polyalkyleneoxy; and n is an integer from 2 to 400 (e.g., from 2 to 200, or from 10 to 50).

X can be, for example, chloride, bromide, iodide, nitrate, sulfate, triflate, borate, and phosphate.

In some embodiments, Z can be S. In other embodiments, Z can be $NR^3$.

In some embodiments, $R^1$, $R^2$, $R^3$, or a combination thereof can comprise a cationic moiety. In some embodiments, $R^1$, $R^2$, $R^3$, or a combination thereof can comprise an alkynyl group or an azido group.

In some embodiments, Y can be chosen from one of the following:

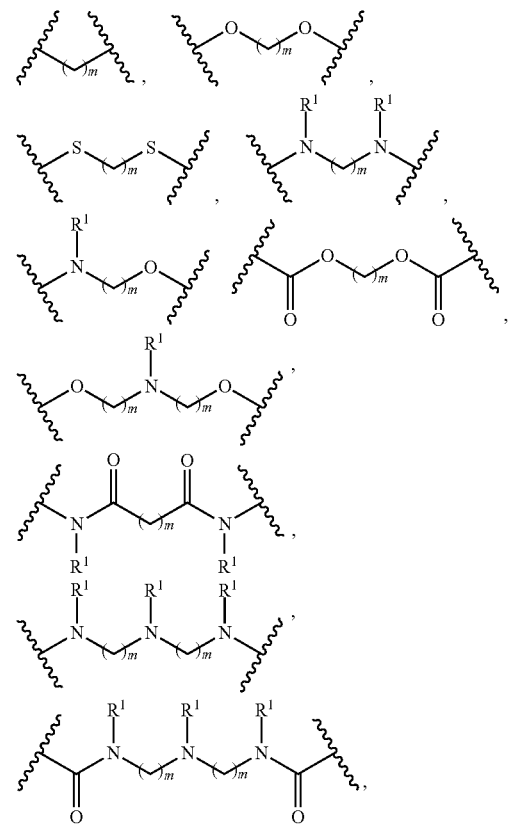

-continued

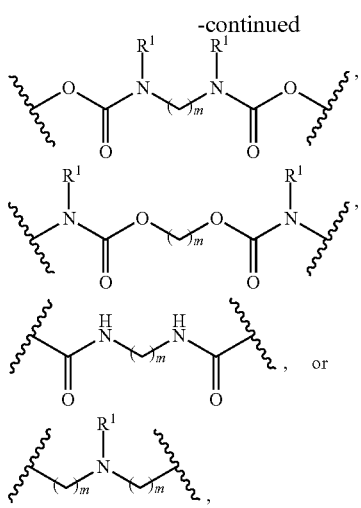

where m is an integer from 1 to 12.

A can be, for example, pyridine, imidazole, pyrazole, triazole, tetrazole, oxazole, isoxazole, furazan, isothioazole, or thiazole. In certain embodiments, A can be a pyridine ring. In these embodiments, the polycation can be defined by Formula IA below Formula IA

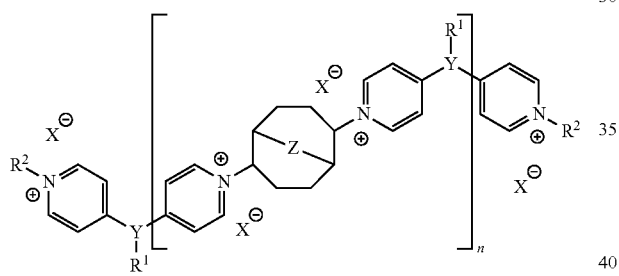

where Z, X, Y, $R^1$, $R^2$, $R^3$, and n are as defined above with respect to Formula I.

Also provided are polycationic polymers derived from the condensation of a cyclic bis-electrophile and a polynucleophilic monomer. The cyclic bis-electrophile can be defined by Formula II below Formula II

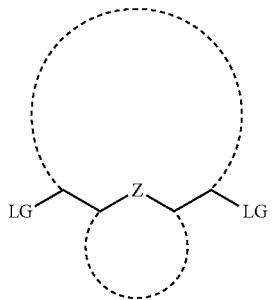

where each dotted line represents a cyclic moiety; LG represents a leaving group; Z represents S, Se, or $NR^3$; and $R^3$ represents alkyl, alkenyl, alkynyl, alkoxy, aryl, heteroaryl, alkylaryl, alkylheteroaryl, cycloalkyl alkylcycloalkyl, heterocycloalkyl, alkylheterocycloalkyl, peptidyl, polyamino, or polyalkyleneoxy. In some embodiments, the cyclic bis-electrophile can be defined by Formula IIA, Formula IIB, or Formula IIC below Formula IIA

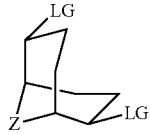

Formula IIB

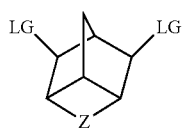

Formula IIC

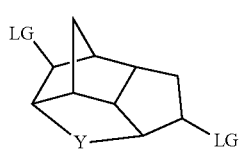

wherein LG and Z are as defined above with respect to Formula II. The polynucleophilic monomer can be defined by Formula III below Formula III

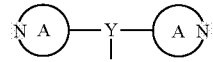

where A represents a heterocyclic ring comprising a tertiary nitrogen atom; Y is absent or represents a linking group; and $R^1$ is absent, or represents halogen, hydroxy, amino, cyano, azido, hydrazone, alkyl, alkenyl, alkynyl, alkoxy, aryl, heteroaryl, alkylaryl, alkylheteroaryl, cycloalkyl alkylcycloalkyl, heterocycloalkyl, alkylheterocycloalkyl, alkylthio, alkylsulfinyl, alkylsulfonyl, alkylamino, dialkylamino, alkylcarbonyl, alkoxycarbonyl, alkylaminocarbonyl, dialkylaminocarbonyl, peptidyl, polyamino, or polyalkyleneoxy.

In some embodiments, the polycationic polymer can be derived from the condensation of cyclic bis-electrophile defined by Formula II, the polynucleophilic monomer defined by Formula III, and a polynucleophilic monomer defined by Formula IV below Formula IV

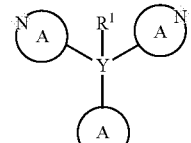

where A represents a heterocyclic ring comprising a tertiary nitrogen atom; Y is absent or represents a linking group; and $R^1$ is absent, or represents halogen, hydroxy, amino, cyano, azido, hydrazone, alkyl, alkenyl, alkynyl, alkoxy, aryl, heteroaryl, alkylaryl, alkylheteroaryl, cycloalkyl alkylcycloalkyl, heterocycloalkyl, alkylheterocycloalkyl, alkylthio, alkylsulfinyl, alkylsulfonyl, alkylamino, dialkylamino, alkylcarbonyl, alkoxycarbonyl, alkylaminocarbonyl, dialkylaminocarbonyl, peptidyl, polyamino, or polyalkyleneoxy.

Also provided are polycationic polymers comprising a recurring unit defined by Formula V below

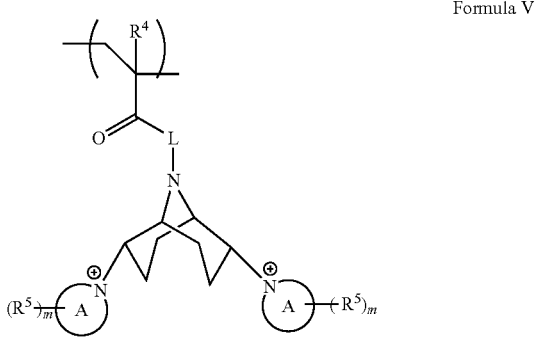

Formula V

Where $R^4$ represents H or methyl; L is absent or represents a linking group; A represents, individually for each occurrence, a heterocyclic ring comprising a cationic nitrogen center; $R^5$ is absent, or represents, individually for each occurrence, halogen, hydroxy, amino, cyano, azido, hydrazone, alkyl, alkenyl, alkynyl, alkoxy, aryl, heteroaryl, alkylaryl, alkylheteroaryl, cycloalkyl alkylcycloalkyl, heterocloalkyl, alkylheterocycloalkyl, alkylthio, alkylsulfinyl, alkylsulfonyl, alkylamino, dialkylamino, alkylcarbonyl, alkoxycarbonyl, alkylaminocarbonyl, dialkylaminocarbonyl, peptidyl, polyamino, or polyalkyleneoxy; and m is an integer from 0 to 5.

In some of these embodiments, the polycationic polymer can further comprise a recurring unit derived from the polymerization of one or more ethylenically-unsaturated monomers (e.g., styrene, butadiene, meth(acrylate) monomers, vinyl acetate, vinyl ester monomers, and combinations thereof).

DESCRIPTION OF DRAWINGS

FIG. 4A shows the downfield region of the $^1$H NMR spectra. FIG. 4B shows the upfield region of the $^1$H NMR spectra.

FIG. 8B shows a differential scanning calorimetry (DSC) trace obtained for polymer 3a.

FIG. 9A shows a box-and-whisker plot of viability test results for GFP-HeLa at different N/P ratios with polymer 3a.

FIG. 10 shows a box-and-whisker plot summarizing the results of siRNA transfection tests at various N/P ratios with polymer 3a.

FIG. 15A shows the results of agarose gel electrophoresis of plasmid DNA mixed with increasing amounts of polycation 3a.

DETAILED DESCRIPTION

Figure 1:
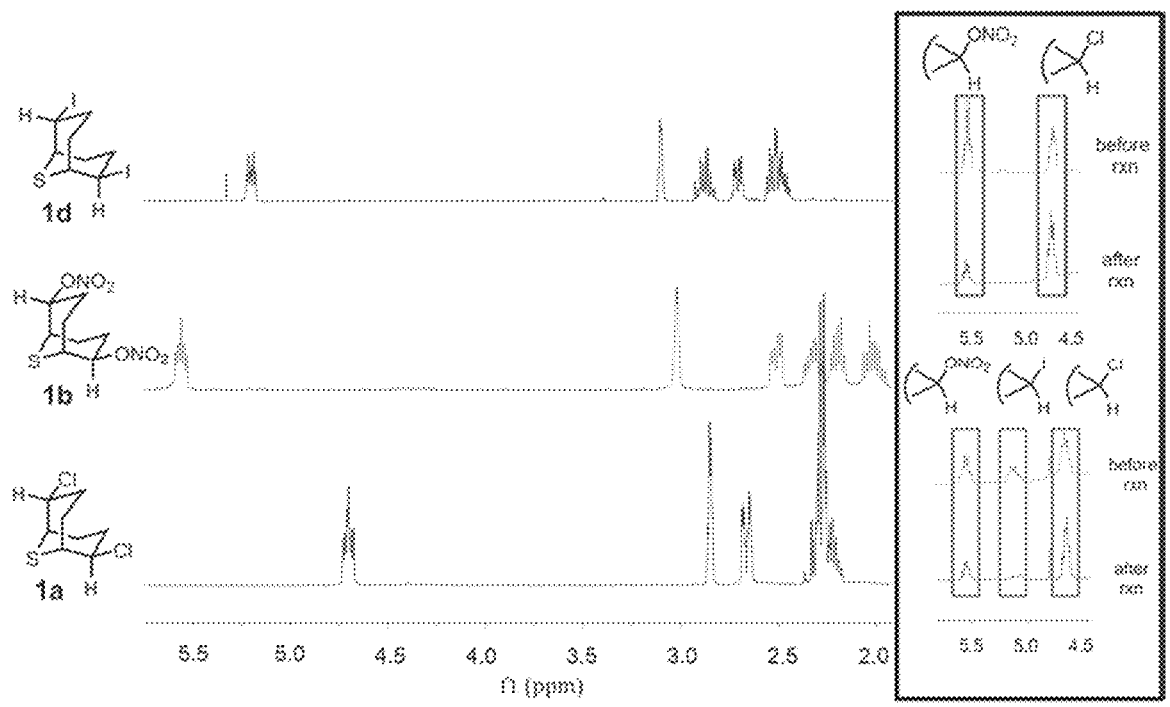
FIG. 1 shows the $^1$H NMR spectra of WCL electrophiles. The inset shows the C1/5-H $^1$H NMR resonances of equimolar mixtures of pairs of electrophiles after reaction with 0.5 equiv. of benzylamine, confirming the reactivity order iodide>nitrate>chloride.

The materials, compounds, compositions, articles, and methods described herein may be understood more readily by reference to the following detailed description of specific aspects of the disclosed subject matter and the Examples and Figures included therein.

Before the present materials, compounds, compositions, and methods are disclosed and described, it is to be understood that the aspects described below are not limited to specific synthetic methods or specific reagents, as such may, of course, vary. It is also to be understood that the terminology used herein is for the purpose of describing particular aspects only and is not intended to be limiting.

Also, throughout this specification, various publications are referenced. The disclosures of these publications in their entireties are hereby incorporated by reference into this application in order to more fully describe the state of the art to which the disclosed matter pertains. The references disclosed are also individually and specifically incorporated by reference herein for the material contained in them that is discussed in the sentence in which the reference is relied upon.

General Definitions

In this specification and in the claims that follow, reference will be made to a number of terms, which shall be defined to have the following meanings:

Throughout the description and claims of this specification the word "comprise" and other forms of the word, such as "comprising" and "comprises," means including but not limited to, and is not intended to exclude, for example, other additives, components, integers, or steps.

As used in the description and the appended claims, the singular forms "a," "an," and "the" include plural referents unless the context clearly dictates otherwise. Thus, for example, reference to "a composition" includes mixtures of two or more such compositions, reference to "the compound" includes mixtures of two or more such compounds, reference to "an agent" includes mixture of two or more such agents, and the like.

"Optional" or "optionally" means that the subsequently described event or circumstance can or cannot occur, and that the description includes instances where the event or circumstance occurs and instances where it does not.

By "reduce" or other forms of the word, such as "reducing" or "reduction," is meant lowering of an event or characteristic (e.g., bacterial growth, biofilm formation, etc.). It is understood that this is typically in relation to some standard or expected value, in other words it is relative, but that it is not always necessary for the standard or relative value to be referred to. For example, "reduces biofilm formation" means reducing the rate of biofilm formation relative to a standard or a control.

By "prevent" or other forms of the word, such as "preventing" or "prevention," is meant to stop a particular event or characteristic, to stabilize or delay the development or progression of a particular event or characteristic, or to minimize the chances that a particular event or characteristic will occur. Prevent does not require comparison to a control as it is typically more absolute than, for example, reduce. As used herein, something could be reduced but not prevented, but something that is reduced could also be prevented. Likewise, something could be prevented but not reduced, but something that is prevented could also be reduced. It is understood that where reduce or prevent are used, unless specifically indicated otherwise, the use of the other word is also expressly disclosed.

It is understood that throughout this specification the identifiers "first" and "second" are used solely to aid in distinguishing the various components and steps of the disclosed subject matter. The identifiers "first" and "second" are not intended to imply any particular order, amount, preference, or importance to the components or steps modified by these terms.

Chemical Definitions

Terms used herein will have their customary meaning in the art unless specified otherwise. The organic moieties mentioned when defining variable positions within the general formulae described herein (e.g., the term "halogen") are collective terms for the individual substituents encompassed by the organic moiety. The prefix $C_n$-$C_m$ indicates in each case the possible number of carbon atoms in the group.

The term "alkyl," as used herein, refers to saturated straight, branched, primary, secondary or tertiary hydrocarbons, including those having 1 to 20 atoms. In some examples, alkyl groups will include $C_1$-$C_{12}$, $C_1$-$C_{10}$, $C_1$-$C_8$, $C_1$-$C_6$, $C_1$-$C_5$, $C_1$-$C_4$, $C_1$-$C_3$, or $C_1$-$C_2$ alkyl groups.

Examples of $C_1$-$C_{10}$ alkyl groups include, but are not limited to, methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl, heptyl, octyl, 2-ethylhexyl, nonyl and decyl groups, as well as their isomers. Examples of $C_1$-$C_4$-alkyl groups include, for example, methyl, ethyl, propyl, 1-methylethyl, butyl, 1-methylpropyl, 2-methylpropyl, and 1,1-dimethylethyl groups.

Optionally, alkyl groups may also contain one or more heteroatoms within the carbon backbone. The heteroatoms incorporated into the carbon backbone may be oxygen, nitrogen, sulfur, or combinations thereof. In certain embodiments, the alkyl group can include between one and four heteroatoms.

Cyclic alkyl groups or "cycloalkyl" groups include cycloalkyl groups having from 3 to 10 carbon atoms. Cycloalkyl groups can include a single ring, or multiple condensed rings. In some examples, cycloalkyl groups include $C_3$-$C_4$, $C_4$-$C_7$, $C_5$-$C_7$, $C_4$-$C_6$, or $C_5$-$C_6$ cyclic alkyl groups. Non-limiting examples of cycloalkyl groups include adamantyl, cyclopropyl, cyclobutyl, cyclopentyl, cyclohexyl, cycloheptyl, cyclooctyl and the like.

Alkyl and cycloalkyl groups can be unsubstituted or substituted with one or more moieties chosen from alkyl, halo, haloalkyl, hydroxyl, carboxyl, acyl, acyloxy, amino, alkyl- or dialkylamino, amido, arylamino, alkoxy, aryloxy, nitro, cyano, azido, thiol, imino, sulfonic acid, sulfate, sulfonyl, sulfanyl, sulfinyl, sulfamonyl, ester, phosphonyl, phosphinyl, phosphoryl, phosphine, thioester, thioether, acid halide, anhydride, oxime, hydrazine, carbamate, phosphoric acid, phosphate, phosphonate, hydrazone, carbonate, ammonium (e.g., a tetraalkylammonium group, a aryltrialkylammonium group, a diaryldialkylammonium group, or a triarylalkylammonium group), pyridinium, or any other viable functional group that does not inhibit the biological activity of the compounds of the invention, either unprotected, or protected as necessary, as known to those skilled in the art, for example, as described in Greene, et al., *Protective Groups in Organic Synthesis*, John Wiley and Sons, Third Edition, 1999, hereby incorporated by reference.

Terms including the term "alkyl," such as "alkylamino" or "dialkylamino," will be understood to comprise an alkyl group as defined above linked to another functional group, where the group is linked to the compound through the last group listed, as understood by those of skill in the art.

The term "alkenyl," as used herein, refers to both straight and branched carbon chains which have at least one carbon-carbon double bond. In some examples, alkenyl groups can include $C_2$-$C_{20}$ alkenyl groups. In other examples, alkenyl can include $C_2$-$C_{12}$, $C_2$-$C_{10}$, $C_2$-$C_8$, $C_2$-$C_6$, or $C_2$-$C_4$ alkenyl groups. In one embodiment of alkenyl, the number of double bonds is 1-3, in another embodiment of alkenyl, the number of double bonds is one or two. Other ranges of carbon-carbon double bonds and carbon numbers are also contemplated depending on the location of the alkenyl moiety on the molecule. "$C_2$-$C_{10}$-alkenyl" groups can include more than one double bond in the chain. The one or more unsaturations within the alkenyl group can be located at any position(s) within the carbon chain as valence permits. In some examples, when the alkenyl group is covalently bound to one or more additional moieties, the carbon atom(s) in the alkenyl group that are covalently bound to the one or more additional moieties are not part of a carbon-carbon double bond within the alkenyl group. Examples of alkenyl groups include, but are not limited to, ethenyl, 1-propenyl, 2-propenyl, 1-methyl-ethenyl, 1-butenyl, 2-butenyl, 3-butenyl, 1-methyl-1-propenyl, 2-methyl-1-propenyl, 1-methyl-2-propenyl, 2-methyl-2-propenyl; 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl and 1-ethyl-2-methyl-2-propenyl groups.

The term "alkynyl," as used herein, refers to both straight and branched carbon chains which have at least one carbon-carbon triple bond. In one embodiment of alkynyl, the number of triple bonds is 1-3; in another embodiment of alkynyl, the number of triple bonds is one or two. In some examples, alkynyl groups include from $C_2$-$C_{20}$ alkynyl groups. In other examples, alkynyl groups can include $C_2$-$C_{12}$, $C_2$-$C_{10}$, $C_2$-$C_8$, $C_2$-$C_6$ or $C_2$-$C_4$ alkynyl groups. Other ranges of carbon-carbon triple bonds and carbon numbers are also contemplated depending on the location of the alkenyl moiety on the molecule. For example, the term "$C_2$-$C_{10}$-alkynyl" as used herein refers to a straight-chain or branched unsaturated hydrocarbon group having 2 to 10 carbon atoms and containing at least one triple bond, such as ethynyl, prop-1-yn-1-yl, prop-2-yn-1-yl, n-but-1-yn-1-yl, n-but-1-yn-3-yl, n-but-1-yn-4-yl, n-but-2-yn-1-yl, n-pent-1-yn-1-yl, n-pent-1-yn-3-yl, n-pent-1-yn-4-yl, n-pent-1-yn-5-yl, n-pent-2-yn-1-yl, n-pent-2-yn-4-yl, n-pent-2-yn-5-yl, 3-methylbut-1-yn-3-yl, 3-methylbut-1-yn-4-yl, n-hex-1-yn-1-yl, n-hex-1-yn-3-yl, n-hex-1-yn-4-yl, n-hex-1-yn-5-yl, n-hex-1-yn-6-yl, n-hex-2-yn-1-yl, n-hex-2-yn-4-yl, n-hex-2-yn-5-yl, n-hex-2-yn-6-yl, n-hex-3-yn-1-yl, n-hex-3-yn-2-yl, 3-methylpent-1-yn-1-yl, 3-methylpent-1-yn-3-yl, 3-methylpent-1-yn-4-yl, 3-methylpent-1-yn-5-yl, 4-methylpent-1-yn-1-yl, 4-methylpent-2-yn-4-yl, and 4-methylpent-2-yn-5-yl groups.

Alkenyl and alkynyl groups can be unsubstituted or substituted with one or more moieties chosen from alkyl, halo, haloalkyl, hydroxyl, carboxyl, acyl, acyloxy, amino, alkyl- or dialkylamino, amido, arylamino, alkoxy, aryloxy, nitro, cyano, azido, thiol, imino, sulfonic acid, sulfate, sulfonyl, sulfanyl, sulfinyl, sulfamonyl, ester, phosphonyl, phosphinyl, phosphoryl, phosphine, thioester, thioether, acid halide, anhydride, oxime, hydrazine, carbamate, phosphoric acid, phosphate, phosphonate, hydrazone, carbonate, ammonium (e.g., a tetraalkylammonium group, a aryltrialkylammonium group, a diaryldialkylammonium group, or a triarylalkylammonium group), pyridinium, or any other viable functional group that does not inhibit the biological activity of the compounds of the invention, either unprotected, or protected as necessary, as known to those skilled in the art, for example, as described in Greene, et al., *Protective Groups in Organic Synthesis*, John Wiley and Sons, Third Edition, 1999.

The term "aryl," as used herein, refers to a monovalent aromatic carbocyclic group of from 6 to 14 carbon atoms. Aryl groups can include a single ring or multiple condensed rings. In some examples, aryl groups include $C_6$-$C_{10}$ aryl groups. Aryl groups include, but are not limited to, phenyl, biphenyl, naphthyl, tetrahydronaphtyl, phenylcyclopropyl and indanyl. Aryl groups can be unsubstituted or substituted by one or more moieties chosen from halo, cyano, nitro, hydroxy, mercapto, amino, alkyl, alkenyl, alkynyl, cycloalkyl, cycloalkenyl, haloalkyl, haloalkenyl, haloalkynyl, halocycloalkyl, halocycloalkenyl, alkoxy, alkenyloxy, alkynyloxy, haloalkoxy, haloalkenyloxy, haloalkynyloxy, cycloalkoxy, cycloalkenyloxy, halocycloalkoxy, halocycloalkenyloxy, alkylthio, haloalkylthio, cycloalkylthio, halocycloalkylthio, alkylsulfinyl, alkenylsulfinyl, alkynylsulfinyl, haloalkylsulfinyl, haloalkenylsulfinyl, haloalkynylsulfinyl, alkylsulfonyl, alkenylsulfonyl, alkynylsulfonyl, haloalkyl-sulfonyl, haloalkenylsulfonyl, haloalkynylsulfonyl, alkylamino, alkenylamino, alkynylamino, di(alkyl)amino, di(alkenyl)-amino, di(alkynyl)amino, or trialkylsilyl.

The term "alkylaryl," as used herein, refers to an aryl group that is bonded to a parent compound through a diradical alkylene bridge, (—$CH_2$—)$_n$, where n is 1-12 (e.g., n is from 1 to 6) and where "aryl" is as defined above. The term "arylalkyl," as used herein, refers to an aryl group, as defined above, which is substituted by an alkyl group, as defined above.

The term "alkylcycloalkyl," as used herein, refers to a cycloalkyl group that is bonded to a parent compound through a diradical alkylene bridge, (—$CH_2$—)$_n$, where n is 1-12 (e.g., n is from 1 to 6) and where "cycloalkyl" is as defined above.

The term "alkoxy," as used herein, refers to alkyl-O—, wherein alkyl refers to an alkyl group, as defined above. Similarly, the terms "alkenyloxy," "alkynyloxy," and "cycloalkoxy," refer to the groups alkenyl-O—, alkynyl-O—, and cycloalkyl-O—, respectively, wherein alkenyl, alkynyl, and cycloalkyl are as defined above. Examples of $C_1$-$C_6$-alkoxy groups include, but are not limited to, methoxy, ethoxy, $C_2H_5$—$CH_2O$—, $(CH_3)_2CHO$—, n-butoxy, $C_2H_5$—$CH(CH_3)O$—, $(CH_3)_2CH$—$CH_2O$—, $(CH_3)_3CO$—, n-pentoxy, 1-methylbutoxy, 2-methylbutoxy, 3-methylbutoxy, 1,1-dimethylpropoxy, 1,2-dimethylpropoxy, 2,2-dimethyl-propoxy, 1-ethylpropoxy, n-hexoxy, 1-methylpentoxy, 2-methylpentoxy, 3-methylpentoxy, 4-methylpentoxy, 1,1-dimethylbutoxy, 1,2-dimethylbutoxy, 1,3-dimethylbutoxy, 2,2-dimethylbutoxy, 2,3-dimethylbutoxy, 3,3-dimethylbutoxy, 1-ethylbutoxy, 2-ethylbutoxy, 1,1,2-trimethylpropoxy, 1,2,2-trimethylpropoxy, 1-ethyl-1-methylpropoxy, and 1-ethyl-2-methylpropoxy.

The term "alkylthio," as used herein, refers to alkyl-S—, wherein alkyl refers to an alkyl group, as defined above. Similarly, the term "cycloalkylthio," refers to cycloalkyl-S— where cycloalkyl are as defined above.

The term "alkylsulfinyl," as used herein, refers to alkyl-S(O)—, wherein alkyl refers to an alkyl group, as defined above.

The term "alkylsulfonyl," as used herein, refers to alkyl-S(O)$_2$—, wherein alkyl is as defined above.

The terms "alkylamino" and "dialkylamino," as used herein, refer to alkyl-NH— and (alkyl)$_2$N-groups, where alkyl is as defined above.

The terms "alkylcarbonyl," "alkoxycarbonyl," "alkylaminocarbonyl," and "dialkylaminocarbonyl," as used herein, refer to alkyl-C(O)—, alkoxy-C(O)—, alkylamino-C(O)— and dialkylamino-C(O)— respectively, where alkyl, alkoxy, alkylamino, and dialkylamino are as defined above.

The term "heteroaryl," as used herein, refers to a monovalent aromatic group of from 1 to 15 carbon atoms (e.g., from 1 to 10 carbon atoms, from 2 to 8 carbon atoms, from 3 to 6 carbon atoms, or from 4 to 6 carbon atoms) having one or more heteroatoms within the ring. The heteroaryl group can include from 1 to 4 heteroatoms, from 1 to 3 heteroatoms, or from 1 to 2 heteroatoms. In some examples, the heteroatom(s) incorporated into the ring are oxygen, nitrogen, sulfur, or combinations thereof. When present, the nitrogen and sulfur heteroatoms can optionally be oxidized. Heteroaryl groups can have a single ring (e.g., pyridyl or furyl) or multiple condensed rings provided that the point of attachment is through a heteroaryl ring atom. Preferred heteroaryls include pyridyl, piridazinyl, pyrimidinyl, pyrazinyl, triazinyl, pyrrolyl, indolyl, quinolinyl, isoquinolinyl, quinazolinyl, quinoxalinnyl, furanyl, thiophenyl, furyl, pyrrolyl, imidazolyl, oxazolyl, isoxazolyl, isothiazolyl, pyrazolyl benzofuranyl, and benzothiophenyl. Heteroaryl rings can be unsubstituted or substituted by one or more moieties as described for aryl above.

The term "alkylheteroaryl," as used herein, refers to a heteroaryl group that is bonded to a parent compound through a diradical alkylene bridge, (—$CH_2$—)$_n$, where n is 1-12 and where "heteroaryl" is as defined above.

The terms "heterocyclyl," "heterocyclic" and "heterocyclo" are used herein interchangeably, and refer to fully saturated or unsaturated, cyclic groups, for example, 3 to 7 membered monocyclic or 4 to 7 membered monocyclic; 7 to 11 membered bicyclic, or 10 to 15 membered tricyclic ring systems, having one or more heteroatoms within the ring. The heterocyclyl group can include from 1 to 4 heteroatoms, from 1 to 3 heteroatoms, or from 1 to 2 heteroatoms. In some examples, the heteroatom(s) incorporated into the ring are oxygen, nitrogen, sulfur, or combinations thereof. When present, the nitrogen and sulfur heteroatoms can optionally be oxidized, and the nitrogen heteroatoms can optionally be quaternized. The heterocyclyl group can be attached at any heteroatom or carbon atom of the ring or ring system and can be unsubstituted or substituted by one or moieties as described for aryl groups above.

Exemplary monocyclic heterocyclic groups include, but are not limited to, pyrrolidinyl, pyrrolyl, pyrazolyl, oxetanyl, pyrazolinyl, imidazolyl, imidazolinyl, imidazolidinyl, oxazolyl, oxazolidinyl, isoxazolinyl, isoxazolyl, thiazolyl, thiadiazolyl, thiazolidinyl, isothiazolyl, isothiazolidinyl, furyl, tetrahydrofuryl, thienyl, oxadiazolyl, piperidinyl, piperazinyl, 2-oxopiperazinyl, 2-oxopiperidinyl, 2-oxopyrrolodinyl, 2-oxoazepinyl, azepinyl, 4-piperidonyl, pyridinyl, pyrazinyl, pyrimidinyl, pyridazinyl, tetrahydropyranyl, morpholinyl, thiamorpholinyl, thiamorpholinyl sulfoxide, thiamorpholinyl sulfone, 1,3-dioxolane and tetrahydro-1,1-dioxothienyl, triazolyl, triazinyl, and the like.

Exemplary bicyclic heterocyclic groups include, but are not limited to, indolyl, benzothiazolyl, benzoxazolyl, benzodioxolyl, benzothienyl, quinuclidinyl, quinolinyl, tetrahydroisoquinolinyl, isoquinolinyl, benzimidazolyl, benzopyranyl, indolizinyl, benzofuryl, chromonyl, coumarinyl, benzopyranyl, cinnolinyl, quinoxalinyl, indazolyl, pyrrolopyridyl, furopyridinyl (such as furo[2,3-c]pyridinyl, furo[3, 2-b]pyridinyl]or furo[2,3-b]pyridinyl), dihydroisoindolyl, dihydroquinazolinyl (such as 3,4-dihydro-4-oxo-quinazolinyl), tetrahydroquinolinyl and the like.

Exemplary tricyclic heterocyclic groups include carbazolyl, benzidolyl, phenanthrolinyl, acridinyl, phenanthridinyl, xanthenyl, and the like.

The term "alkylheterocyclyl," as used herein, refers to a heterocyclyl group that is bonded to a parent compound through a diradical alkylene bridge, $(-CH_2-)_n$, where n is 1-12 and where "heterocyclyl" is as defined above. The term "heterocyclylalkyl," as used herein, refers to a heterocyclyl group, as defined above, which is substituted by an alkyl group, as defined above.

Heretrocyclyl and heteroaryl groups can be unsubstituted or substituted with one or more moieties chosen from alkyl, halo, haloalkyl, hydroxyl, carboxyl, acyl, acyloxy, amino, alkyl- or dialkylamino, amido, arylamino, alkoxy, aryloxy, nitro, cyano, azido, thiol, imino, sulfonic acid, sulfate, sulfonyl, sulfanyl, sulfinyl, sulfamonyl, ester, phosphonyl, phosphinyl, phosphoryl, phosphine, thioester, thioether, acid halide, anhydride, oxime, hydrazine, carbamate, phosphoric acid, phosphate, phosphonate, hydrazone, carbonate, ammonium (e.g., a tetraalkylammonium group, a aryltrialkylammonium group, a diaryldialkylammonium group, or a triarylalkylammonium group), pyridinium, or any other viable functional group that does not inhibit the biological activity of the compounds of the invention, either unprotected, or protected as necessary, as known to those skilled in the art, for example, as described in Greene, et al., *Protective Groups in Organic Synthesis*, John Wiley and Sons, Third Edition, 1999 The term "halogen," as used herein, refers to the atoms fluorine, chlorine, bromine and iodine. The prefix halo- (e.g., as illustrated by the term haloalkyl) refers to all degrees of halogen substitution, from a single substitution to a perhalo substitution (e.g., as illustrated with methyl as chloromethyl ($-CH_2Cl$), dichloromethyl ($-CHCl_2$), trichloromethyl ($-CCl_3$)).

The term "polyalkyleneoxy," as used herein, generally refers to an oligomeric or polymeric group formed from the following repeating alkyleneoxy units: $-CH_2CH_2O-$, $CH_2CH_2CH_2O-$, $-CH_2CH_2CH_2CH_2O-$, $-CH_2CH(CH_3)O-$, $-CH_2CH(CH_2CH_3)O-CH_2CH_2CH(CH_3)O-$, and any combination thereof. The number of repeat alkyleneoxy groups typically is from 2 to 50 (e.g., from 5 to 50, from 10 to 50, from 2 to 40, from 5 to 40, from 10 to 40, from 2 to 30, from 5 to 30, from 10 to 30, from 2 to 20, from 5 to 20, from 10 to 20, from 2 to 15, from 5 to 15, from 10 to 15, from 2 to 10, or from 5 to 10) repeat alkyleneoxy groups, although the number of repeat units can be outside of these ranges. The term "pendant", as used herein in reference to a polyalkyleneoxy group, refers to a polyalkyleneoxy group that is present as an end group and/or a sidechain attached to a polymeric backbone.

The term "polyamino," as used herein, generally refers to an oligomeric or polymeric group derived from one or more monomers containing an amine group. Suitable monomers of this type include vinylamine, allylamine, and ethyleneimine. Other suitable amino-containing monomers include (meth)acrylate monomers containing one or more primary and/or secondary amine groups, such as 2-aminoethyl methacrylate, 2-aminoethyl acrylate, 2-(tert-butylamino)ethyl acrylate, 2-(tert-butylamino)ethyl methacrylate. In some cases, the polyamino group can be a polycationic polyamino group (e.g., polyethyleneimine). The term "pendant", as used herein in reference to a polyamino group, refers to a polyamino group that is present as an end group and/or a sidechain attached to a polymeric backbone.

As used herein, the term "(meth)acrylate monomer" includes acrylate, methacrylate, diacrylate, and dimethacrylate monomers.

As used herein, the term "substituted" is contemplated to include all permissible substituents of organic compounds. In a broad aspect, the permissible substituents include acyclic and cyclic, branched and unbranched, carbocyclic and heterocyclic, and aromatic and nonaromatic substituents of organic compounds. Illustrative substituents include, for example, Such substituents include, but are not limited to, halogen, hydroxyl, carbonyl (such as a carboxyl, alkoxycarbonyl, formyl, or an acyl), thiocarbonyl (such as a thioester, a thioacetate, or a thioformate), alkoxyl, phosphoryl, phosphate, phosphonate, a phosphinate, amino, amido, amidine, imine, cyano, nitro, azido, sulfhydryl, alkylthio, sulfate, sulfonate, sulfamoyl, sulfonamido, sulfonyl, heterocyclyl, aralkyl, hydrazone, carbonate, ammonium (e.g., a tetraalkylammonium group, a aryltrialkylammonium group, a diaryldialkylammonium group, or a triarylalkylammonium group), pyridinium, or an aromatic or heteroaromatic moiety.

The permissible substituents can be one or more and the same or different for appropriate organic compounds. For purposes of this disclosure, the heteroatoms, such as nitrogen, can have hydrogen substituents and/or any permissible substituents of organic compounds described herein which satisfy the valences of the heteroatoms. This disclosure is not intended to be limited in any manner by the permissible substituents of organic compounds. Also, the terms "substitution" or "substituted with" include the implicit proviso that such substitution is in accordance with permitted valence of the substituted atom and the substituent, and that the substitution results in a stable compound, e.g., a compound that does not spontaneously undergo transformation such as by rearrangement, cyclization, elimination, etc.

Unless stated to the contrary, a formula with chemical bonds shown only as solid lines and not as wedges or dashed lines contemplates each possible isomer, e.g., each enantiomer, diastereomer, and meso compound, and a mixture of isomers, such as a racemic or scalemic mixture.

Reference will now be made in detail to specific aspects of the disclosed materials, compounds, compositions, articles, and methods, examples of which are illustrated in the accompanying Examples and Figures.

Polycations

Provided herein are polycationic polymers. The polycationic polymers can include a plurality of positively charged centers, each of which is formed by condensation of cyclic bis-electrophile, such as a 9-thia/aza/selenabicyclo[3.3.1]nonyl electrophile, with a nucleophile. The resulting polycationic polymers can efficiently bind nucleic acids. The polycations can also exhibit properties of cytotoxicity and DNA transfection with interesting structure-activity characteristics.

In some cases, the polycationic polymer can be formed by the condensation of cyclic bis-electrophile (e.g., a 9-thia/aza/selenabicyclo[3.3.1]nonyl dielectrophile) with a polynucleophiles (e.g., a dinucleophiles). Each bond-forming event in this condensation polymerization process generates a positively charged center within the polymer backbone. In these systems, the length of the polymer chain was found to be dependent on the reactivity of the electrophile, which can be readily tuned through variation of the leaving group β to sulfur/nitrogen/selenium atom present in the cyclic bis-electrophile. These polycations can also be biodegradable. Degradation of the polycations can occur via hydrolysis, with the rate of hydrolysis dependent on the leaving-group ability of the nucleophile (which correlates roughly with the $pK_a$ of the nucleophile's conjugate acid). Thus, the degradation rates of the polycations can be tuned through selection of an appropriate nucleophile. Polymer decomposition occurs simultaneously throughout the length of the chains, rather than from the ends; the decomposition products can be only minimally toxic to mammalian cells.

In some embodiments, the polycationic polymer can be derived from the condensation of a cyclic bis-electrophile and a polynucleophilic monomer. The cyclic bis-electrophile can be defined by Formula II below Formula II

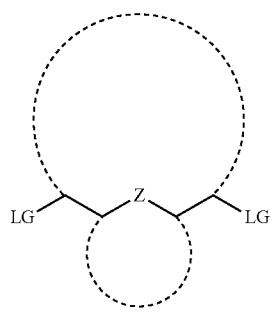

where each dotted line represents a cyclic moiety; LG represents a leaving group; Z represents S, Se, or $NR^3$; and $R^3$ represents alkyl, alkenyl, alkynyl, alkoxy, aryl, heteroaryl, alkylaryl, alkylheteroaryl, cycloalkyl alkylcycloalkyl, heterocycloalkyl, alkylheterocycloalkyl, peptidyl, polyamino, or polyalkyleneoxy. In some embodiments, the cyclic bis-electrophile can be defined by Formula IIA, Formula IIB, or Formula IIC below Formula IIA

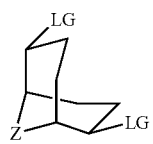

Formula IIB

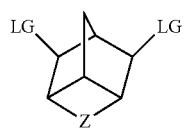

Formula IIC

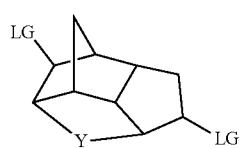

wherein LG and Z are as defined above with respect to Formula II. The polynucleophilic monomer can be defined by Formula III below Formula III

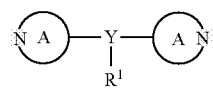

wherein A represents a heterocyclic ring comprising a tertiary nitrogen atom; Y is absent or represents a linking group; and $R^1$ is absent, or represents halogen, hydroxy, amino, cyano, azido, hydrazone, alkyl, alkenyl, alkynyl, alkoxy, aryl, heteroaryl, alkylaryl, alkylheteroaryl, cycloalkyl alkylcycloalkyl, heterocycloalkyl, alkylheterocycloalkyl, alkylthio, alkylsulfinyl, alkylsulfonyl, alkylamino, dialkylamino, alkylcarbonyl, alkoxycarbonyl, alkylaminocarbonyl, dialkylaminocarbonyl, peptidyl, polyamino, or polyalkyleneoxy.

In some embodiments, the polycationic polymer can be derived from the condensation of a single species of cyclic bis-electrophile defined by Formula II and a single species of polynucleophilic monomer defined by Formula III. In other embodiments, the polycationic polymer can be derived from the condensation of a single species of cyclic bis-electrophile defined by Formula II and two or more different species of polynucleophilic monomer defined by Formula III. In other embodiments, the polycationic polymer can be derived from the condensation of two or more different species of cyclic bis-electrophile defined by Formula II and a single species of polynucleophilic monomer defined by Formula III. In other embodiments, the polycationic polymer can be derived from the condensation of two or more different species of cyclic bis-electrophile defined by Formula II and two or more different species of polynucleophilic monomer defined by Formula III.

In some embodiments of Formula II, Z can be S. In other embodiments, Z can be $NR^3$.

In some embodiments of Formula II, Z can be $NR^3$, and $R^3$ can comprise a cationic group. For example, in certain embodiments, the cationic group can comprise a cationic polyamino group (e.g., a polyethyleneimine segment). In other embodiments, the cationic group can comprise a cationic peptidyl group. In other embodiments, the cationic group can comprise a moiety (e.g., an alkyl group or an alkylaryl group) substituted with a cationic substituent, such as an ammonium group (e.g., a tetraalkylammonium group, a aryltrialkylammonium group, a diaryldialkylammonium group, or a triarylalkylammonium group) or a pyridinium group.

In some embodiments of Formula II, Z can be $NR^3$, and $R^3$ can comprise a hydrophobic group. For example, in certain embodiments, Z can be $NR^3$, and $R^3$ can comprise an aryl group or an alkylaryl group.

In some embodiments of Formula II, Z can be $NR^3$, and $R^3$ can comprise a hydrophilic group. For example, in certain embodiments, Z can be $NR^3$, and $R^3$ can comprise a hydrophilic polyalkyleneoxy group (e.g., a polyethylene oxide segment).

In some embodiments of Formula II, Z can be $NR^3$, and $R^3$ can comprise a reactive functional group. Reactive functional groups include moieties that can participate in a reaction with another moiety, which may also be a reactive functional group, to form a covalent bond. Examples of reactive functional groups include, but are not limited to, olefins, acetylenes, alcohols, phenols, ethers, oxides, halides, aldehydes, ketones, carboxylic acids, esters, amides, cyanates, isocyanates, thiocyanates, isothiocyanates, amines, hydrazines, hydrazones, hydrazides, diazo, diazonium, nitro, nitriles, mercaptans, sulfides, disulfides, sulfoxides, sulfones, sulfonic acids, sulfinic acids, acetals, ketals, anhydrides, sulfates, sulfenic acids isonitriles, amidines, imides, imidates, nitrones, hydroxylamines, oximes, hydroxamic acids thiohydroxamic acids, allenes, ortho esters, sulfites, enamines, ynamines, ureas, pseudoureas, semicarbazides, carbodiimides, carbamates, imines, azides, azo compounds, azoxy compounds, and nitroso compounds. Reactive functional groups also include those used to prepare bioconjugates, e.g., N-hydroxysuccinimide esters, maleimides and the like. Methods to prepare each of these functional groups are well known in the art and their application to or modification for a particular purpose is within the ability of one of skill in the art. See, for example, Sandler and Karo, eds. *Organic Functional Group Preparations*, Academic Press, San Diego, 1989. For example, in certain embodiments, Z can be $NR^3$, and $R^3$ can comprise an alkynyl group or an azido group. In other embodiments, Z can be $NR^3$, and $R^3$ can comprise a hydrazone group.

LG can represent any suitable leaving group. Leaving groups are well known in the art, and include substituent present within a chemical compound that can be readily displaced. Examples of leaving groups include halides (chloride, bromide, and iodide), triflates (OTO, boron moieties including boronic acids and trihaloborate salts such as trifluoroborate salts ($BF_3$), diazonium salts ($N_2^+$), tosylates (OTs) and other sulfonic esters, mesylates (OMs), nitrates ($-ONO_2$), and phosphates ($-OPO(OH)_2$). In some examples, LG can be a halide (e.g., chloride, bromide, or iodide). In other examples, LG can be triflate. In other examples, LG can be nitrate.

A can be any heterocyclic ring comprising a tertiary nitrogen atom. In some embodiments, A can be a heteroaromatic ring. In some embodiments, A can comprise one or more additional heteroatoms in addition to the tertiary nitrogen atom (e.g., one or more additional nitrogen atoms, one or more oxygen atoms, one or more sulfur atoms, or a combination thereof). For example, A can be chosen from pyridine, imidazole, pyrazole, triazole, tetrazole, oxazole, isoxazole, furazan, isothioazole, and thiazole. In certain embodiments, A can represent a pyridine ring.

In some embodiments, Y can be absent (i.e., the two heterocyclic rings can be bound directly to one another). In other embodiments, Y is present. When present, the linking group can be any suitable group or moiety which is at minimum bivalent, and connects the heterocyclic rings in the nucleophile. The linking group can be composed of any assembly of atoms, including oligomeric and polymeric chains. In some cases, the total number of atoms in the linking group can be from 3 to 200 atoms (e.g., from 3 to 150 atoms, from 3 to 100 atoms, from 3 and 50 atoms, from 3 to 25 atoms, from 3 to 15 atoms, or from 3 to 10 atoms). In some embodiments, the linking group can be, for example, an alkyl, alkoxy, alkylaryl, alkylheteroaryl, alkylcycloalkyl, alkylheterocycloalkyl, alkylthio, alkylsulfinyl, alkylsulfonyl, alkylamino, dialkylamino, alkylcarbonyl, alkoxycarbonyl, alkylaminocarbonyl, dialkylaminocarbonyl, or polyamino group. In some embodiments, the linking group can comprises one of the groups above joined to each of the heterocyclic rings by a functional group. Examples of suitable functional groups include, for example, secondary amides ($-CONH-$), tertiary amides ($-CONR-$), secondary carbamates ($-OCONH-$; $-NHCOO-$), tertiary carbamates ($-OCONR-$; $-NRCOO-$), ureas ($-NHCONH-$; $-NRCONH-$; $-NHCONR-$, or $-NRCONR-$), carbinols ($-CHOH-$, $-CROH-$), ethers ($-O-$), and esters ($-COO-$, $-CH_2O_2C-$, $CHRO_2C-$), wherein R is an alkyl group, an aryl group, or a heterocyclic group. For example, in some embodiments, the linking group can comprise an alkyl group (e.g., a $C_1$-$C_{12}$ alkyl group, a $C_1$-$C_8$ alkyl group, or a $C_1$-$C_6$ alkyl group) bound to each heterocyclic ring via an ester ($-COO-$, $-CH_2O_2C-$, $CHRO_2C-$), a secondary amide ($-CONH-$), or a tertiary amide ($-CONR-$), wherein R is an alkyl group, an aryl group, or a heterocyclic group. In certain embodiments, Y can be chosen from one of the following:

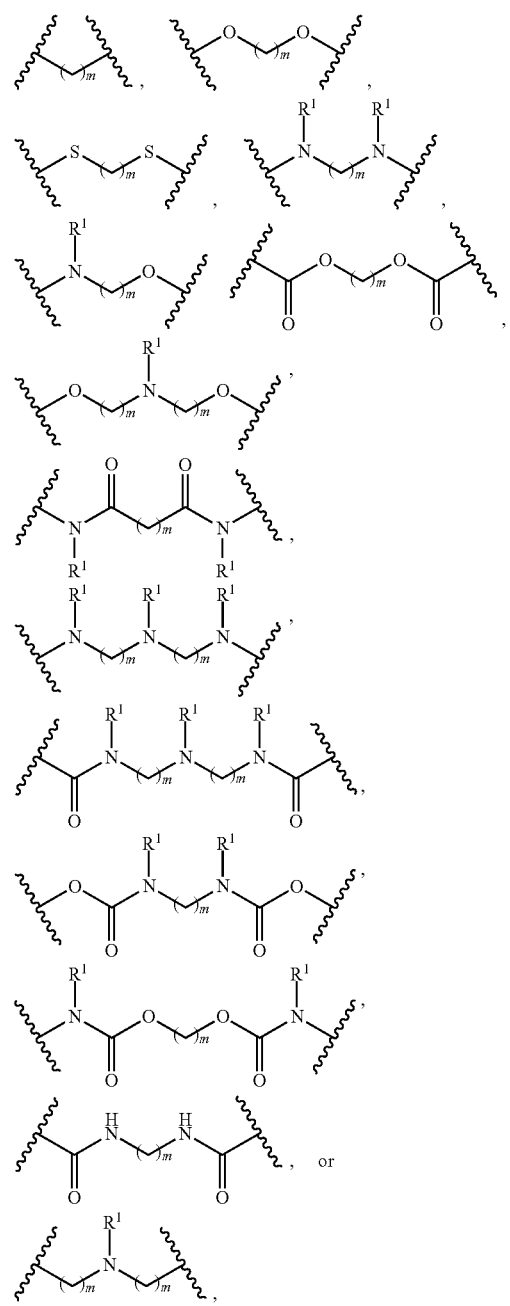

where m is an integer from 1 to 12.

In some embodiments, $R^1$ can be absent. In other embodiments, $R^1$ can be present. When present, $R^1$ can comprise a halogen, hydroxy, amino, cyano, azido, hydrazone, alkyl, alkenyl, alkynyl, alkoxy, aryl, heteroaryl, alkylaryl, alkylheteroaryl, cycloalkyl alkylcycloalkyl, heterocycloalkyl, alkylheterocycloalkyl, alkylthio, alkylsulfinyl, alkylsulfonyl, alkylamino, dialkylamino, alkylcarbonyl, alkoxycarbonyl, alkylaminocarbonyl, dialkylaminocarbonyl, peptidyl, polyamino, or polyalkyleneoxy group.

In some embodiments, $R^1$ can comprise a cationic group. In certain embodiments, the cationic group can comprise a cationic polyamino group (e.g., a polyethyleneimine segment). In other embodiments, the cationic group can comprise a cationic peptidyl group. In other embodiments, the cationic group can comprise a moiety (e.g., an alkyl group or an alkylaryl group) substituted with a cationic substituent, such as an ammonium group (e.g., a tetraalkylammonium group, an aryltrialkylammonium group, a diaryldialkylammonium group, or a triarylalkylammonium group) or a pyridinium group.

In some embodiments, $R^1$ can comprise a hydrophobic group. For example, in certain embodiments, $R^1$ can comprise an aryl group or an alkylaryl group. In some embodiments, $R^1$ can comprise a hydrophilic group. For example, in certain embodiments, $R^1$ can comprise a hydrophilic polyalkyleneoxy group (e.g., a polyethylene oxide segment).

In some embodiments, $R^1$ can comprise a reactive functional group, such as an olefin, acetylene, alcohol, phenol, ether, oxide, halide, aldehyde, ketone, carboxylic acid, ester, amide, cyanate, isocyanate, thiocyanate, isothiocyanate, amine, hydrazine, hydrazone, hydrazide, diazo, diazonium, nitro, nitrile, mercaptan, sulfide, disulfide, sulfoxide, sulfone, sulfonic acid, sulfinic acid, acetal, ketal, anhydride, sulfate, sulfenic acid isonitrile, amidine, imide, imidate, nitrone, hydroxylamine, oxime, hydroxamic acid, thiohydroxamic acid, allene, ortho ester, sulfite, enamine, ynamine, urea, pseudourea, semicarbazide, carbodiimide, carbamate, imine, azide, azo group, azoxy group, nitroso group, N-hydroxysuccinimide ester, or maleimides. For example, in certain embodiments, $R^1$ can comprise an alkynyl group or an azido group. In other embodiments, $R^1$ can comprise a hydrazone group.

In some embodiments, the polycationic polymer polymer can be derived from the condensation of one or more cyclic bis-electrophiles defined by Formula II, one or more polynucleophilic monomers defined by Formula III, and one or more polynucleophilic monomers defined by Formula IV below

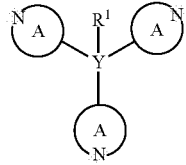

Formula IV wherein A represents a heterocyclic ring comprising a tertiary nitrogen atom; Y is absent or represents a linking group; and $R^1$ is absent, or represents halogen, hydroxy, amino, cyano, azido, hydrazone, alkyl, alkenyl, alkynyl, alkoxy, aryl, heteroaryl, alkylaryl, alkylheteroaryl, cycloalkyl alkylcycloalkyl, heterocycloalkyl, alkylheterocycloalkyl, alkylthio, alkylsulfinyl, alkylsulfonyl, alkylamino, dialkylamino, alkylcarbonyl, alkoxycarbonyl, alkylaminocarbonyl, dialkylaminocarbonyl, peptidyl, polyamino, or polyalkyleneoxy.

In Formula IV, A can be any heterocyclic ring comprising a tertiary nitrogen atom. In some embodiments, A can be a heteroaromatic ring. In some embodiments, A can comprise one or more additional heteroatoms in addition to the tertiary nitrogen atom (e.g., one or more additional nitrogen atoms, one or more oxygen atoms, one or more sulfur atoms, or a combination thereof). For example, A can be chosen from pyridine, imidazole, pyrazole, triazole, tetrazole, oxazole, isoxazole, furazan, isothioazole, and thiazole. In certain embodiments, A can represent a pyridine ring.

In some embodiments of Formula IV, Y can be absent (i.e., the two heterocyclic rings can be bound directly to one another). In other embodiments, Y is present. When present, the linking group can be any suitable group or moiety which is at minimum bivalent, and connects the heterocyclic rings in the nucleophile. The linking group can be composed of any assembly of atoms, including oligomeric and polymeric chains. In some cases, the total number of atoms in the linking group can be from 3 to 200 atoms (e.g., from 3 to 150 atoms, from 3 to 100 atoms, from 3 and 50 atoms, from 3 to 25 atoms, from 3 to 15 atoms, or from 3 to 10 atoms). In some embodiments, the linking group can be, for example, an alkyl, alkoxy, alkylaryl, alkylheteroaryl, alkylcycloalkyl, alkylheterocycloalkyl, alkylthio, alkylsulfinyl, alkylsulfonyl, alkylamino, dialkylamino, alkylcarbonyl, alkoxycarbonyl, alkylaminocarbonyl, dialkylaminocarbonyl, or polyamino group. In some embodiments, the linking group can comprises one of the groups above joined to each of the heterocyclic rings by a functional group. Examples of suitable functional groups include, for example, secondary amides (—CONH—), tertiary amides (—CONR—), secondary carbamates (—OCONH—; —NHCOO—), tertiary carbamates (—OCONR—; —NRCOO—), ureas (—NHCONH—; —NRCONH—; —NHCONR—, or —NRCONR—), carbinols (—CHOH—, —CROH—), ethers (—O—), and esters (—COO—, —CH$_2$O$_2$C—, CHRO$_2$C—), wherein R is an alkyl group, an aryl group, or a heterocyclic group. For example, in some embodiments, the linking group can comprise an alkyl group (e.g., a $C_1$-$C_{12}$ alkyl group, a $C_1$-$C_8$ alkyl group, or a $C_1$-$C_6$ alkyl group) bound to each heterocyclic ring via an ester (—COO—, —CH$_2$O$_2$C—, CHRO$_2$C—), a secondary amide (—CONH—), or a tertiary amide (—CONR—), wherein R is an alkyl group, an aryl group, or a heterocyclic group.

In some embodiments of Formula IV, $R^1$ can be absent. In other embodiments, $R^1$ can be present. When present, $R^1$ can comprise a halogen, hydroxy, amino, cyano, azido, hydrazone, alkyl, alkenyl, alkynyl, alkoxy, aryl, heteroaryl, alkylaryl, alkylheteroaryl, cycloalkyl alkylcycloalkyl, heterocycloalkyl, alkylheterocycloalkyl, alkylthio, alkylsulfinyl, alkylsulfonyl, alkylamino, dialkylamino, alkylcarbonyl, alkoxycarbonyl, alkylaminocarbonyl, dialkylaminocarbonyl, peptidyl, polyamino, or polyalkyleneoxy group.

In some embodiments of Formula IV, $R^1$ can comprise a cationic group. In certain embodiments, the cationic group can comprise a cationic polyamino group (e.g., a polyethyleneimine segment). In other embodiments, the cationic group can comprise a cationic peptidyl group. In other embodiments, the cationic group can comprise a moiety (e.g., an alkyl group or an alkylaryl group) substituted with a cationic substituent, such as an ammonium group (e.g., a tetraalkylammonium group, an aryltrialkylammonium group, a diaryldialkylammonium group, or a triarylalkylammonium group) or a pyridinium group.

In some embodiments of Formula IV, $R^1$ can comprise a hydrophobic group. For example, in certain embodiments, $R^1$ can comprise an aryl group or an alkylaryl group. In some embodiments, $R^1$ can comprise a hydrophilic group. For example, in certain embodiments, $R^1$ can comprise a hydrophilic polyalkyleneoxy group (e.g., a polyethylene oxide segment).

In some embodiments of Formula IV, $R^1$ can comprise a reactive functional group, such as an olefin, acetylene, alcohol, phenol, ether, oxide, halide, aldehyde, ketone, carboxylic acid, ester, amide, cyanate, isocyanate, thiocyanate, isothiocyanate, amine, hydrazine, hydrazone, hydrazide, diazo, diazonium, nitro, nitrile, mercaptan, sulfide, disulfide, sulfoxide, sulfone, sulfonic acid, sulfinic acid, acetal, ketal, anhydride, sulfate, sulfenic acid isonitrile, amidine, imide, imidate, nitrone, hydroxylamine, oxime, hydroxamic acid, thiohydroxamic acid, allene, ortho ester, sulfite, enamine, ynamine, urea, pseudourea, semicarbazide, carbodiimide, carbamate, imine, azide, azo group, azoxy group, nitroso group, N-hydroxysuccinimide ester, or maleimides. For example, in certain embodiments, $R^1$ can comprise an alkynyl group or an azido group. In other embodiments, $R^1$ can comprise a hydrazone group.

In some embodiments, the polycation polymer can be a polymer defined by Formula I below

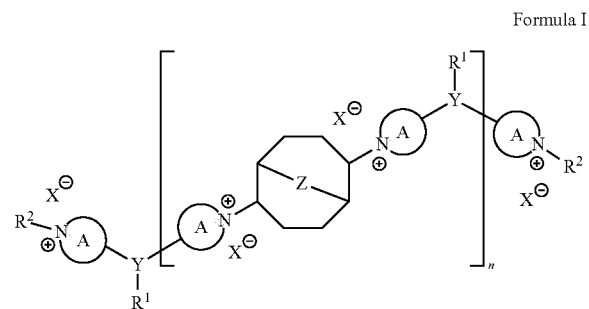

Formula I wherein Z represents, individually for each occurrence within the polymer, S, Se, or $NR^3$; A represents, individually for each occurrence within the polymer, a heterocyclic ring comprising a cationic nitrogen center; X represents, individually for each occurrence within the polymer, an anion; Y is absent, or represents, individually for each occurrence within the polymer, a linking group; $R^1$ is absent, or represents, individually for each occurrence within the polymer, halogen, hydroxy, amino, cyano, azido, hydrazone, alkyl, alkenyl, alkynyl, alkoxy, aryl, heteroaryl, alkylaryl, alkylheteroaryl, cycloalkyl alkylcycloalkyl, heterocycloalkyl, alkylheterocycloalkyl, alkylthio, alkylsulfinyl, alkylsulfonyl, alkylamino, dialkylamino, alkylcarbonyl, alkoxycarbonyl, alkylaminocarbonyl, dialkylaminocarbonyl, peptidyl, polyamino, or polyalkyleneoxy; $R^2$ is absent, or represents, individually for each occurrence within the polymer, alkyl, alkenyl, alkynyl, alkoxy, aryl, heteroaryl, alkylaryl, alkylheteroaryl, cycloalkyl alkylcycloalkyl, heterocycloalkyl, alkylheterocycloalkyl, peptidyl, polyamino, or polyalkyleneoxy; $R^3$ represents, individually for each occurrence within the polymer, alkyl, alkenyl, alkynyl, alkoxy, aryl, heteroaryl, alkylaryl, alkylheteroaryl, cycloalkyl alkylcycloalkyl, heterocycloalkyl, alkylheterocycloalkyl, peptidyl, polyamino, or polyalkyleneoxy; and n is an integer from 2 to 400.

In Formula I, A can be any heterocyclic ring comprising a tertiary nitrogen atom. In some embodiments, A can be a heteroaromatic ring. In some embodiments, A can comprise one or more additional heteroatoms in addition to the tertiary nitrogen atom (e.g., one or more additional nitrogen atoms, one or more oxygen atoms, one or more sulfur atoms, or a combination thereof). For example, A can be chosen from pyridine, imidazole, pyrazole, triazole, tetrazole, oxazole, isoxazole, furazan, isothioazole, and thiazole. In certain embodiments, A can represent a pyridine ring. In these embodiments, the polycation can be defined by Formula IA below

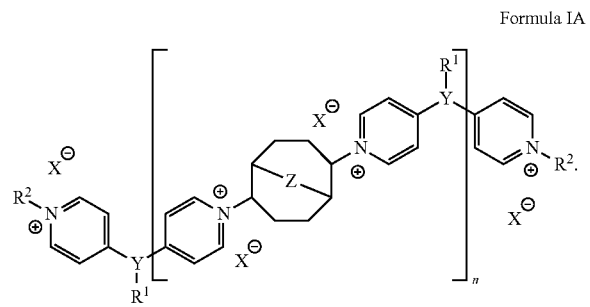

Formula IA

In some embodiments of Formula I and Formula IA, Z can be S. In other embodiments, Z can be $NR^3$.

In some embodiments of Formula I and Formula IA, Z can be $NR^3$, and $R^3$ can comprise a cationic group. For example, in certain embodiments, the cationic group can comprise a cationic polyamino group (e.g., a polyethyleneimine segment). In other embodiments, the cationic group can comprise a cationic peptidyl group. In other embodiments, the cationic group can comprise a moiety (e.g., an alkyl group or an alkylaryl group) substituted with a cationic substituent, such as an ammonium group (e.g., a tetraalkylammonium group, an aryltrialkylammonium group, a diaryldialkylammonium group, or a triarylalkylammonium group) or a pyridinium group.

In some embodiments of Formula I and Formula IA, Z can be $NR^3$, and $R^3$ can comprise a hydrophobic group. For example, in certain embodiments, Z can be $NR^3$, and $R^3$ can comprise an aryl group or an alkylaryl group.

In some embodiments of Formula I and Formula IA, Z can be $NR^3$, and $R^3$ can comprise a hydrophilic group. For example, in certain embodiments, Z can be $NR^3$, and $R^3$ can comprise a hydrophilic polyalkyleneoxy group (e.g., a polyethylene oxide segment).

In some embodiments of Formula I and Formula IA, Z can be $NR^3$, and $R^3$ can comprise a reactive functional group, such as an olefin, acetylene, alcohol, phenol, ether, oxide, halide, aldehyde, ketone, carboxylic acid, ester, amide, cyanate, isocyanate, thiocyanate, isothiocyanate, amine, hydrazine, hydrazone, hydrazide, diazo, diazonium, nitro, nitrile, mercaptan, sulfide, disulfide, sulfoxide, sulfone, sulfonic acid, sulfinic acid, acetal, ketal, anhydride, sulfate, sulfenic acid isonitrile, amidine, imide, imidate, nitrone, hydroxylamine, oxime, hydroxamic acid, thiohydroxamic acid, allene, ortho ester, sulfite, enamine, ynamine, urea, pseudourea, semicarbazide, carbodiimide, carbamate, imine, azide, azo group, azoxy group, nitroso group, N-hydroxysuccinimide ester, or maleimides. For example, in certain embodiments, $R^3$ can comprise an alkynyl group or an azido group. In other embodiments, $R^3$ can comprise a hydrazone group.

In Formula I and Formula IA, X can comprise any suitable, stable anion. By way of example, X can be chosen from chloride, bromide, iodide, nitrate, sulfate, triflate, borate, and phosphate.

In some embodiments of Formula I and Formula IA, Y can be absent (i.e., the two heterocyclic rings can be bound directly to one another). In other embodiments, Y is present. When present, the linking group can be any suitable group or moiety which is at minimum bivalent, and connects the heterocyclic rings in the nucleophile. The linking group can be composed of any assembly of atoms, including oligomeric and polymeric chains. In some cases, the total number of atoms in the linking group can be from 3 to 200 atoms (e.g., from 3 to 150 atoms, from 3 to 100 atoms, from 3 and 50 atoms, from 3 to 25 atoms, from 3 to 15 atoms, or from 3 to 10 atoms). In some embodiments, the linking group can be, for example, an alkyl, alkoxy, alkylaryl, alkylheteroaryl, alkylcycloalkyl, alkylheterocycloalkyl, alkylthio, alkylsulfinyl, alkylsulfonyl, alkylamino, dialkylamino, alkylcarbonyl, alkoxycarbonyl, alkylaminocarbonyl, dialkylaminocarbonyl, or polyamino group. In some embodiments, the linking group can comprises one of the groups above joined to each of the heterocyclic rings by a functional group. Examples of suitable functional groups include, for example, secondary amides (—CONH—), tertiary amides (—CONR—), secondary carbamates (—OCONH—; —NHCOO—), tertiary carbamates (—OCONR—; —NRCOO—), ureas (—NHCONH—; —NRCONH—; —NHCONR—, or —NRCONR—), carbinols (—CHOH—, —CROH—), ethers (—O—), and esters (—COO—, —CH$_2$O$_2$C—, CHRO$_2$C—), wherein R is an alkyl group, an aryl group, or a heterocyclic group. For example, in some embodiments, the linking group can comprise an alkyl group (e.g., a C$_1$-C$_{12}$ alkyl group, a C$_1$-C$_8$ alkyl group, or a C$_1$-C$_6$ alkyl group) bound to each heterocyclic ring via an ester (—COO—, —CH$_2$O$_2$C—, CHRO$_2$C—), a secondary amide (—CONH—), or a tertiary amide (—CONR—), wherein R is an alkyl group, an aryl group, or a heterocyclic group. In certain embodiments, Y can be chosen from one of the following:

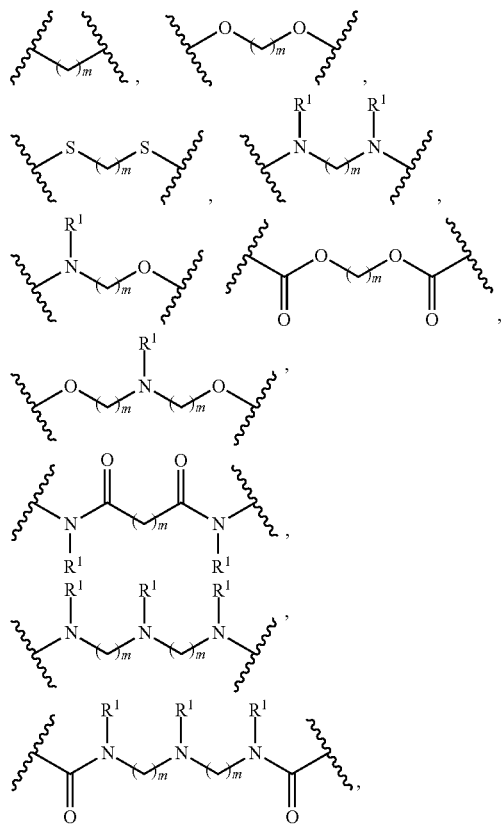

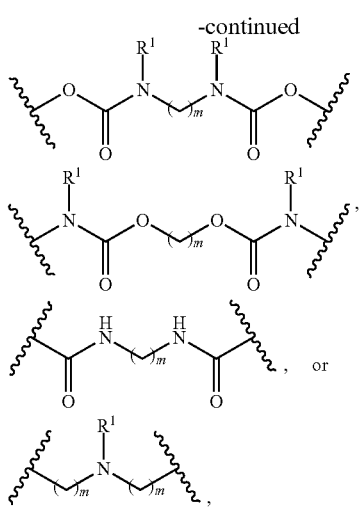

where m is an integer from 1 to 12.

In some embodiments of Formula I and Formula IA, $R^1$ can be absent. In other embodiments, $R^1$ can be present. When present, $R^1$ can comprise a halogen, hydroxy, amino, cyano, azido, hydrazone, alkyl, alkenyl, alkynyl, alkoxy, aryl, heteroaryl, alkylaryl, alkylheteroaryl, cycloalkyl alkylcycloalkyl, heterocycloalkyl, alkylheterocycloalkyl, alkylthio, alkylsulfinyl, alkylsulfonyl, alkylamino, dialkylamino, alkylcarbonyl, alkoxycarbonyl, alkylaminocarbonyl, dialkylaminocarbonyl, peptidyl, polyamino, or polyalkyleneoxy group.

In some embodiments of Formula I and Formula IA, $R^1$ can comprise a cationic group. In certain embodiments, the cationic group can comprise a cationic polyamino group (e.g., a polyethyleneimine segment). In other embodiments, the cationic group can comprise a cationic peptidyl group. In other embodiments, the cationic group can comprise a moiety (e.g., an alkyl group or an alkylaryl group) substituted with a cationic substituent, such as an ammonium group (e.g., a tetraalkylammonium group, a aryltrialkylammonium group, a diaryldialkylammonium group, or a triarylalkylammonium group) or a pyridinium group.

In some embodiments of Formula I and Formula IA, $R^1$ can comprise a hydrophobic group. For example, in certain embodiments, $R^1$ can comprise an aryl group or an alkylaryl group. In some embodiments, $R^1$ can comprise a hydrophilic group. For example, in certain embodiments, $R^1$ can comprise a hydrophilic polyalkyleneoxy group (e.g., a polyethylene oxide segment).

In some embodiments of Formula I and Formula IA, $R^1$ can comprise a reactive functional group, such as an olefin, acetylene, alcohol, phenol, ether, oxide, halide, aldehyde, ketone, carboxylic acid, ester, amide, cyanate, isocyanate, thiocyanate, isothiocyanate, amine, hydrazine, hydrazone, hydrazide, diazo, diazonium, nitro, nitrile, mercaptan, sulfide, disulfide, sulfoxide, sulfone, sulfonic acid, sulfinic acid, acetal, ketal, anhydride, sulfate, sulfenic acid isonitrile, amidine, imide, imidate, nitrone, hydroxylamine, oxime, hydroxamic acid, thiohydroxamic acid, allene, ortho ester, sulfite, enamine, ynamine, urea, pseudourea, semicarbazide, carbodiimide, carbamate, imine, azide, azo group, azoxy group, nitroso group, N-hydroxysuccinimide ester, or maleimides. For example, in certain embodiments, $R^1$ can comprise an alkynyl group or an azido group. In other embodiments, $R^1$ can comprise a hydrazone group.

In some embodiments of Formula I and Formula IA, $R^2$ can be absent. In other embodiments, $R^2$ can be present. When present, $R^2$ can comprise an alkyl, alkenyl, alkynyl, alkoxy, aryl, heteroaryl, alkylaryl, alkylheteroaryl, cycloalkyl alkylcycloalkyl, heterocycloalkyl, alkylheterocycloalkyl, peptidyl, polyamino, or polyalkyleneoxy In some embodiments of Formula I and Formula IA, $R^2$ can comprise a cationic group. In certain embodiments, the cationic group can comprise a cationic polyamino group (e.g., a polyethyleneimine segment). In other embodiments, the cationic group can comprise a cationic peptidyl group. In other embodiments, the cationic group can comprise a moiety (e.g., an alkyl group or an alkylaryl group) substituted with a cationic substituent, such as an ammonium group (e.g., a tetraalkylammonium group, an aryltrialkylammonium group, a diaryldialkylammonium group, or a triarylalkylammonium group) or a pyridinium group.

In some embodiments of Formula I and Formula IA, $R^2$ can comprise a hydrophobic group. For example, in certain embodiments, $R^2$ can comprise an aryl group or an alkylaryl group. In some embodiments, $R^2$ can comprise a hydrophilic group. For example, in certain embodiments, $R^2$ can comprise a hydrophilic polyalkyleneoxy group (e.g., a polyethylene oxide segment).

In some embodiments of Formula I and Formula IA, $R^2$ can comprise a reactive functional group, such as an olefin, acetylene, alcohol, phenol, ether, oxide, halide, aldehyde, ketone, carboxylic acid, ester, amide, cyanate, isocyanate, thiocyanate, isothiocyanate, amine, hydrazine, hydrazone, hydrazide, diazo, diazonium, nitro, nitrile, mercaptan, sulfide, disulfide, sulfoxide, sulfone, sulfonic acid, sulfinic acid, acetal, ketal, anhydride, sulfate, sulfenic acid isonitrile, amidine, imide, imidate, nitrone, hydroxylamine, oxime, hydroxamic acid, thiohydroxamic acid, allene, ortho ester, sulfite, enamine, ynamine, urea, pseudourea, semicarbazide, carbodiimide, carbamate, imine, azide, azo group, azoxy group, nitroso group, N-hydroxysuccinimide ester, or maleimides. For example, in certain embodiments, $R^2$ can comprise an alkynyl group or an azido group. In other embodiments, $R^2$ can comprise a hydrazone group.

In some embodiments of Formula I and Formula IA, n can be at least 2 (e.g., at least 5, at least 10, at least 15, at least 20, at least 25, at least 30, at least 40, at least 50, at least 60, at least 70, at least 80, at least 90, at least 100, at least 110, at least 120, at least 130, at least 140, at least 150, at least 160, at least 170, at least 180, at least 190, at least 200, at least 225, at least 250, at least 275, at least 300, at least 325, at least 350, or at least 375). In some embodiments, n can be 400 or less (e.g., 375 or less, 350 or less, 325 or less, 300 or less, 275 or less, 250 or less, 225 or less, 200 or less, 190 or less, 180 or less, 170 or less, 160 or less, 150 or less, 140 or less, 130 or less, 120 or less, 110 or less, 100 or less, 90 or less, 80 or less, 70 or less, 60 or less, 50 or less, 40 or less, 30 or less, 25 or less, 20 or less, 15 or less, 10 or less, or 5 or less).

n can range from any of the minimum values described above to any of the maximum values described above. For example, n can range from 2 to 400 (e.g., from 2 to 200, from 2 to 100, from 2 to 50, from 5 to 400, from 5 to 200, from 5 to 100, or from 5 to 50).

In other cases, the polycationic polymer can be formed by polymerization of monomers (e.g., acrylate monomers) containing pendant cyclic bis-electrophiles (e.g., pendant versions of the cyclic bis-electrophiles defined by Formula IIA, Formula JIB, or Formula IIC where Z is $NR^3$, and $R^3$ represents an acrylate group connected to the cyclic bis-electrophile via a linking group). Following polymerization, the pendant cyclic bis-electrophiles can be reacted with nucleophiles to introduce positively charged centers within the polymer sidechains.

By way of example, also provided are polycationic polymers comprising a recurring unit defined by Formula V below

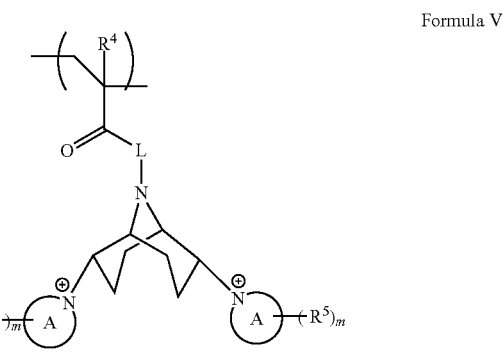

Formula V wherein $R^4$ represents H or methyl; L is absent or represents a linking group; A represents, individually for each occurrence, a heterocyclic ring comprising a cationic nitrogen center; $R^5$ is absent, or represents, individually for each occurrence, halogen, hydroxy, amino, cyano, azido, hydrazone, alkyl, alkenyl, alkynyl, alkoxy, aryl, heteroaryl, alkylaryl, alkylheteroaryl, cycloalkyl alkylcycloalkyl, heterocycloalkyl, alkylheterocycloalkyl, alkylthio, alkylsulfinyl, alkylsulfonyl, alkylamino, dialkylamino, alkylcarbonyl, alkoxycarbonyl, alkylaminocarbonyl, dialkylaminocarbonyl, peptidyl, polyamino, or polyalkyleneoxy; and m is an integer from 0 to 5.

In some embodiments, L can be absent. In other embodiments, L is present and represents a linking group. When present, the linking group can be any suitable group or moiety which is at minimum bivalent, and connects the pendant 9-azabicyclo[3.3.1]nonyl moiety to the polymer backbone. The linking group can be composed of any assembly of atoms, including oligomeric and polymeric chains. In some cases, the total number of atoms in the linking group can be from 3 to 200 atoms (e.g., from 3 to 150 atoms, from 3 to 100 atoms, from 3 and 50 atoms, from 3 to 25 atoms, from 3 to 15 atoms, or from 3 to 10 atoms). In some embodiments, the linking group can be, for example, an alkyl, alkoxy, alkylaryl, alkylheteroaryl, alkylcycloalkyl, alkylheterocycloalkyl, alkylthio, alkylsulfinyl, alkylsulfonyl, alkylamino, dialkylamino, alkylcarbonyl, alkoxycarbonyl, alkylaminocarbonyl, dialkylaminocarbonyl, or polyamino group.

In Formula V, A can be any heterocyclic ring comprising a tertiary nitrogen atom. In some embodiments, A can be a heteroaromatic ring. In some embodiments, A can comprise one or more additional heteroatoms in addition to the tertiary nitrogen atom (e.g., one or more additional nitrogen atoms, one or more oxygen atoms, one or more sulfur atoms, or a combination thereof). For example, A can be chosen from pyridine, imidazole, pyrazole, triazole, tetrazole, oxazole, isoxazole, furazan, isothioazole, and thiazole. In certain embodiments, A can represent a pyridine ring.

In some embodiments, $R^5$ can be absent. In other embodiments, $R^5$ can be present. When present, $R^5$ can comprise, individually for each occurrence, a halogen, hydroxy, amino, cyano, azido, hydrazone, alkyl, alkenyl, alkynyl, alkoxy, aryl, heteroaryl, alkylaryl, alkylheteroaryl, cycloalkyl alkylcycloalkyl, heterocycloalkyl, alkylheterocycloalkyl, alkylthio, alkylsulfinyl, alkylsulfonyl, alkylamino, dialkylamino, alkylcarbonyl, alkoxycarbonyl, alkylaminocarbonyl, dialkylaminocarbonyl, peptidyl, polyamino, or polyalkyleneoxy group.

In some embodiments, $R^5$ can comprise a cationic group. In certain embodiments, the cationic group can comprise a cationic polyamino group (e.g., a polyethyleneimine segment). In other embodiments, the cationic group can comprise a cationic peptidyl group. In other embodiments, the cationic group can comprise a moiety (e.g., an alkyl group or an alkylaryl group) substituted with a cationic substituent, such as an ammonium group (e.g., a tetraalkylammonium group, a aryltrialkylammonium group, a diaryldialkylammonium group, or a triarylalkylammonium group) or a pyridinium group.

In some embodiments, $R^5$ can comprise a hydrophobic group. For example, in certain embodiments, $R^5$ can comprise an aryl group or an alkylaryl group. In some embodiments, $R^5$ can comprise a hydrophilic group. For example, in certain embodiments, $R^5$ can comprise a hydrophilic polyalkyleneoxy group (e.g., a polyethylene oxide segment).

In some embodiments, $R^5$ can comprise a reactive functional group, such as an olefin, acetylene, alcohol, phenol, ether, oxide, halide, aldehyde, ketone, carboxylic acid, ester, amide, cyanate, isocyanate, thiocyanate, isothiocyanate, amine, hydrazine, hydrazone, hydrazide, diazo, diazonium, nitro, nitrile, mercaptan, sulfide, disulfide, sulfoxide, sulfone, sulfonic acid, sulfinic acid, acetal, ketal, anhydride, sulfate, sulfenic acid isonitrile, amidine, imide, imidate, nitrone, hydroxylamine, oxime, hydroxamic acid, thiohydroxamic acid, allene, ortho ester, sulfite, enamine, ynamine, urea, pseudourea, semicarbazide, carbodiimide, carbamate, imine, azide, azo group, azoxy group, nitroso group, N-hydroxysuccinimide ester, or maleimides. For example, in certain embodiments, $R^5$ can comprise an alkynyl group or an azido group. In other embodiments, $R^5$ can comprise a hydrazone group.

In some embodiments, the polycationic polymer can further comprise a recurring unit derived from the polymerization of one or more ethylenically-unsaturated monomers. Example ethylenically-unsaturated monomers include (meth)acrylate monomers, vinyl aromatic monomers (e.g., styrene), ethylenically unsaturated aliphatic monomers (e.g., butadiene), vinyl ester monomers (e.g., vinyl acetate), (meth)acrylonitrile monomers, vinyl halide monomers, vinyl ether monomers, silane-containing monomers, (meth)acrylamide monomers (as well as (meth)acrylamide derivatives), sulfur-based monomers, and combinations thereof.

Exemplary acrylate and (meth)acrylate monomers include, but are not limited to, methyl acrylate, methyl (meth)acrylate, ethyl acrylate, ethyl (meth)acrylate, butyl acrylate, butyl (meth)acrylate, isobutyl (meth)acrylate, n-hexyl (meth)acrylate, ethylhexyl (meth)acrylate, n-heptyl (meth)acrylate, ethyl (meth)acrylate, 2-methylheptyl (meth) acrylate, octyl (meth)acrylate, isooctyl (meth)acrylate, n-nonyl (meth)acrylate, isononyl (meth)acrylate, n-decyl (meth)acrylate, isodecyl (meth)acrylate, dodecyl (meth) acrylate, lauryl (meth)acrylate, tridecyl (meth)acrylate, stearyl (meth)acrylate, glycidyl (meth)acrylate, alkyl crotonates, vinyl acetate, di-n-butyl maleate, di-octylmaleate, acetoacetoxyethyl (meth)acrylate, acetoacetoxypropyl (meth)acrylate, hydroxyethyl (meth)acrylate, allyl (meth) acrylate, tetrahydrofurfuryl (meth)acrylate, cyclohexyl (meth)acrylate, 2-ethoxyethyl (meth)acrylate, 2-methoxy (meth)acrylate, 2-(2-ethoxyethoxy)ethyl (meth)acrylate, 2-ethylhexyl (meth)acrylate, 2-propylheptyl (meth)acrylate, 2-phenoxyethyl (meth)acrylate, isobornyl (meth)acrylate, caprolactone (meth)acrylate, polypropyleneglycol mono (meth)acrylate, polyethyleneglycol (meth)acrylate, benzyl (meth)acrylate, 2,3-di(acetoacetoxy)propyl (meth)acrylate, hydroxypropyl (meth)acrylate, methylpolyglycol (meth) acrylate, 3,4-epoxycyclohexylmethyl (meth)acrylate, 1,6 hexanediol di(meth)acrylate, 1,4 butanediol di(meth)acrylate and combinations thereof.

Suitable vinyl aromatic compounds include styrene, α- and p-methylstyrene, α-butylstyrene, 4-n-butylstyrene, 4-n-decylstyrene, vinyltoluene, and combinations thereof. Vinyl esters of carboxylic acids include, for example, vinyl laurate, vinyl stearate, vinyl propionate, versatic acid vinyl esters, vinyl acetate, and combinations thereof. The vinyl halides can include ethylenically unsaturated compounds substituted by chlorine, fluorine or bromine, such as vinyl chloride and vinylidene chloride. The vinyl ethers can include, for example, vinyl ethers of alcohols comprising 1 to 4 carbon atoms, such as vinyl methyl ether or vinyl isobutyl ether. Aliphatic hydrocarbon monomers can include, for example, hydrocarbons having 4 to 8 carbon atoms and two olefinic double bonds, such as butadiene, isoprene, and chloroprene. Silane containing monomers can include, for example, vinyl silanes, such as vinyltrimethoxysilane, vinyltriethoxysilane (VTEO), vinyl tris(2-methoxyethoxysilane), and vinyl triisopropoxysilane, and (meth)acrylatoalkoxysilanes, such as (meth)acryloyloxypropyltrimethoxysilane, γ-(meth)acryloxypropyltrimethoxysilane, and γ-(meth)acryloxypropyltriethoxysilane. (Meth)acrylamide derivatives include, for example, keto-containing amide functional monomers defined by the general structure below

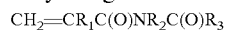

$CH_2=CR_1C(O)NR_2C(O)R_3$ wherein $R_1$ is hydrogen or methyl; $R_2$ is hydrogen, a $C_1$-$C_4$ alkyl group, or a phenyl group; and $R_3$ is hydrogen, a $C_1$-$C_4$ alkyl group, or a phenyl group. For example, the (meth) acrylamide derivative can be diacetone acrylamide (DAAM) or diacetone methacrylamide. Sulfur-containing monomers include, for example, sulfonic acids and sulfonates, such as vinylsulfonic acid, 2-sulfoethyl methacrylate, sodium styrenesulfonate, 2-sulfoxyethyl methacrylate, vinyl butylsulfonate, sulfones such as vinylsulfone, sulfoxides such as vinylsulfoxide, and sulfides such as 1-(2-hydroxyethylthio) butadiene.

Also provided are methods of making polycationic polymers. Methods of making polycationic polymers can comprise contacting a bicyclononane monomer defined by Formula II above with a polynucleophilic monomer can be defined by Formula III above. In some embodiments, this can comprise combining a bicyclononane monomer defined by Formula II above with a polynucleophilic monomer can be defined by Formula III above in a polar aprotic solvent (e.g., acetonitrile).

By way of non-limiting illustration, examples of certain embodiments of the present disclosure are given below.

EXAMPLES

Example 1: Fragmentable Polycationic Materials Based on Anchimeric Assistance

New modular, fragmentable oligo- and polycations have been developed based on the reactions of 9-thiabicyclo [3.3.1]dichloride and related compounds with substituted dipyridyl nucleophiles by an anchimeric assistance mechanism. Each bond-forming event in this condensation polymerization process generates a positive charge in the main chain. Product lengths were found to be dependent on the reactivity of the electrophile, which was tunable by changing the nature of the leaving group β to sulfur. The monomers were easily synthesized, and the resulting readily available polymers were found to be highly efficient binders of nucleic acid. The polycations also exhibited properties of cytotoxicity and DNA transfection with interesting structure-activity characteristics. The polycations decomposed by hydrolysis at rates dependent on the leaving-group ability of the pyridyl unit, which correlated roughly with the $pK_a$ of its conjugate acid. Polymer decomposition occurs simultaneously throughout the length of the chains, rather than from the ends; the decomposition products were tested and found to be only minimally toxic to cultured cells Background The reliable substitution chemistry of 9-thiabicyclo[3.3.1] dichloride (1) and related electrophiles was first described almost 40 years ago by the Weil, Corey, and Lautenschlaeger group (resulting in the designation of 1 as a "WCL" building block). The reactivity of this scaffold has been explored for its fast and clean nature due to anchimeric assistance provided by the internal nucleophilic center. As with other reactions meeting the click chemistry standard, such reactions can potentially be used in materials science applications. Substitution chemistry accelerated by neighboring group participation has been used intermittently for many years in polymer synthesis and modification, although sometimes intramolecular effects have been mistaken for true anchimeric assistance.

Cationic polymers are of interest primarily for gene delivery and surface antimicrobial properties, with recent attention to new designs and precise control of structure-property relationships. The majority of such materials employ primary, secondary, and tertiary amines that require protonation to carry the desired charges. Polyethylenimine (PEI), synthesized by the ring opening polymerization of aziridine, is a popular example. Cleavable linkages such as esters, acetals/ketals, imines, and disulfides have been employed in constructing biodegradable transfection agents from branched PEI, often with the sacrifice of a unit positive charge at each point of linker connection. Permanently charged species such as quaternary ammonium or pyridinium ions are only rarely employed as linkages in the backbone of polycationic chains, although they have been used to modify polymer branches and are the predominant positively-charged constituents of cationic lipid head groups used as small-molecule transfection reagents. An example are the polyionenes usually synthesized by $S_N2$ Menschutkin reaction at comparatively high temperatures. The resulting materials show properties characteristic of other polycations, but are thermally and chemically stable at physiological temperature, and are therefore not biodegradable.

In this example, the use of WCL electrophiles in the synthesis of a new class of polycationic molecules that have a unique architecture and mode of fragmentation are described. The polycationic materials are represented schematically in Scheme 1. In these systems, positive charge is created by each substitution event and disappears when the linkage fragments in the course of anchimerically-assisted hydrolysis, rather than being carried by monomers, so the starting materials and products are uncharged (except for byproduct mineral acid). Preliminary characterization of the cytotoxic and DNA transfection properties of the polycations are also described, and demonstrate that this class of materials may be suitable for antimicrobial and gene delivery applications.

Scheme 1. Schematic representation of WCL-based condensation polymerization and depolymerization, both processes taking place via anchimeric assistance.

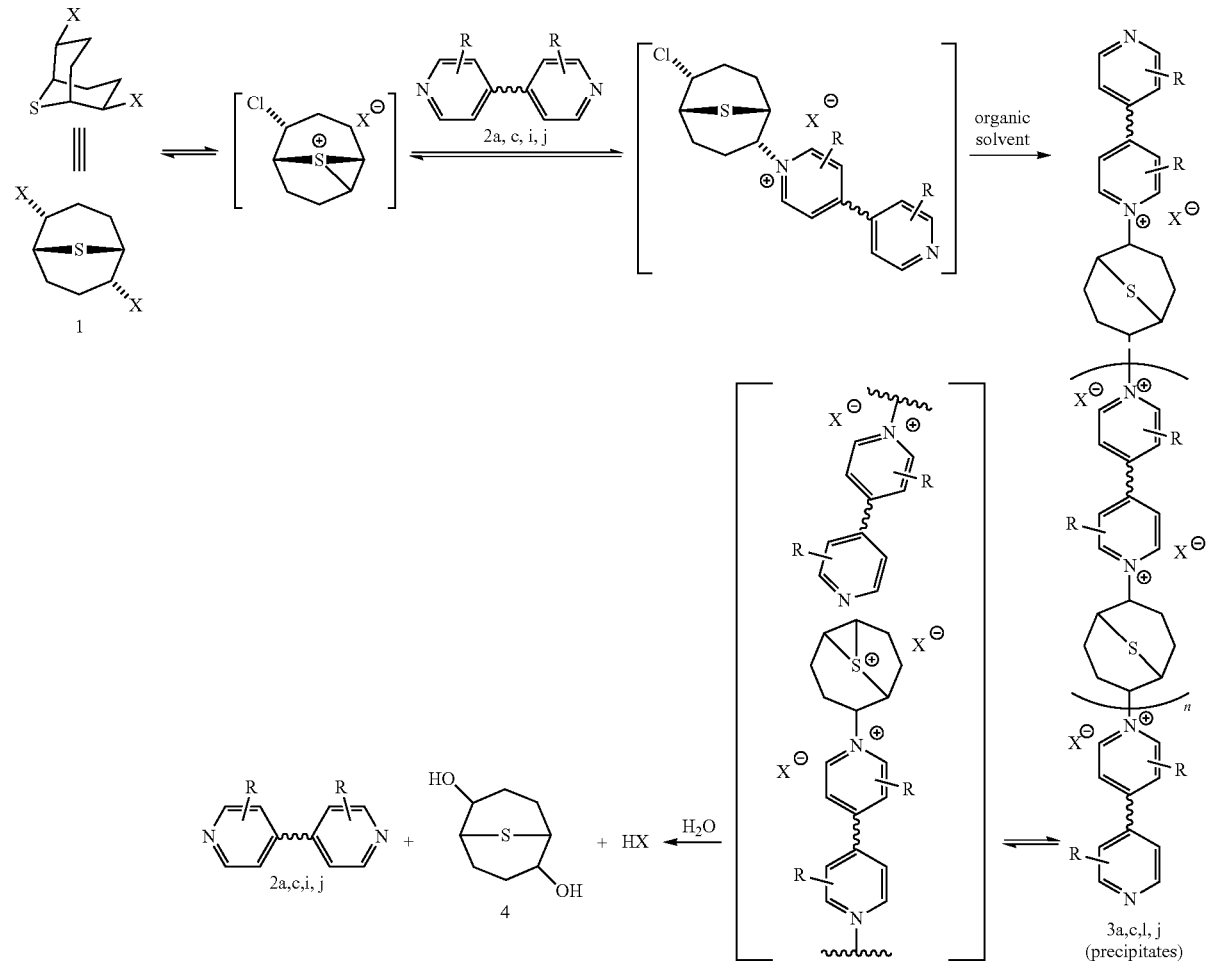

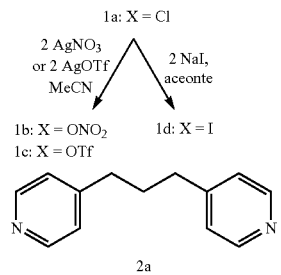

Materials and Methods

Reagents and solvents were purchased from commercial sources and used as received, unless otherwise stated. When dry solvents were required, solvents were passed through activated alumina columns on an MBraun solvent purification system (MB-SPS), and collected in oven-dried glassware prior to use. Water was purified on a Millipore Milli-Q Advantage A10 system. Unless otherwise stated, the reactions were performed under inert atmosphere in capped reaction vessels. Flash chromatography was performed on 60-mesh silica. Analytical TLC was performed on aluminum-backed plates and visualized by exposure to UV light and/or staining with aqueous potassium permanganate (2% $KMnO_4$+5% $K_2CO_3$).

Instrumentation

NMR spectra were obtained on Bruker AMX-400, and DRX-500 instruments in deuterated solvents (Cambridge Isotope Laboratories, Inc.) and referenced to the signals of residual protium in the NMR solvent. Spectra were processed in MestReNova software (Mestrelab Research). Routine mass spectra were obtained on an Advion Compact Mass Spectrometer (G1946D) ESI-MSD instrument, using direct sample injection followed with 9:1 $CH_3CN:H_2O$ containing 0.1% formic acid as mobile phase. Absorbance and fluorescence spectra were collected on a VarioskanFlash plate reader (ThermoFisher). Gel permeation chromatography (GPC) analysis was performed in DMF or Milli-Q water at 1 mL/min flow rate (LC-20AD pump) on a Shimadzu GPC setup equipped with two Phenomenex Phenogel 10 μm linear columns (300×7.8 mm) or PolySep-GFC-P (300×7.0 mm), autosampler (SIL-20A) and column oven (CTO-20A) set at 40° C. Detection was achieved using a diode array detector (SPD--M20A), and RI detector (RID--10A), and instrument was calibrated with polystyrene standards kits (Supelco) or Dextran kit (Phenomenex ALO-2772). Dynamic light scattering measurements were taken on a DynaPro plate reader and analyzed with Dynamics® software (Wyatt Technology, Santa Barbara, Calif.). Transmission electron microscope images were acquired on a Hitachi HT7700 microscope operated at 120 kV.

Synthetic Procedures and Characterization of New Compounds 2,6-Dichloro-9-thiabicyclo[3.3.1]nonane (1a) was synthesized using the methods described in Diaz, D. D. et al. "2,6-Dichloro-9-thiabicyclo[3.3.1]nonane: Multigram Display of Azide and Cyanide Components on a Versatile Scaffold," *Molecules*, 2006, 11, 212-218, which is hereby incorporated herein by reference. $^1$H NMR (400 MHz, $CDCl_3$) δ 4.71 (d, J=3.3 Hz, 2H), 2.85 (dd, J=6.8, 3.6 Hz, 2H), 2.72-2.61 (m, 2H), 2.36-2.18 (m, 6H). $^{13}$C NMR (126 MHz, $CDCl_3$) δ 62.34, 37.10, 32.40, 28.12.

2,6-Dinitro-9-thiabicyclo[3.3.1]nonane (1b). 1a (21 mg, 0.1 mmol, 1 equiv) and silver nitrate (34 mg, 0.2 mmol, 2 equiv) were mixed in 0.5 mL MeCN and stirred overnight at room temperature. The resulting AgCl was removed by centrifugation and the solvent was evaporated to give 1b as a colorless oil (22 mg, 86% yield). $^1$H NMR (400 MHz, $CDCl_3$) δ 5.66-5.50 (m, 2H), 3.02 (d, J=3.1 Hz, 2H), 2.51 (dd, J=14.5, 6.7 Hz, 2H), 2.32 (dd, J=9.8, 3.0 Hz, 2H), 2.20 (dt, J=13.5, 6.7 Hz, 2H), 2.11-1.92 (m, 2H). $^{13}$C NMR (101 MHz, $CDCl_3$) δ 82.24, 32.72, 26.92, 24.84.

2,6-Diiodo-9-thiabicyclo[3.3.1]nonane (1d). Compound 1a (252 mg, 1.2 mmol, 1 equiv) and sodium iodide (540 mg, 3.6 mmol, 3 equiv) were mixed in 6 mL acetone and stirred overnight at room temperature. NaCl was filtered off and the solution was evaporated. The resulting solid was dissolved in $CH_2Cl_2$, leaving behind excess sodium iodide. Evaporation of this solution gave 1d as a yellow powder (270 mg, 58% yield). $^1$H NMR (500 MHz, $CDCl_3$) δ 5.26-5.12 (m, 2H), 3.11 (t, J=3.4 Hz, 2H), 2.95-2.81 (m, 2H), 2.71 (ddd, J=11.6, 6.1, 4.0 Hz, 2H), 2.58-2.42 (m, 2H). $^{13}$C NMR (126 MHz, CDCl3) δ 38.50, 36.11, 35.75, 32.35.

Representative procedure for the synthesis of pyridine adducts of both small molecules and oligomers (Table 2, Table 3): Compound 1a (21 mg, 0.1 mmol, 1 equiv), silver nitrate (34 mg, 0.2 mmol, 2 equiv) and the pyridine of interest (0.2 mmol, 2 equiv) were mixed in 0.5 mL MeCN and stirred overnight at room temperature under inert atmosphere. The precipitate was collected and washed with MeCN. The charged adduct was dissolved in water and any remaining solids were removed by centrifugation, repeating the centrifugation step until the solution was not cloudy. The resulting solution was frozen and lyophilized to obtain the product as a colorless solid. 2,6-di-3-methoxycarbonylpyridinium-9-thiabicyclo[3.3.1]nonane dinitrate (5b): $^1$H NMR (400 MHz, $D_2O$) δ 9.58 (s, 2H), 9.35 (d, J=4.9 Hz, 2H), 9.23-9.08 (m, 2H), 8.47-8.27 (m, 2H), 5.85 (dd, J=8.3, 4.0 Hz, 2H), 3.41 (s, 2H), 3.25 (q, J=13.0 Hz, 2H), 2.49 (t, J=14.5 Hz, 4H), 2.36 (d, J=14.9 Hz, 2H). $^{13}$C NMR (126 MHz, $D_2O$) δ 163.09, 146.47, 146.01, 144.54, 131.16, 129.01, 74.35, 53.86, 35.67, 26.25, 24.27.

2,6-di-4-methoxycarbonylpyridinium-9-thiabicyclo[3.3.1]nonane dinitrate (5c): $^1$H NMR (400 MHz, $D_2O$) δ 9.31 (d, J=6.7 Hz, 4H), 8.65 (d, J=6.6 Hz, 4H), 5.92-5.77 (m, 2H), 3.40 (s, 2H), 3.19 (dd, J=12.9, 5.5 Hz, 2H), 2.60-2.43 (m, 4H), 2.43-2.31 (m, 2H). $^{13}$C NMR (126 MHz, $D_2O$) δ 163.50, 145.43, 144.84, 128.20, 74.39, 54.22, 35.92, 26.52, 24.68.

2,6-di-3-carbamylpyridinium-9-thiabicyclo[3.3.1]nonane dinitrate (5d): $^1$H NMR (400 MHz, $D_2O$) δ 9.47 (s, 2H), 9.28 (d, J=6.0 Hz, 2H), 8.98 (dd, J=16.1, 7.3 Hz, 2H), 8.48-8.28 (m, 2H), 5.94-5.74 (m, 2H), 3.41 (s, 2H), 3.36-3.13 (m, 2H), 2.66-2.40 (m, 4H), 2.36 (d, J=15.7 Hz, 2H). $^{13}$C NMR (101 MHz, $D_2O$) δ 165.66, 145.33, 144.82, 143.44, 134.42, 128.93, 74.42, 35.82, 26.42, 24.44.

2,6-di-4-carbamylpyridinium-9-thiabicyclo[3.3.1]nonane dinitrate (5e): $^1$H NMR (400 MHz, D$_2$O) δ 9.36 (d, J=6.8 Hz, 4H), 8.53 (d, J=6.7 Hz, 4H), 5.87 (dd, J=10.5, 6.7 Hz, 2H), 3.45 (d, J=2.7 Hz, 2H), 3.36-3.17 (m, 2H), 2.62-2.46 (m, 4H), 2.40 (dd, J=9.4, 6.4 Hz, 2H). $^{13}$C NMR (126 MHz, D$_2$O) δ 166.24, 149.13, 144.47, 126.79, 74.08, 35.78, 26.41, 24.59, 2,6-di-3-bromopyridinium-9-thiabicyclo[3.3.1]nonane dinitrate (5f): $^1$H NMR (400 MHz, D$_2$O) δ 9.33 (d, J=0.9 Hz, 2H), 9.10 (d, J=5.2 Hz, 2H), 8.93-8.72 (m, 2H), 8.11 (dd, J=8.3, 6.2 Hz, 2H), 5.90-5.61 (m, 2H), 3.34 (s, 2H), 3.13 (dd, J=13.0, 5.7 Hz, 2H), 2.58-2.25 (m, 6H). $^{13}$C NMR (126 MHz, D$_2$O) δ 149.30, 144.72, 141.88, 129.23, 123.63, 74.22, 35.83, 26.38, 24.27.

2,6-di-3-trifluoromethylpyridinium-9-thiabicyclo[3.3.1]nonane dinitrate (5g): $^1$H NMR (500 MHz, D$_2$O) δ 9.86 (s, 2H), 9.53 (d, J=6.4 Hz, 2H), 9.13 (d, J=8.1 Hz, 2H), 8.53-8.48 (m, 2H), 6.01-5.89 (m, 2H), 3.52 (d, J=2.4 Hz, 2H), 3.32 (dd, J=12.9, 6.2 Hz, 2H), 2.66-2.48 (m, 4H), 2.42 (dd, J=15.2, 4.3 Hz, 2H). $^{13}$C NMR (101 MHz, D$_2$O) δ 149.76, 147.21, 147.17, 129.58, 114.67, 113.24, 75.11, 35.64, 26.23, 24.36.

2,6-di-3-cyanopyridinium-9-thiabicyclo[3.3.1]nonane dinitrate (5h): $^1$H NMR (500 MHz, D$_2$O) δ 9.69 (s, 2H), 9.54 (d, J=6.3 Hz, 2H), 9.07 (d, J=8.2 Hz, 2H), 8.61-8.44 (m, 2H), 5.94 (dd, J=8.3, 3.7 Hz, 2H), 3.50 (d, J=3.0 Hz, 2H), 3.37 (dd, J=12.9, 6.4 Hz, 2H), 2.66-2.45 (m, 4H), 2.45-2.33 (m, 2H). $^{13}$C NMR (101 MHz, D$_2$O) δ 146.26 (s), 144.09 (d, J=3.0 Hz), 142.46 (d, J=4.0 Hz), 131.43 (q, J=36.5 Hz), 121.26 (q, J=273.2 Hz), 75.01 (s), 35.82 (s), 26.42 (s), 24.34 (s).

2,6-di-3-bromo-5-methoxylpyridinium-9-thiabicyclo[3.3.1]nonane dinitrate (5i): $^1$H NMR (400 MHz, D$_2$O) δ 9.00 (s, 2H), 8.87 (s, 2H), 8.49 (s, 2H), 5.79-5.63 (m, 2H), 3.41 (d, J=2.6 Hz, 2H), 3.27 (dd, J=13.0, 6.1 Hz, 2H), 2.49 (td, J=11.3, 6.4 Hz, 2H), 2.45-2.31 (m, 4H). $^{13}$C NMR (126 MHz, D$_2$O) δ 159.03, 135.88, 133.04, 131.50, 123.55, 74.47, 57.72, 35.92, 26.48, 24.03.

2,6-di-3-bromo-5-carbamylpyridinium-9-thiabicyclo[3.3.1]nonane ditriflate (5j): $^1$H NMR (500 MHz, D$_2$O) δ 9.47 (s, 2H), 9.41 (s, 2H), 9.17 (s, 2H), 5.77 (dd, J=8.4, 4.0 Hz, 2H), 3.37 (s, 2H), 3.19 (dd, J=13.1, 6.1 Hz, 2H), 2.46 (t, J=11.3 Hz, 2H), 2.38 (dd, J=13.2, 6.1 Hz, 2H), 2.34-2.25 (m, 2H). $^{13}$C NMR (126 MHz, D$_2$O) δ 164.26, 147.54, 146.69, 141.73, 134.73, 123.69, 74.79, 35.62, 26.07, 23.87.

2,6-di-3,5-dimethoxycarbonylpyridinium-9-thiabicyclo[3.3.1]nonane ditriflate (5k): $^1$H NMR (400 MHz, D$_2$O) δ 9.70 (s, 4H), 9.50 (s, 2H), 5.89 (d, J=12.5 Hz, 2H), 3.37 (s, 2H), 3.30 (dd, J=12.7, 5.2 Hz, 2H), 2.53-2.21 (m, 6H).

2,6-di-3-bromo-5-methoxycarbonylpyridinium-9-thiabicyclo[3.3.1]nonane ditriflate (5l): $^1$H NMR (400 MHz, D$_2$O) δ 9.51 (s, 2H), 9.48 (s, 2H), 9.28 (s, 2H), 5.75 (d, J=12.1 Hz, 2H), 3.32 (s, 2H), 3.17 (ddd, J=25.6, 13.2, 6.3 Hz, 2H), 2.51-2.18 (m, 6H).

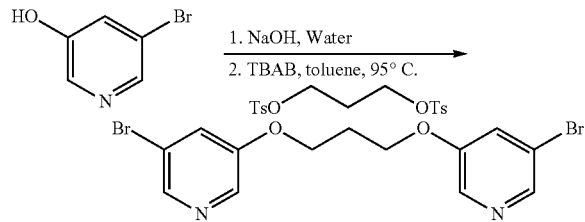

2i

Synthesis of bispyridine linker 2i: 5-Bromopyridin-3-ol (570 mg, 3.3 mmol, 4 equiv) was dissolved in 5 mL of 1 M NaOH with vigorous stirring for 1 h. Propane-1,3-diyl bis(4-methylbenzenesulfonate) (320 mg, 0.83 mmol, 1 equiv) and tetra-n-butylammonium bromide (367 mg 1.14 mmol, 1.3 equiv) in 10 mL toluene were added. The solution was heated to 95° C. overnight. The mixture was cooled, the solvent removed by rotary evaporation, and the product was purified by column chromatography (2:1 hexanes/EtOAc) elution. The desired product, 1,3-bis((5-bromopyridin-3-yl)oxy)propane (2i), was obtained as a white powder (216 mg, 67% yield). $^1$H NMR (400 MHz, CDCl$_3$) δ 8.32 (d, J=1.6 Hz, 1H), 8.27 (d, J=2.5 Hz, 1H), 7.41 (s, 1H), 4.23 (t, J=5.9 Hz, 2H), 2.39-2.29 (m, 1H). $^{13}$C NMR (126 MHz, CDCl$_3$) δ 154.99, 143.04, 136.22, 123.70, 120.26, 64.48, 28.71.

Representative procedure for the synthesis of polymers (entries 4-10 in Table 4 and Table 5). Compound 1a (21 mg, 0.1 mmol, 1 equiv), silver salt (0.2 mmol, 2 equiv) and the bispyridine of interest (0.1 mmol, 1 equiv) were mixed in 0.5 ml MeCN and stirred overnight at room temperature under inert atmosphere. For aqueous soluble polymers (entries 3, 4, 5, and 7 in Table 4; entries 1-3 in Table 5), the precipitate was collected and washed with MeCN. The charged adduct was dissolved in water and any remaining solids were removed by centrifugation, repeating the centrifugation step until the solution was not cloudy. The resulting solution was frozen and lyophilized to obtain the product as a colorless solid. For organic soluble polymers (entries 6, 8, 9, and 10 in Table 4; entry 4 in Table 5), any solid material was filtered out and the resulting solution was added to 10 ml CH$_2$Cl$_2$ to precipitate the desired product. The material was isolated by filtration and dried to give an off-white solid.

Alternative Strategies for Accelerating the Substitution Chemistry of Compound 1

Different halophilic transition metals were tested for their ability to speed the substitution reactions of 1 by interaction with the leaving group, accelerating the rate-limiting formation of the strained episulfonium intermediate. Representative Al, Sn, and Pd species showed no effect (Table 1). Silver salts were quite effective, prompting the isolation of the resulting intermediates as described below.

TABLE 1

Survey of halophilic metal complexes for the acceleration of reactions of 1 with PhCH$_2$NH$_2$ (10 equiv) in acetonitrile at room temperature.

| Entry | Halophilic Metal Complex | Reaction Time |
|---|---|---|
| 1 | None | 16 h |
| 2 | AgOTf | 2 h |
| 3 | AgNO$_3$ | 4 h |
| 4 | AlCl$_3$ | >16 h |
| 5 | SnCl$_2$ | 14 h |
| 6 | PdCl$_2$ | 12 h |
| 7 | Pd(OAc)$_2$ | 14 h |
| 8 | Zr(Cp)$_2$Cl$_2$ | >16 h |
| 9 | Pd(PPh$_3$)$_2$Cl$_2$ | >16 h |

Comparison of Reactivities between Different WCL Intermediates

Figure 2:
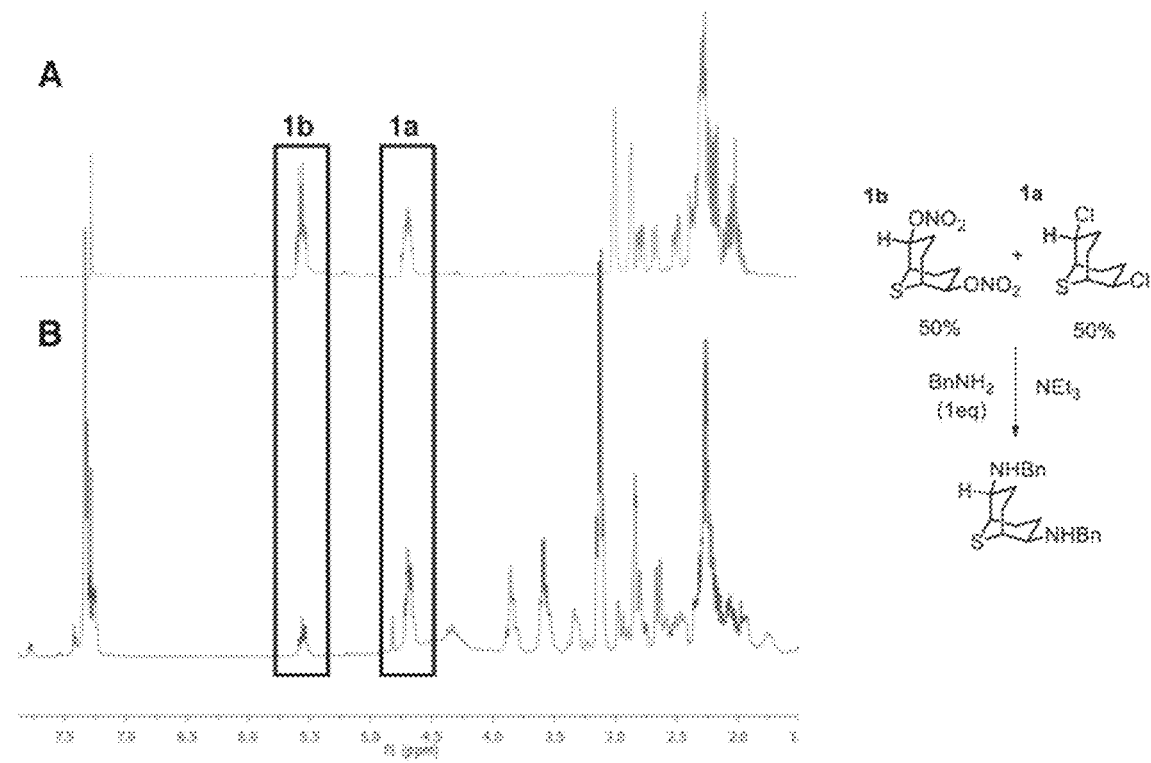
FIG. 2 shows the $^1$H NMR analysis of competition experiments between WCL nitrate and chloride electrophiles for benzylamine.

Compound 1a (10.5 mg, 0.05 mmol, 1 equiv) and 1b (0.2 mL of 0.25 M MeCN solution, 0.05 mmol, 1 equiv) were combined in 1 mL MeCN. The solvent was then evaporated and the residue analyzed by $^1$H NMR in CDCl$_3$ (FIG. 2, spectra A). In parallel, a separate identical [1a+1b] mixture in MeCN was treated with benzylamine (8.1 μL, 0.1 mmol, 1 equiv) and triethylamine (69.6 μL, 0.5 mmol, 5 equiv, previously shown to be unreactive towards WCL compounds and used to soak up any HCl produced). After 24 hours, the mixture was evaporated, redissolved in CDCl$_3$, and analyzed by $^1$H NMR (FIG. 2, spectra B). The data show almost complete reaction of the amine with the nitrate electrophile rather than the chloride.

Figure 3:
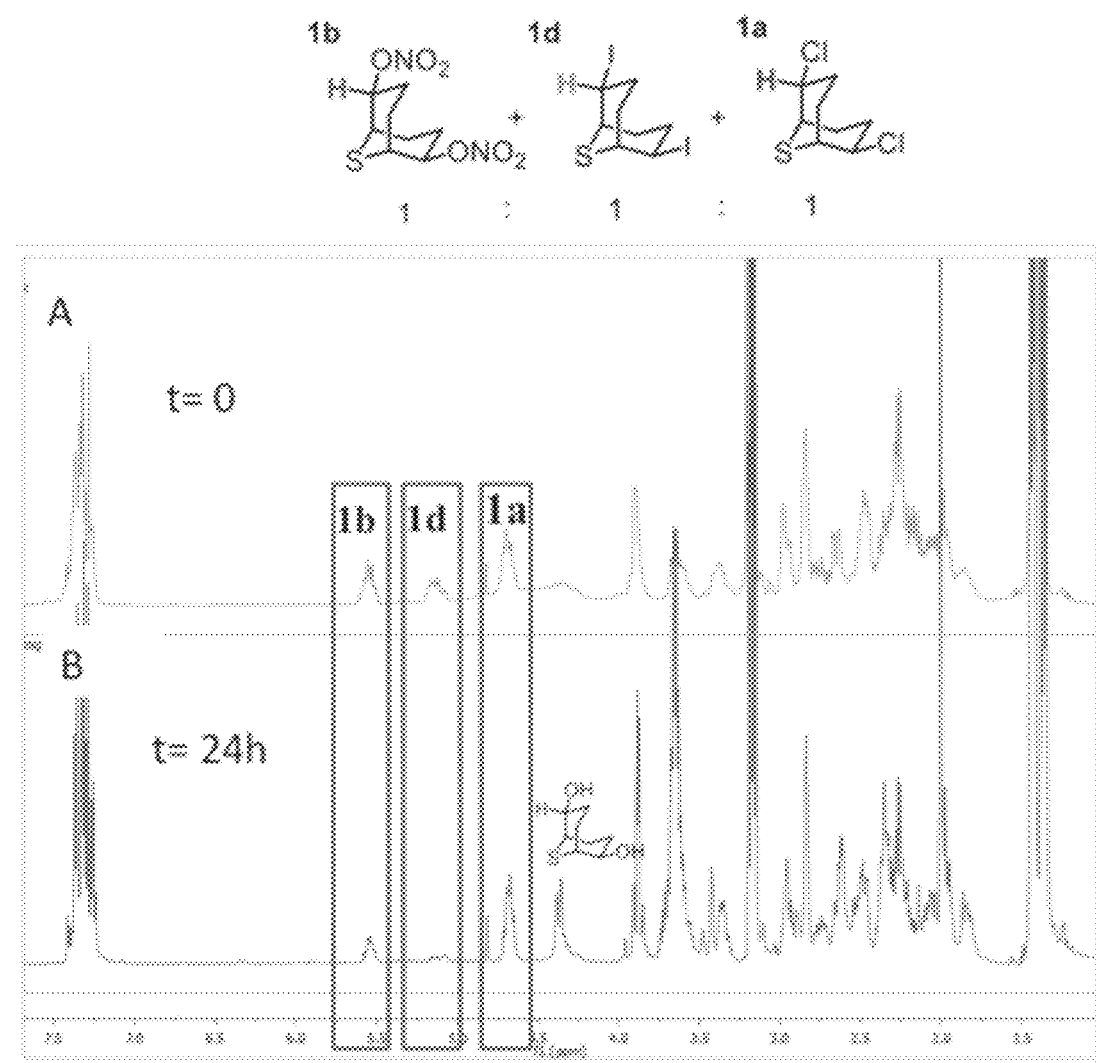
FIG. 3 shows the $^1$H NMR analysis of competition experiments between WCL chloride, nitrate, and iodide electrophiles for benzylamine.

An internal competition between all three easy-to-handle electrophiles (chloride, nitrate, iodide; 1a, 1b, and 1d) was performed in a similar manner, in which 0.05 mmol of each was combined in acetonitrile and treated with slightly less than one equivalent of BnNH$_2$ (0.125 mmol) and 5 equiv. (5 mmol) of Et$_3$N (total volume 1 mL). NMR spectra recorded immediately and after 24 h (in each case, an aliquot was removed, evaporated, and redissolved in CDCl3) are shown in FIG. 3. Integration of the α-protons for each electrophile showed nearly equimolar ratios at the start, and a highly skewed distribution after reaction. The relative reactivities thus revealed are iodide>nitrate>chloride.

Monitoring Fragmentation of Representative WCL-Substituted Adducts and WCL-Based Oligocations by $^1$H NMR The fragmentation of cationic adducts was followed by $^1$H NMR in deuterated buffer, with the relative concentration of each species established by integration of unique resonances. Each adduct in Table 3 and Table 4 was thus examined in three independent runs.

Figure 4A:
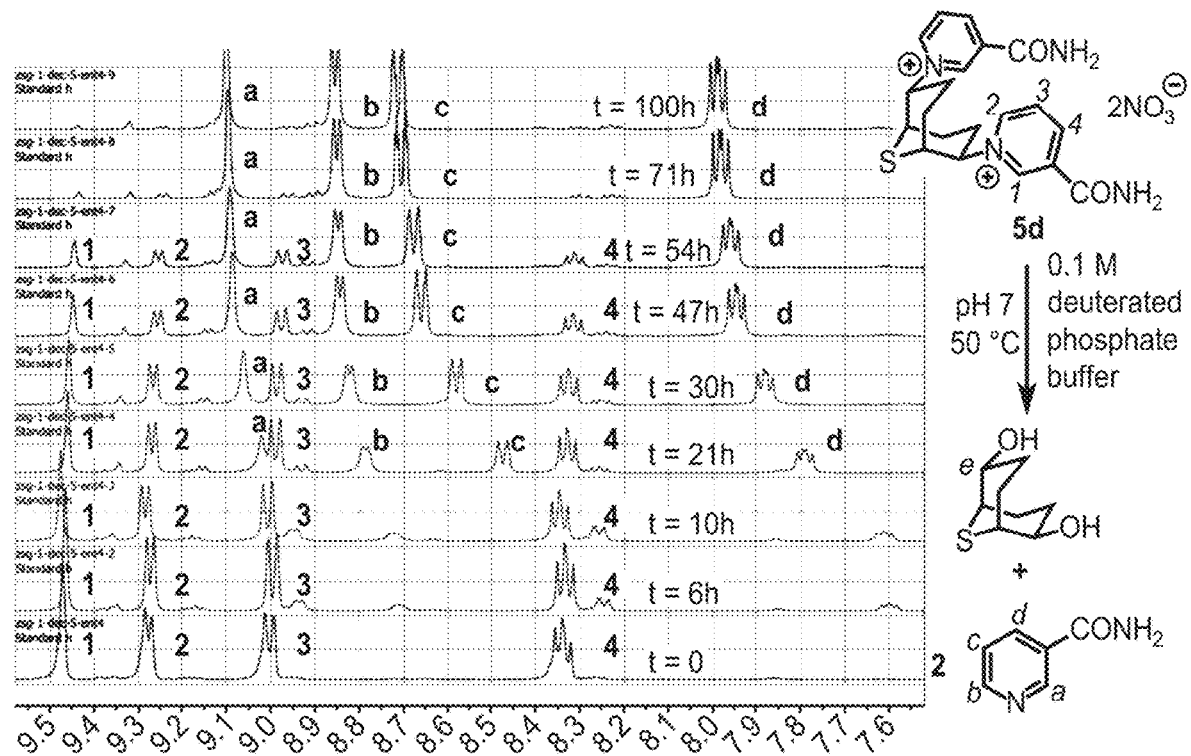
FIGS. 4A-4B show $^1$H NMR spectra taken at various intervals over 100 hours as 5d was incubated in deuterated aqueous phosphate buffer (pH 7) at 50° C.
Figure 4B:
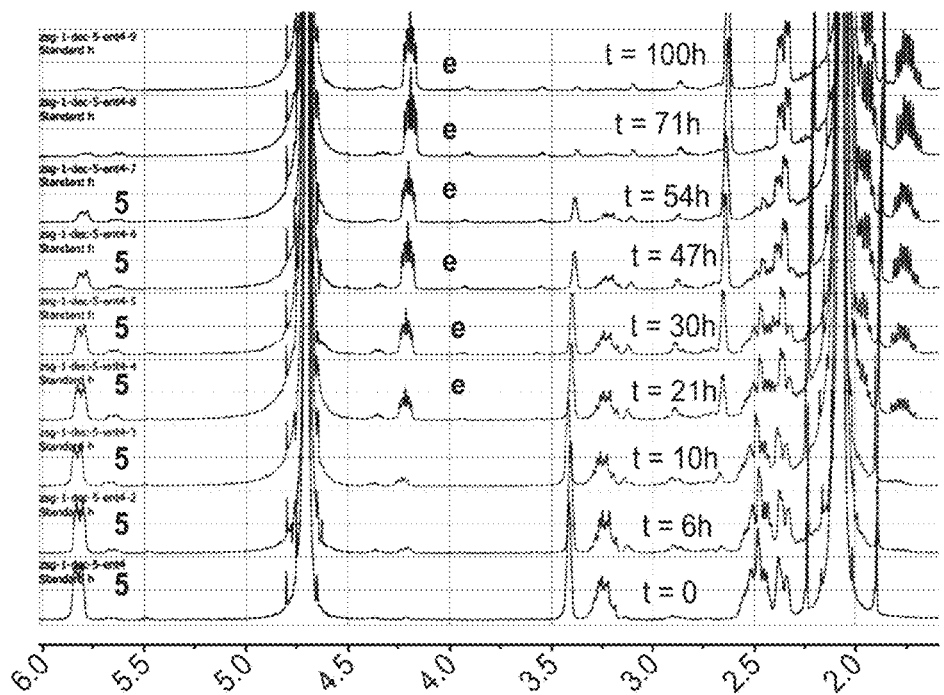
Figure 5:
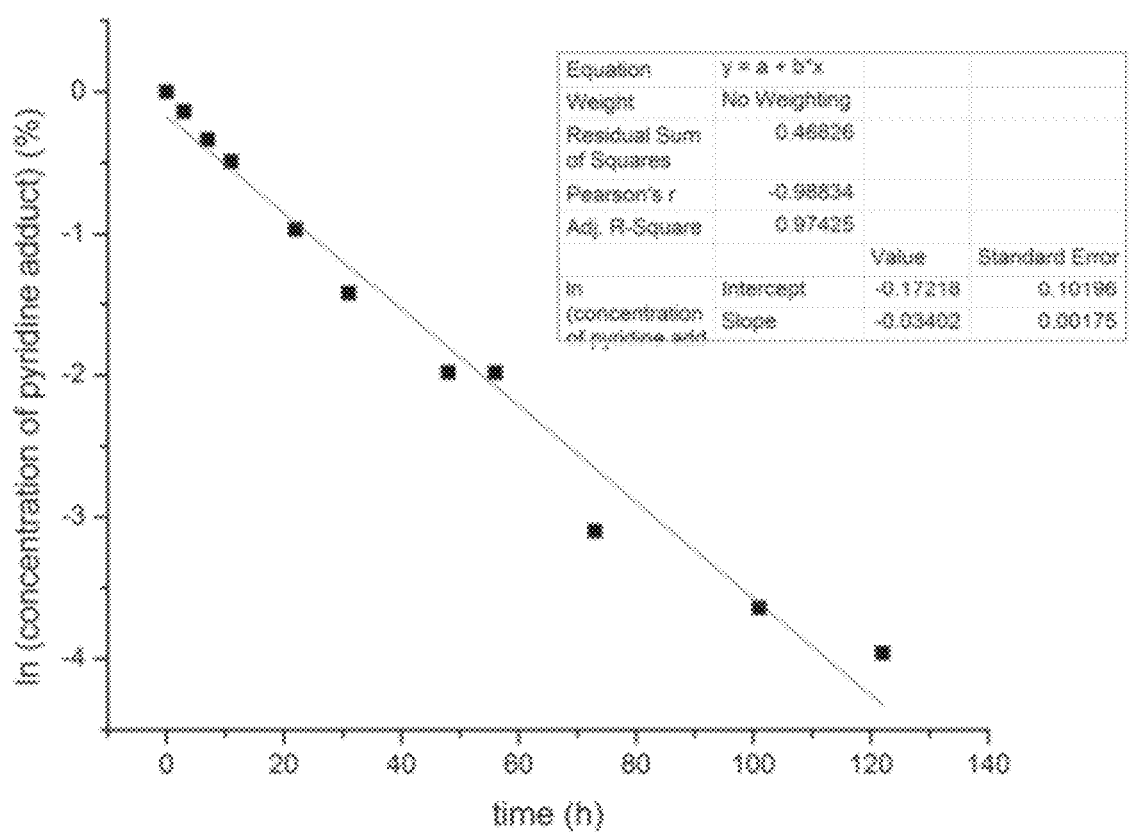
FIG. 5 shows the pseudo-first order plot obtained for the fragmentation of 5d in deuterated buffer at 50° C.

FIGS. 4A-4B show representative fragmentation data for compound 5d, with the relative concentration of each species established by integration of unique resonances, labeled in the $^1$H NMR spectra. The first-order kinetic treatment is shown in FIG. 5.

Figure 6:
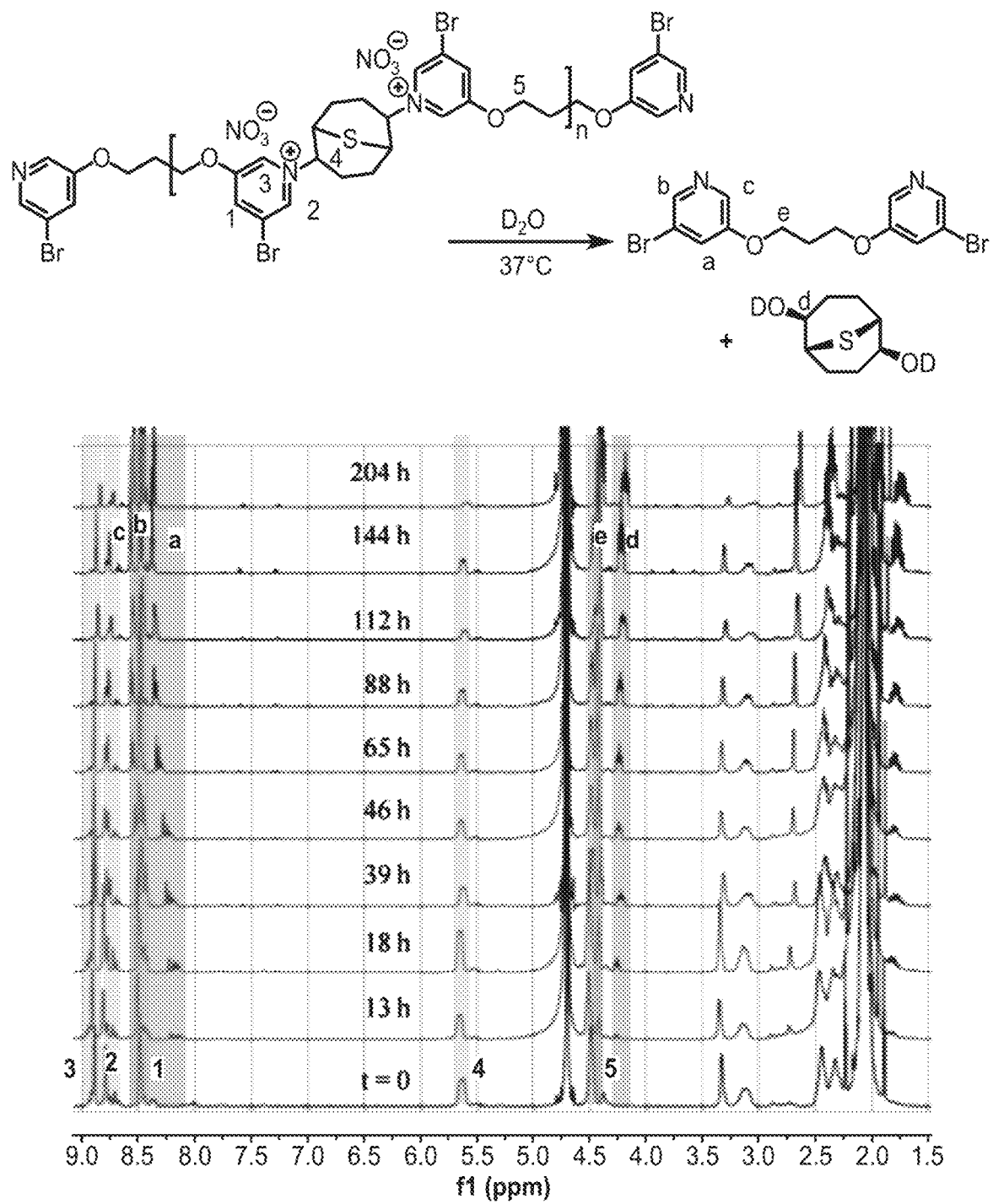
FIG. 6 shows $^1$H NMR spectra taken at various intervals over 204 hours as polymer 3l was incubated in deuterium oxide at 37° C.

FIG. 6 shows representative fragmentation data for polymer 3i, with the relative concentration of each species established by integration of unique resonances, labeled in the $^1$H NMR spectra.

GPC Analysis of WCL Polymers Before and After Fragmentation

Figure 7A:
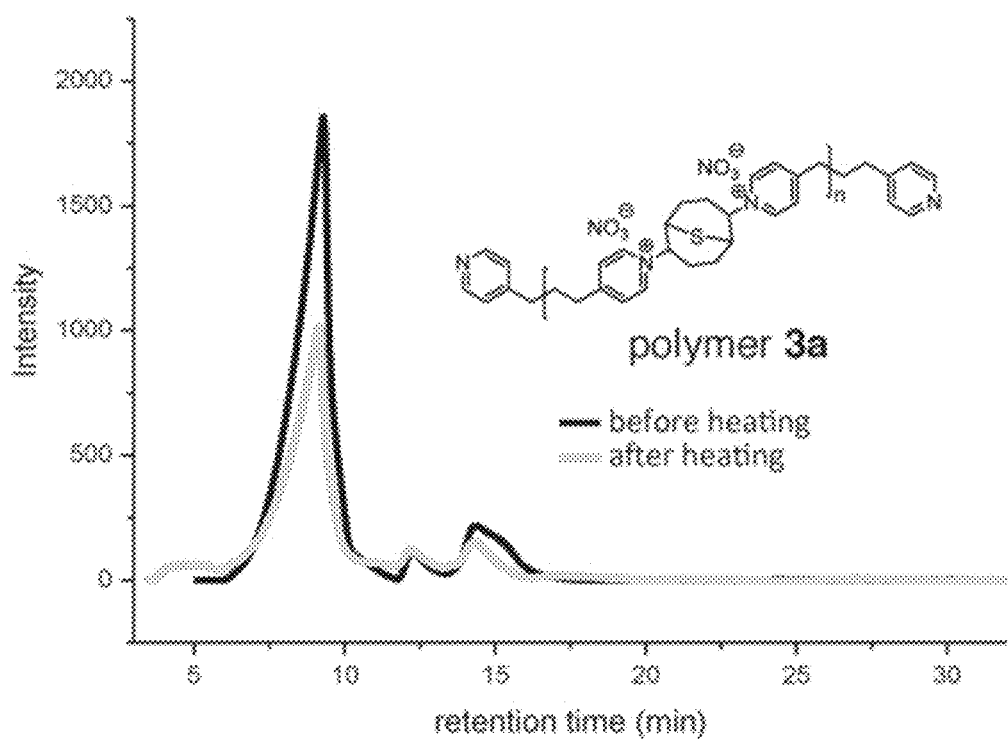
FIG. 7A shows gel permeation chromatography (GPC) traces of polymer 3a before (black trace) and after (gray trace) fragmentation in water at 37° C.
Figure 7B:
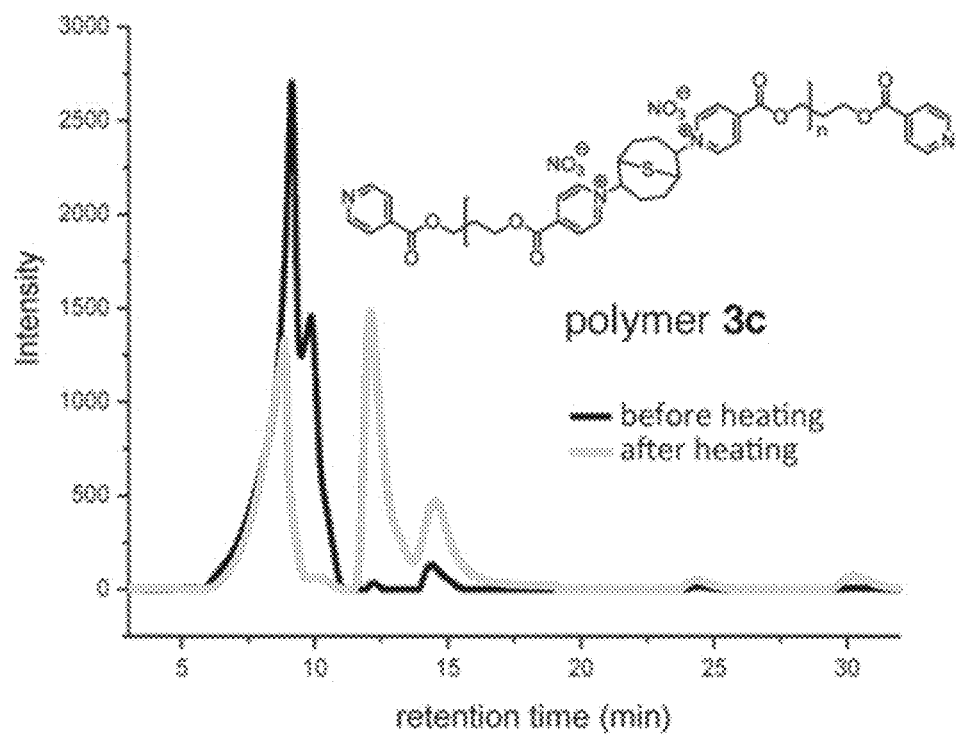
FIG. 7B shows GPC traces of polymer 3c before (black trace) and after (gray trace) fragmentation in water at 37° C.
Figure 7C:
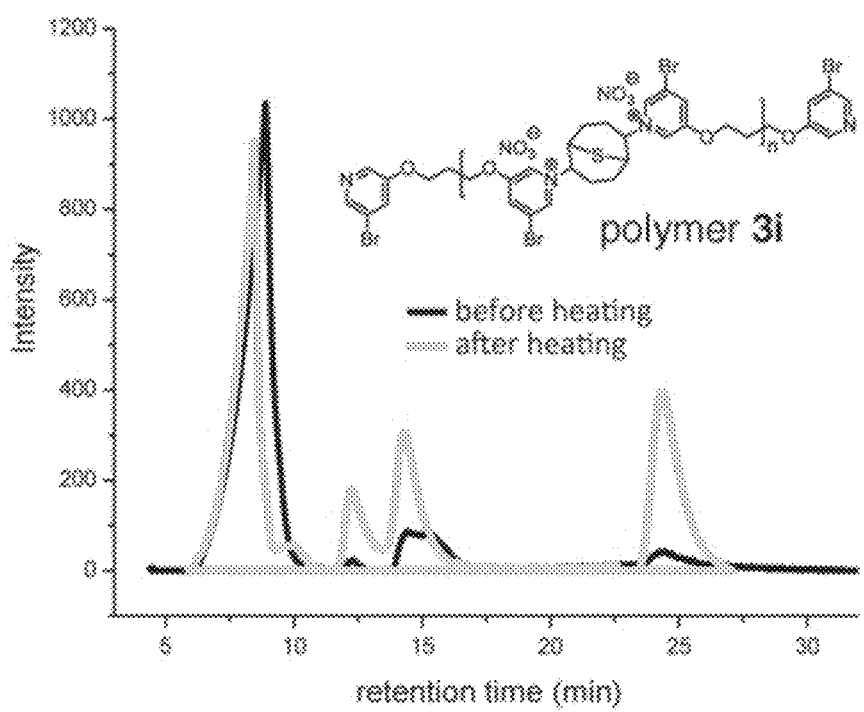
FIG. 7C shows GPC traces of polymer 3i before (black trace) and after (gray trace) fragmentation in water at 37° C.

Three WCL based polymers were dissolved in pure water at 1 mg/mL concentration solution and characterized by aqueous gel permeation chromatography (GPC, black traces in FIGS. 7A-7C). Separate identical solutions were heated at 37° C. for 36 hours and analyzed again by aqueous GPC (gray traces in FIGS. 7A-7C). The major peaks between 8 and 10 mins were assigned to polymers; after heating, small molecule components were evident as peaks at longer retention times. Polymer 3a was confirmed as being a particularly stable molecule, showing no difference in GPC trace after heating. Polymers 3c and 3i underwent partial degradation as expected from NMR experiments; interestingly, the remaining polymer peaks shifted modestly but reproducibly to shorter retention time (higher molecular weight, FIGS. 7B-7C). This could suggest (a) some ligation of oligomers (bearing pyridine nucleophiles at the end) with active episulfonium electrophilic intermediates formed in the decomposition process, and/or (b) the presence of cyclic structures of sufficient size to result in a shift to higher molecular weight upon partial cleavage. Calculation of molecular weight parameters by comparison to dextran standards proved to be nonsensical, so Mn, Mw, and polydispersities could not be assigned by this method.

Thermal Analysis of Representative WCL Polymers

Figure 8A:
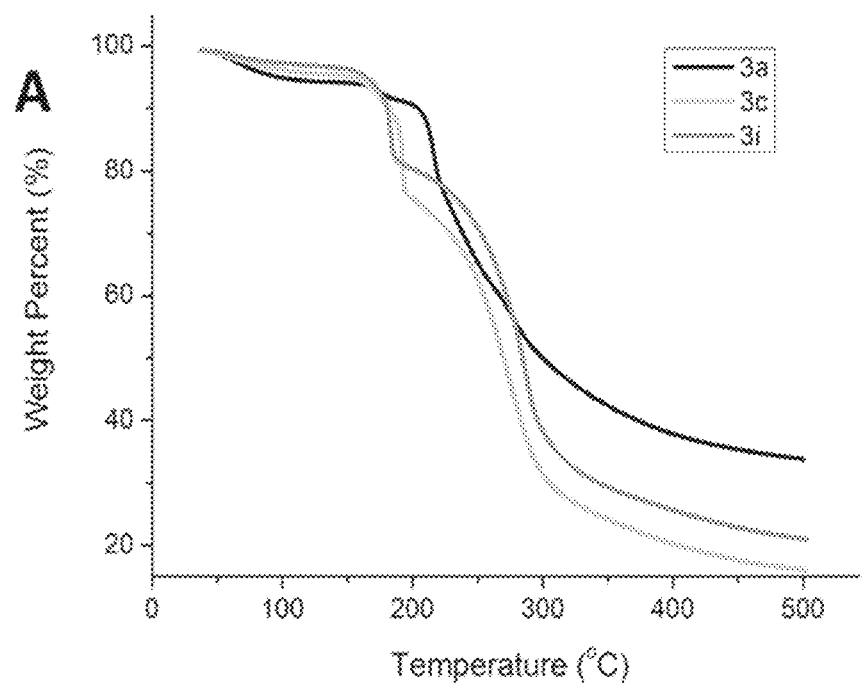
FIG. 8A shows the results of thermogravimetric analysis (TGA) of polymers 3a, 3c, and 3i.
Figure 8B:
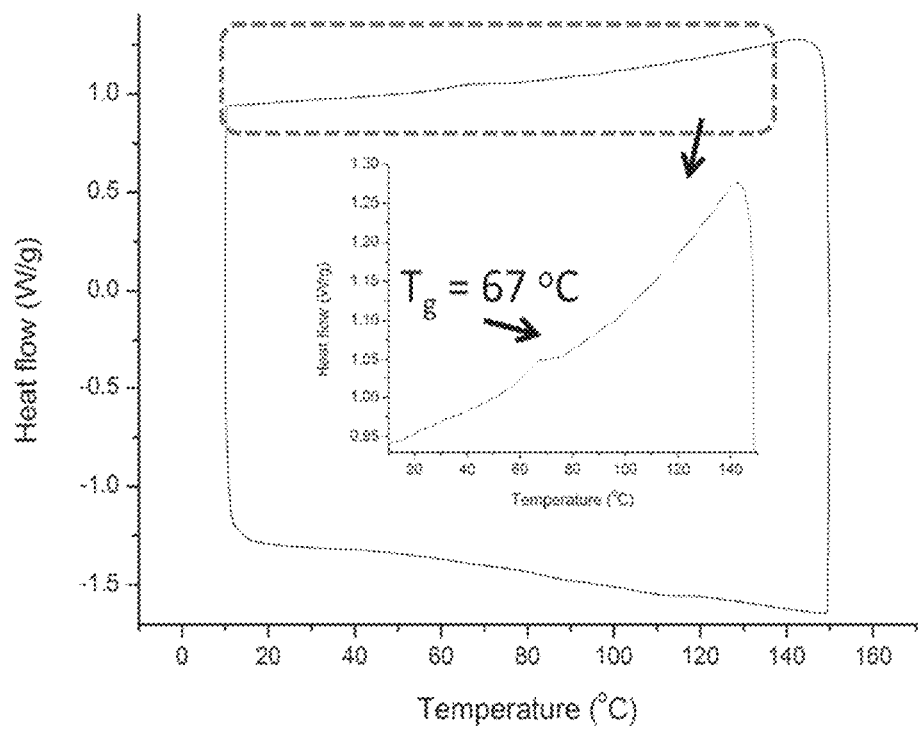
Figure 9A:
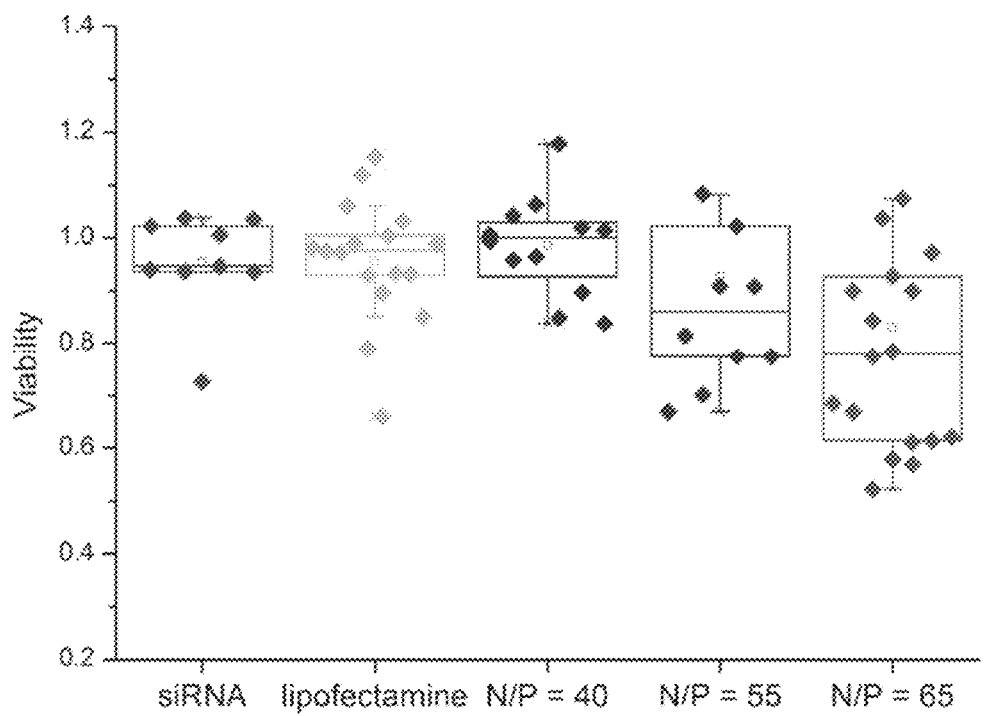
Figure 9B:
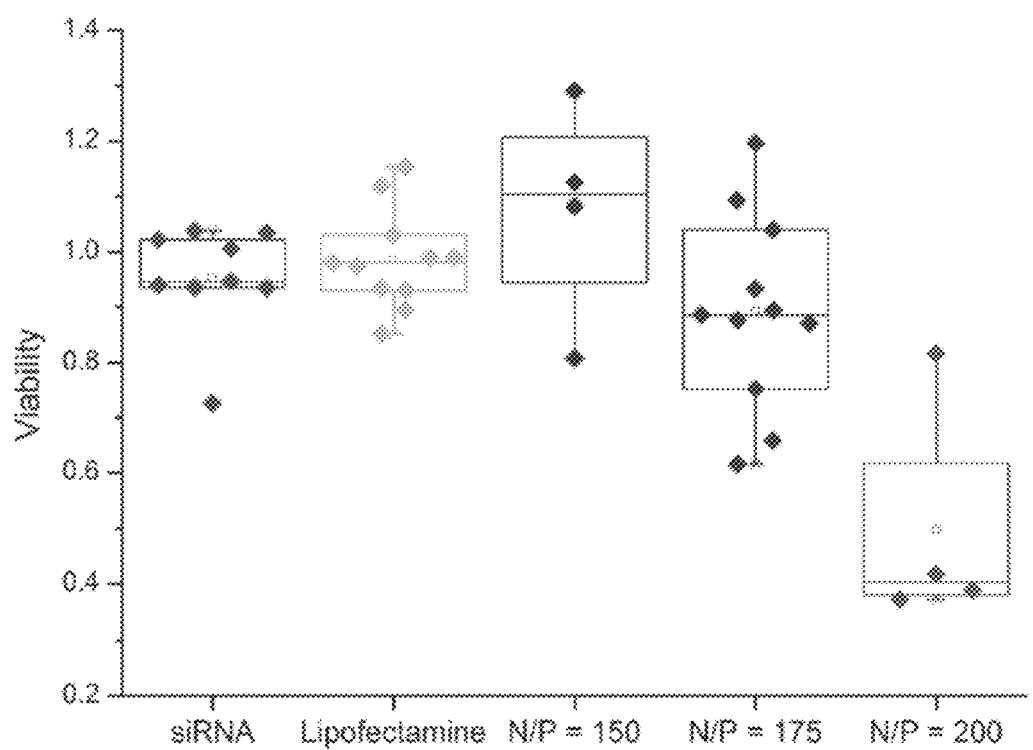
FIG. 9B shows a box-and-whisker plot of viability test results for GFP-HeLa at different N/P ratios with polymer 3i.
Figure 10:
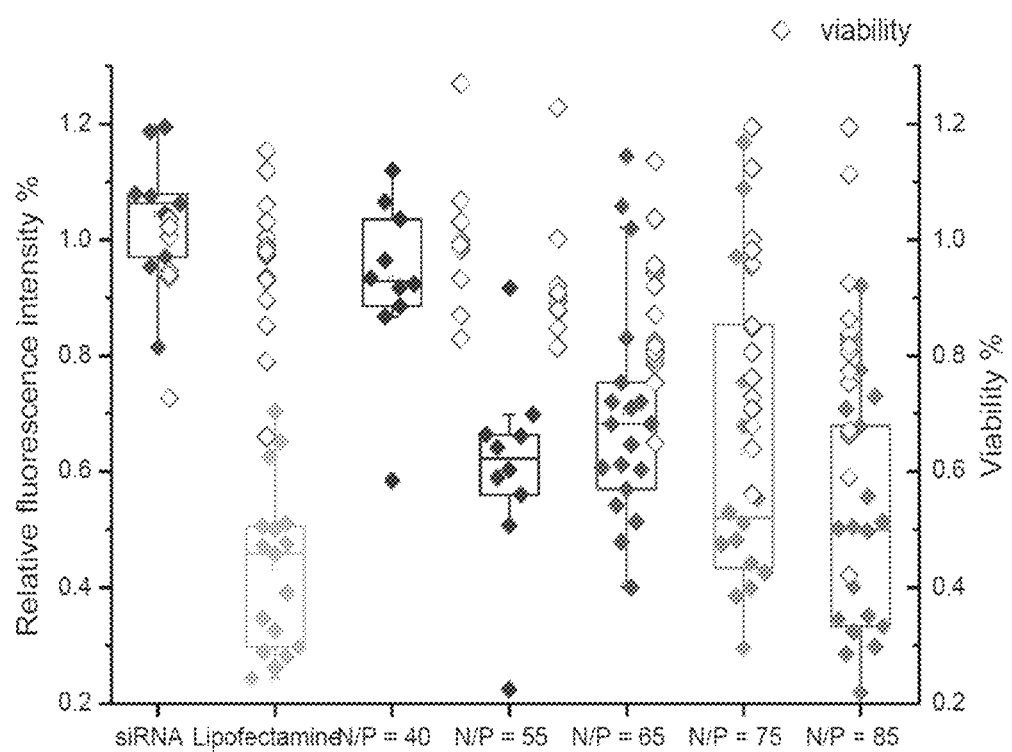

The thermal decomposition temperature of WCL polymers were measured on a Perkin-Elmer Pyris 1 thermogravimetric analyzer (TGA) in a nitrogen atmosphere (flow rate 25 mL/min) with a heating rate of 10° C./min. Thermal transitions of WCL polymer 3a were measured with a TA Q200 Differential Scanning calorimeter (DSC) in a nitrogen atmosphere (flow rate 50 mL/min) with a heating/cooling rate of 10° C./min. Each sample was scanned for three cycles and the 2$^{nd}$ cycle is presented in FIG. 8B.

Polymer 3a began extensive decomposition at approximately 220° C. while the decomposition of 3c and 3i was initiated at approximately 180-185° C., with two obvious stages of mass loss. A glass transition of 3a was observed at 67° C., comparable to Tg values previously reported for representative polyionenes.

Cell Culture

All cell culture reagents were acquired from Life Technologies (Carlsbad, Calif.) unless noted otherwise. HeLa cells were purchased from ATCC (Manassas, Va.). GFP-HeLa cells were a gift from the Schmid lab (University of Texas, Southwestern, Dallas, Tex.). Cells were grown and maintained in complete growth media: Dulbecco's Modified Eagle's Medium (DMEM), supplemented with 5% Fetal bovine serum (FBS), sodium pyruvate (1 mM), penicillin (100 units/mL), streptomycin (100 μg/mL), and GlutaMAX (2 mM). Cells were grown at 37° C. under humidified air with 5% CO$_2$. Glass-bottomed culture dishes were purchased form MatTek (Ashland, Mass.). Accutase was purchased from Innovative Cell Technologies, Inc. (San Diego, Calif.). 96-well microtiter plates were purchased from Thermo Fisher (Waltham, Mass.).

siRNAs were a gift from Integrated DNA Technologies (Coralville, Iowa), with the following sequences. GFP sense: 5'-CAAGCUGACCCUGAAGUUCUU, GFP antisense: 5'-GAACUUCAGGGUCAGCUUGUU. Approximately 1×10$^4$ GFP-HeLa cells/well were plated in a 96-well plate in 100 μL of complete growth media, and adhered overnight at 37° C. For postitive control experiments, 10 nM double-stranded siRNA was transfected with Lipofectamine RNAiMAX according to the manufacturer's protocol. After 24 h, the media was replaced with complete growth media (100 μL/well). Fluorescence was measured 48 h post-transfection. For knockdown experiments with polyplexes, cells were plated as described. 100 μL of oligomer/ds-siRNA complexes at indicated N/P ratios were added to cells. Media was again replenished after 24 h. Fluorescence was measured 48 h post-treatment.

Viability of Mammalian Cells in the Presence of WCL Monomers and Polymers

Approximately 1×10$^4$ CHO-K1 cells/well were plated in a 96-well plate in 100 μL of complete growth media, and adhered overnight at 37° C. The media was then replaced by 100 μL of polymer or monomer in serum-free media at the indicated concentration. Full media was replenished after 4 or 24 h. Viability was measured by MTT assay, with non-treated cells assigned as 100% viability. The results are plotted in FIGS. 11A-11D and 12A-12H.

Results and Discussion

Fundamental Reactivity

While the substitution chemistry of compound 1a (Scheme 1, X=Cl) is quite clean, its reaction rate at room temperature (rate constant ≈2.4×10$^{-4}$M$^{-1}$s$^{-1}$) and thermodynamic driving force were thought to be incompatible with the generation of high molecular weight polymers by the simple condensation route outlined in Scheme 1. Accordingly, more reactive forms of 1 were prepared, focusing on the rate-limiting formation of episulfonium ion intermediate. Treatment of 1a with silver nitrate or silver triflate in acetonitrile afforded 1b or 1c in high yield after filtration of AgCl. The triflate is proved to be the most reactive, but may have limited utility under practical conditions because of its high sensitivity to hydrolysis with atmospheric moisture or trace water in the solvent. The nitrate derivative 1b, in contrast, was stable enough to survive standard isolation, handling, NMR characterization. The apparent Finkelstein reaction of 1a with sodium iodide in acetone gave 1d in high yield, which was similarly stable to isolation by filtration and characterization in air. The NMR spectra revealed significant differences between the chemical shifts of the H atoms adjacent to the leaving groups (on C1 and C5) among the different derivatives, suggesting that the order of reactivity would be iodide (1d)≥nitrate (1b)>chloride (1a), correcting for the upfield shift characteristic of C—H bonds next to iodine due to factors unrelated to the electron density of the C-halogen bond.

A preliminary assessment of substitution reactivity was obtained by competition reactions in which an equimolar mixture of two electrophiles was treated with half an equivalent of benzylamine (FIG. 1). These pairwise comparisons, as well as reaction of all three electrophiles together (FIG. 2, FIG. 3) confirmed the above order of reactivity, with nitrate approximately 10 times more reactive than chloride, and iodide at least 5 times more reactive than nitrate. These differences are expected to be general since the reaction rate is only weakly dependent on the nature of the capturing nucleophile.

The parent pyridine derivative 5a was highly stable toward fragmentation in water (less than 5% hydrolysis observed after 1 week at 50° C.), so pyridine nucleophiles were chosen to include primarily electron-withdrawing groups to enhance this rate. Such pyridine derivatives are necessarily poorer nucleophiles for the forward step, so the enhanced reactivity of 1b was important for the efficient synthesis of the corresponding substituted pyridine dicationic adducts, as shown in Table 2. Each adduct dinitrate was isolated, characterized, and heated at 50° C. in deuterated buffer; following the disappearance of the adduct by NMR, first-order rate constants of fragmentation were obtained. The NMR spectra also confirmed the clean nature of the reaction, giving diol 4 and the released pyridines.

Figure 13A:
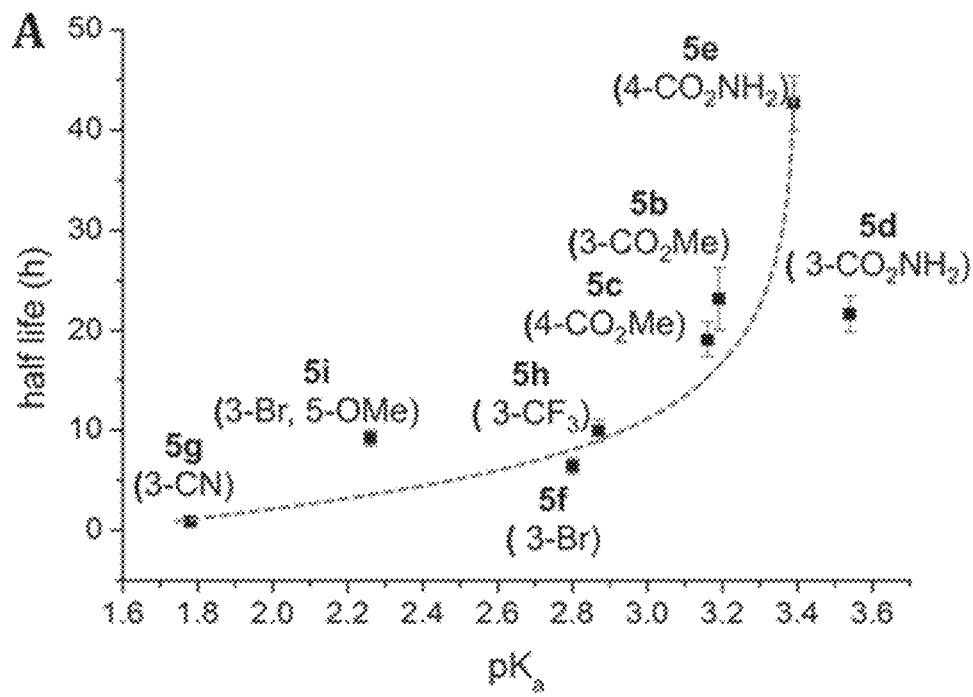
FIG. 13A is a plot of the adduct half life at 50° C. vs. pyridine basicity (see also Table 1). The pyridine basicity is indicated by the calculated $pK_a$ of the conjugate acid. The dotted line is meant to highlight the approximate trend, and is not a mathematical fit.
Figure 13B:
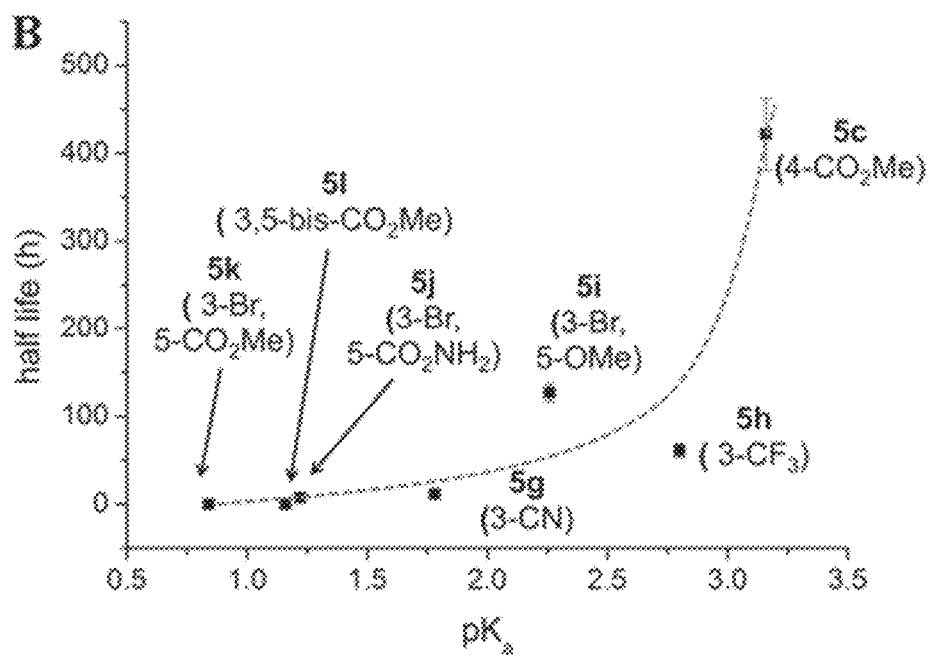
FIG. 13B is a plot of the adduct half life at 37° C. vs. pyridine basicity (see also Table 2). The pyridine basicity is indicated by the calculated $pK_a$ of the conjugate acid. The dotted line is meant to highlight the approximate trend, and is not a mathematical fit.

The stability of pyridine adducts to fragmentation in water was found to roughly correlate with calculated pyridine basicity (FIGS. 13A-13B). This is consistent with the idea that more nucleophilic pyridine groups are more difficult to eject from the pyridinium adduct structure, and that Brønsted basicity is indicative of nucleophilicity. In practice, half-lives were shown to vary over a 40-fold range (Table 2). Decomposition rates at 37° C., tested for potential applications in vivo, were found to be much slower than at 50° C., as expected for a fragmentation reaction. For example, 5c underwent hydrolysis approximately 23 times faster at 50° C. than at 37° C. To tune these potential release rates to a reasonably fast range, two electron-withdrawing groups were used, leaving the ortho positions unsubstituted to avoid steric problems in adduct formation (Table 3). Some additional limits were imposed on the process by the observation that pyridines having too many (or too potent) electron-withdrawing substituents were found not to react cleanly with 1b or 1d. For example, the strongly electron-deficient 3-bromo-5-amidopyridine (calculated $pK_a=1.22$) did not form a clean adduct unless reacted with the most reactive ditriflate electrophile, 1c. The resulting compound 5j underwent relatively fast fragmentation (half life less than a day), as expected. Carboxylate-based electron-withdrawing groups provide for easy linkage of pyridine units together to make higher-valent monomers for the synthesis of fragmentable polymers and crosslinked materials.

TABLE 3

Comparison of pseudo first order fragmentation of pyridine adducts at 37° C.

| Compound | R | $pK_a$ | $k_{frag}$ (h$^{-1}$) | $k_{rel}$ | half life (h) |
|---|---|---|---|---|---|
| 5c | 4-CO$_2$Me | 3.16 | $(0.16 \pm 0.01) \times 10^{-2}$ | 0.3 | 422 ± 41 |
| 5g | 3-CN | 1.78 | $(5.87 \pm 0.71) \times 10^{-2}$ | 11 | 11.8 ± 1.9 |
| 5h | 3-CF$_3$ | 2.8 | $(1.14 \pm 0.16) \times 10^{-2}$ | 2.1 | 61 ± 8 |
| 5i | 3-Br, 5-OMe | 2.26 | $(0.55 \pm 0.04) \times 10^{-2}$ | 1 | 127 ± 10 |

TABLE 2

Comparison of pseudo first order fragmentation of pyridine adducts at 50° C.; $pK_a$ refers to the conjugate acid of the pyridine calculated using Advanced Chemistry Development (ACD/Labs) Software V11.02

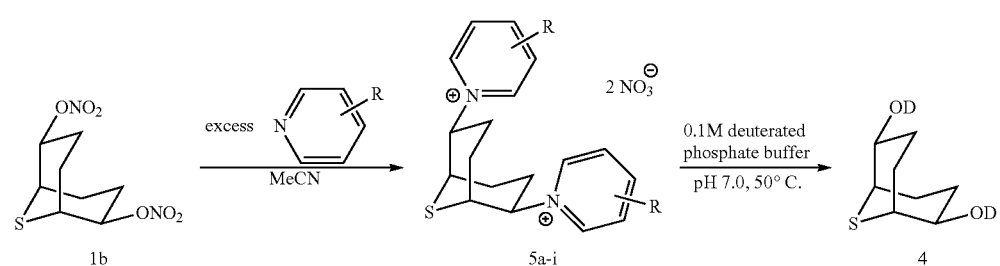

| Compound | R | $pK_a$ | $k_{frag}$ (h$^{-1}$) | $k_{rel}$ | half life (h) |
|---|---|---|---|---|---|
| 5a | H | 5.23 | $<1 \times 10^{-4}$ | — | — |
| 5b | 3-CO$_2$Me | 3.19 | $(3.03 \pm 0.38) \times 10^{-2}$ | 1.86 | 23.2 ± 3.1 |
| 5c | 4-CO$_2$Me | 3.16 | $(3.66 \pm 0.33) \times 10^{-2}$ | 2.25 | 19.1 ± 1.8 |
| 5d | 3-CO$_2$NH$_2$ | 3.54 | $(3.18 \pm 0.32) \times 10^{-2}$ | 1.95 | 21.7 ± 1.8 |
| 5e | 4-CO$_2$NH$_2$ | 3.39 | $(1.62 \pm 0.10) \times 10^{-2}$ | 1.00 | 42.7 ± 2.7 |
| 5f | 3-Br | 2.87 | $(6.59 \pm 0.58) \times 10^{-2}$ | 4.05 | 9.9 ± 1.1 |
| 5g | 3-CN | 1.78 | $(74.8 \pm 5.4) \times 10^{-2}$ | 46.2 | 0.9 ± 0.1 |
| 5h | 3-CF$_3$ | 2.8 | $(10.8 \pm 0.98) \times 10^{-2}$ | 6.68 | 6.4 ± 0.8 |
| 5i | 3-Br, 5-OMe | 2.26 | $(7.51 \pm 0.53) \times 10^{-2}$ | 4.64 | 9.2 ± 0.8 |

TABLE 3-continued

Comparison of pseudo first order fragmentation of pyridine adducts at 37° C.

| Compound | R | $pK_a$ | $k_{frag}$ (h$^{-1}$) | $k_{rel}$ | half life (h) |
|---|---|---|---|---|---|
| 5j | 3-Br, 5-CO$_2$NH$_2$ | 1.22 | (9.34 ± 0.87) × 10$^{-2}$ | 17 | 7.4 ± 0.5 |
| 5k | 3-Br, 5-CO$_2$Me | 0.84 | (11.9 ± 1.13) × 10$^{-2}$ | 22 | 0.24 ± 0.01 |
| 5l | 3-CO$_2$Me, 5-CO$_2$Me | 1.16 | (10.9 ± 1.81) × 10$^{-2}$ | 20 | 0.27 ± 0.01 |

Oligo- and Polycation Synthesis

The condensation polymerization of a dipyridine nucleophile and WCL electrophile was explored using the parent compound 2a (Scheme 1, Table 4). Reaction of 1a and 2a in MeCN solvent at 50° C., conditions that produce good yields of adducts with pyridine itself, give only small oligomers (average n=3). In contrast, dinitrate 1b, generated in situ from 1a and AgNO$_3$, gave copious quantities of precipitate within two minutes of mixing with an equimolar amount of 2a, all in MeCN. Filtration and washing provided the corresponding species 3a•(NO$_3$)$_{2n}$. Characterization of this material was aided by its high solubility in water and by the fact that the second substitution event on each WCL core is usually faster than the first, so that chains are capped by the pyridine nucleophile. $^1$H NMR in D$_2$O therefore showed distinct residues for non-alkylated pyridines at each end, enabling an estimate of average chain length of approximately n=10 for 3a prepared under these conditions (molecular weight approximately 4000). Gel permeation chromatography (GPC) analysis also showed minor fractions with longer retention time, consistent with shorter chains or cyclic oligomers. Somewhat higher molecular weights were obtained with heating to 50° C. (n≈13), or with the use solvents better able to support the developing polycation and therefore to delay precipitation until longer chain lengths are achieved (Table 3). In a brief survey of activating silver salts and solvents, the use of AgPF$_6$ in DMSO was found to give the largest average molecular weights as determined by NMR end-group analysis (Table 4); polydispersities could not be assessed because of the lack of suitable GPC standards (values obtained against dextran standards in water were wildly divergent from estimates made by NMR) and because m/z values for molecules of different chain lengths are close enough to make deconvolution of the mass spectra of these mixtures difficult. Values of hydrodynamic radii determined by dynamic light scattering (Table 6) were comparable with those of ammonium ionenes with similar degrees of polymerization. Analysis by TGA showed representative oligomers to have the anticipated stability (decomposition initiation at approximately 200° C.), and DSC revealed discrete glass transitions to be rare, both consistent with materials that are potentially dynamic at higher temperatures. Note that the WCL electrophiles are used here in racemic form, making for polymeric structures that are likely mixtures of many diastereomers.

TABLE 4

Condensation polymerization of 1a + 2a.

| Entry | [1a] = [2a] (M) | Additive (2 equiv) | Solvent | Temperature | $M_n$ (kDa) | n$^a$ |
|---|---|---|---|---|---|---|
| 1 | 0.1 | None | MeCN | 50° C. | 1.5 | 3 |
| 2 | 0.1 | None | THF/H$_2$O | RT | — | — |
| 3 | 0.1 | AgNO$_3$ | MeCN | RT | 4-5 | 8-10 |
| 4 | 0.1 | AgNO$_3$ | MeCN | 50° C. | 6 | 13 |
| 5 | 0.1 | AgNO$_3$ | THF/H$_2$O | RT | — | — |
| 6 | 0.1 | AgBF$_4$ | DMF | RT | 5.3 | 10 |
| 7 | 0.2 | AgNO$_3$ | DMSO | RT | 9 | 18 |
| 8 | 0.2 | AgOTf | DMSO | RT | 11.5 | 23 |
| 9 | 0.4 | AgPF$_6$ | DMSO | RT | 22.2 | 35 |
| 10 | 0.2 | AgBF$_4$ | DMSO | RT | 11.4 | 22 |

$^a$n = average degree of polymerization

Figure 14:
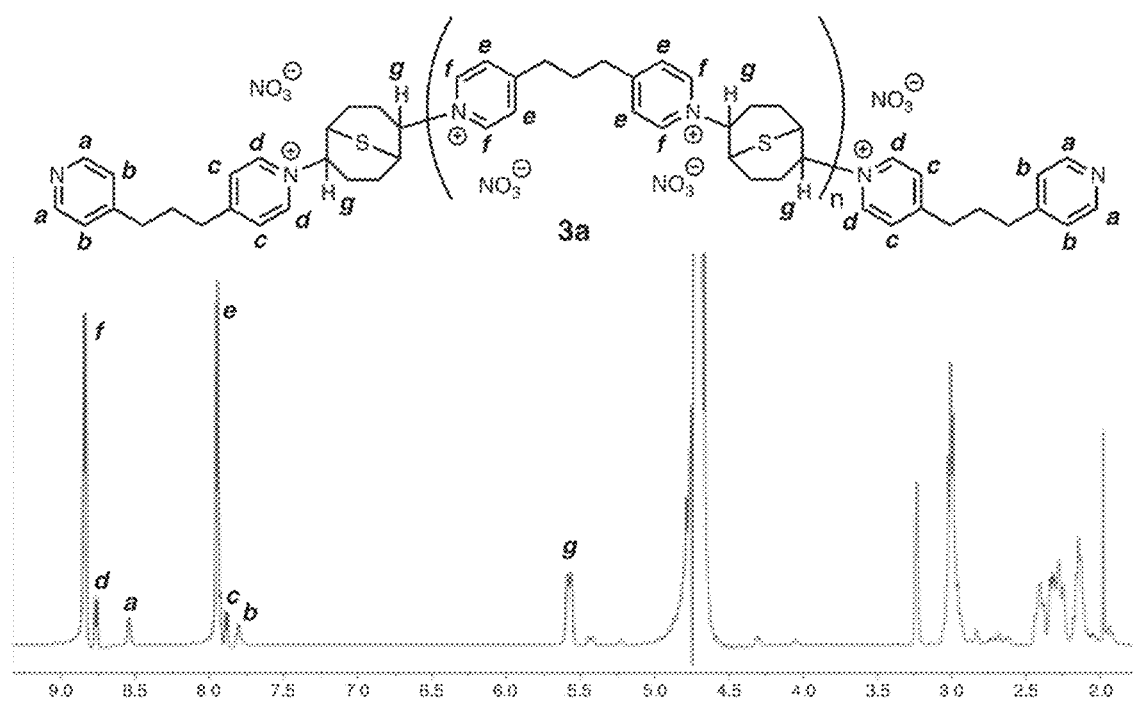
FIG. 14 shows the $^1H$ NMR spectrum of an oligomer formed by reaction of 1b and 2a (Table 4, entry 3).

Using the conditions of Table 4, three additional oligocations were prepared from the bis(pyridine) linkers as shown in Table 5. The synthetic procedure proved to be modular, giving oligomers of similar size (n≈10) with the same methods of isolation and analysis. The stabilities of these compounds toward fragmentation under aqueous conditions were assessed by NMR in deuterated buffer, following the disappearance of the thiabicyclononane C—H resonance adjacent to the pyridine group (position g in FIG. 14) and the appearance of the corresponding resonance (4.3 ppm) for the diol product 4 (FIG. 6). The observed half lives of the WCL-pyridine bonds in these oligomers corresponded reasonably well (within a factor of 2) with the analogous small-molecule bis(pyridine) adducts described above, ranging from several hours to a month at physiological temperature and pH. Note of course that the oligomer structures decompose much faster than this, since the rupture of only a fraction of the bonds (occurring at approximately the same first-order rate at each position of the chain) would be necessary to chop the linear structure into shorter pieces. Indeed, these materials are also very likely to be dynamic in nature, since breakage of a C—N(pyridyl) bond is probably followed by re-formation of that same bond more often than by irreversible capture of the intermediate episulfonium ion with water.

TABLE 5

Representative oligocations and half lives ($t_{1/2}$) of C-N bond fragmentation in aqueous buffer (pH 7).

| Nucleophilic Monomer [Polymer] | n$^a$ | T$^b$ | $t_{1/2}$ | $t_{1/2}$ of Small Molecule Analogue |
|---|---|---|---|---|

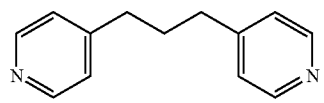

2a

[3a•(NO$_3$)$_x$]

10   37° C.   n.d.   n.d.

TABLE 5-continued

Representative oligocations and half lives ($t_{1/2}$) of C-N bond fragmentation in aqueous buffer (pH 7).

| Nucleophilic Monomer [Polymer] | n[a] | T[b] | $t_{1/2}$ | $t_{1/2}$ of Small Molecule Analogue |
|---|---|---|---|---|
| | | 50° C. | n.d. | n.d. |
| 2c [3c•(NO₃)ₓ] | 10 | 37° C. | 624 h | 422 h (5c) |
| 2i [3i•(NO₃)ₓ] | 6 | 50° C. | 36 h | 19 h (5c) |
| | | 37° C. | 70 h | 127 h at 37° C. (5i) |
| 2j [3j•(OTf)ₓ] | 6 | 37° C. | 9.2 h | 5.8 h (5j) |

[a] n = average degree of polymerization.
[b] Temperature at which polymer decomposition was measured in aqueous buffer. Polymer nitrates (3a, 3c, 3i) were prepared as in Table 4, entry 3; the triflate 3j was prepared as in Table 4, entry 8.
n.d. = no decomposition observed by NMR (<5%) after 1 week at the indicated temperature.

TABLE 6

Characterization of polymer/polyplexes formed from the indicated polycations (1 mg/ml in PBS) or polycations and double-stranded plasmid DNA (pcDNA3-EGFP, 6.2 kb, 20 ng/μL) at the indicated N/P ratio. Radius and polydispersity were determined by dynamic light scattering.
"pd" = polydispersity; "n/o" = no aggregates were observed.

| Entry | Cationic Oligomer | N/P | Conditions | radius (nm) | pd (%) |
|---|---|---|---|---|---|
| 1 | 3a•(NO₃)ₙ | 2 | H₂O, RT, freshly prepared | 82 ± 2 | 19.7 |
| 2 | 3a•(NO₃)ₙ | 2 | Entry 1, heated at 37° C. for 48 h | 80 ± 3 | 16.5 |
| 3 | 3a•(NO₃)ₙ | 2 | PBS buffer, RT, freshly prepared | 147 ± 9 | 15.5 |
| 4 | 3i•(NO₃)ₙ | 2 | H₂O, RT, freshly prepared | 116 ± 6 | 30.5 |
| 5 | 3i•(NO₃)ₙ | 2 | Entry 4, heated at 37° C. for 48 h | n/o | n/o |
| 6 | 3i•(NO₃)ₙ | 2 | PBS buffer, RT, freshly prepared | 210 ± 18 | 37.8 |
| 7 | 5a•(NO₃)₂ | 150 | H₂O or PBS | n/o | n/o |
| 8 | none | — | Plasmid DNA alone | n/o | n/o |
| 9 | 3a•(NO₃)ₙ | — | PBS buffer, RT, no DNA | 31 ± 2 | 17.6 |
| 10 | 3c•(NO₃)ₙ | — | PBS buffer, RT, no DNA | 56 ± 4 | 21.4 |
| 11 | 3i•(NO₃)ₙ | — | PBS buffer, RT, no DNA | 49 ± 3 | 12.4 |
| 12 | 3i•(NO₃)ₙ | — | Entry 11, heated at 50° C. for 4 h | n/o | n/o |

Binding and Transfection of DNA and siRNA

Figure 15A:
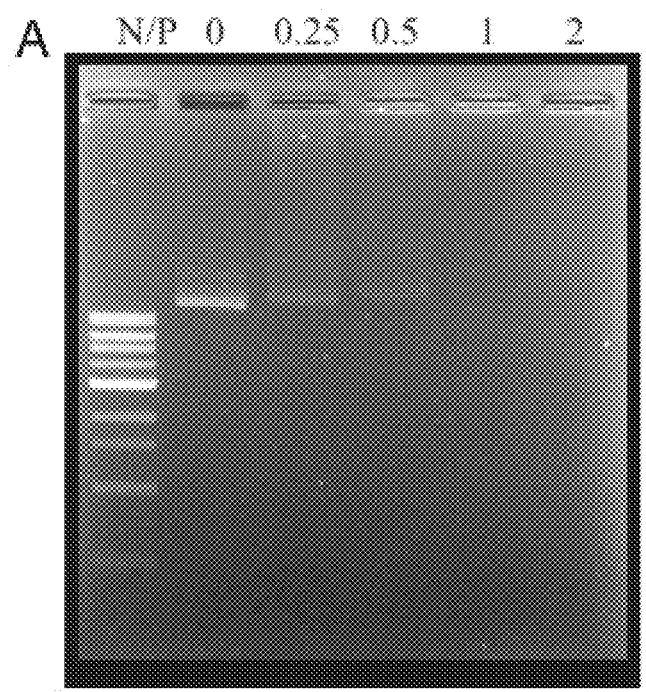
Figure 15B:
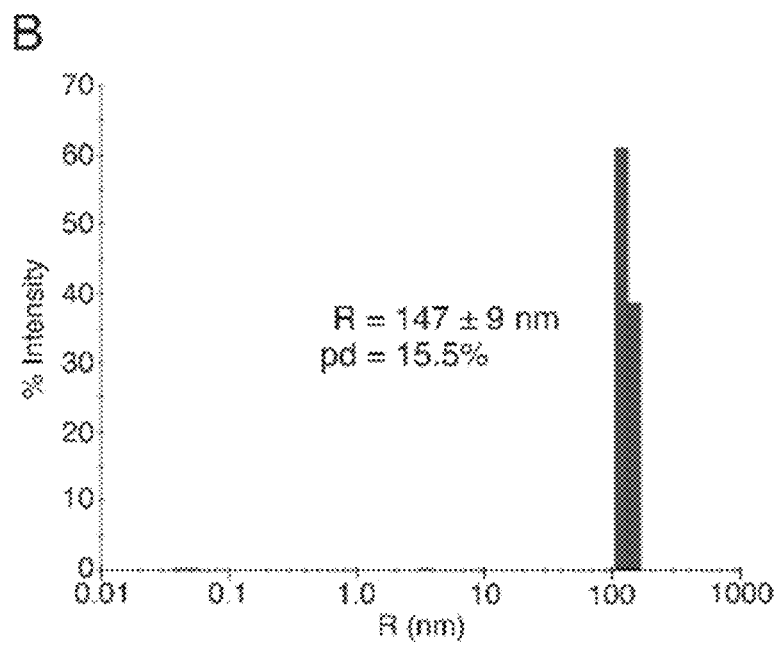
FIG. 15B shows the results of dynamic light scattering of a PBS buffer solution containing plasmid DNA mixed with polycation 3a at an N/P ratio of 2/1.

Binding of WCL oligocations to DNA was examined by agarose gel shift assay; a representative example is shown in FIG. 15A. Polyplex formation at a level sufficient to completely inhibit the electrophoretic migration of a 6.2-kb double-stranded plasmid was observed with polymer 3a at a low N/P ratio of approximately 1.0. A similar result was observed for 3i, but polymer 3c was less efficient, showing significant but incomplete retardation of electrophoresis at N/P=50. Dynamic light scattering analysis showed the resulting polyplexes to be of reasonable size and narrow size distribution (Table 6), with larger structures formed in PBS buffer vs. water. The presence of small-molecule adduct 5a in large excess had no effect on the electrophoresis of DNA nor was an observable polyplex formed. The polyplex formed with 3a resisted heating at 37° C. for 48 hours, whereas particles formed with 3i were decomposed after 24 hours of such treatment (Table 6, entries 2,5), corresponding to the fragmentation stabilities observed for the polycations alone (Table 5).

The efficiency of both stable and fragmentable oligomers for the transfection of siRNA into HeLa cells was surveyed as shown in FIGS. 16A-16B. Much higher N/P ratios were required for siRNA transfection than for DNA complexation, and were constrained by the cytotoxicity of these new materials.

Figure 11A:
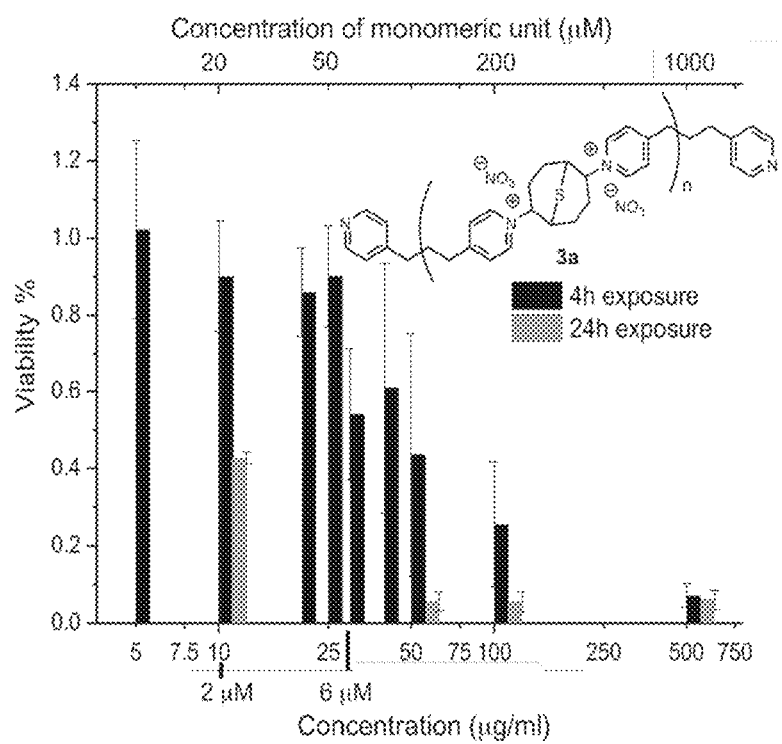
FIG. 11A is a plot of cytotoxicity tests of polymer 3a towards CHO-K1. Cell viability was measured after 4 h (black bars) or 24 h (red bars) treatment at the indicated concentration.
Figure 11B:
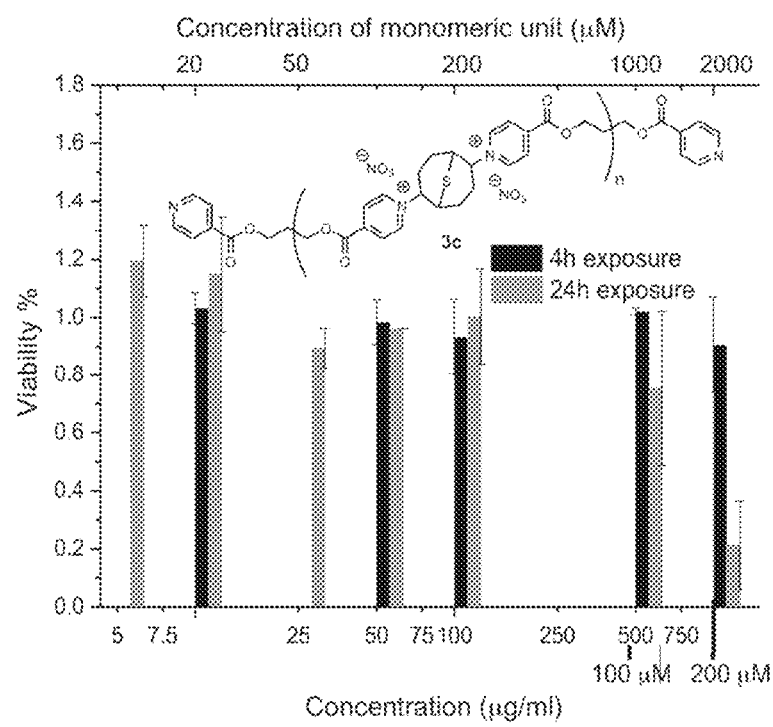
FIG. 11B is a plot of cytotoxicity tests of polymer 3c towards CHO-K1. Cell viability was measured after 4 h (black bars) or 24 h (red bars) treatment at the indicated concentration.
Figure 11C:
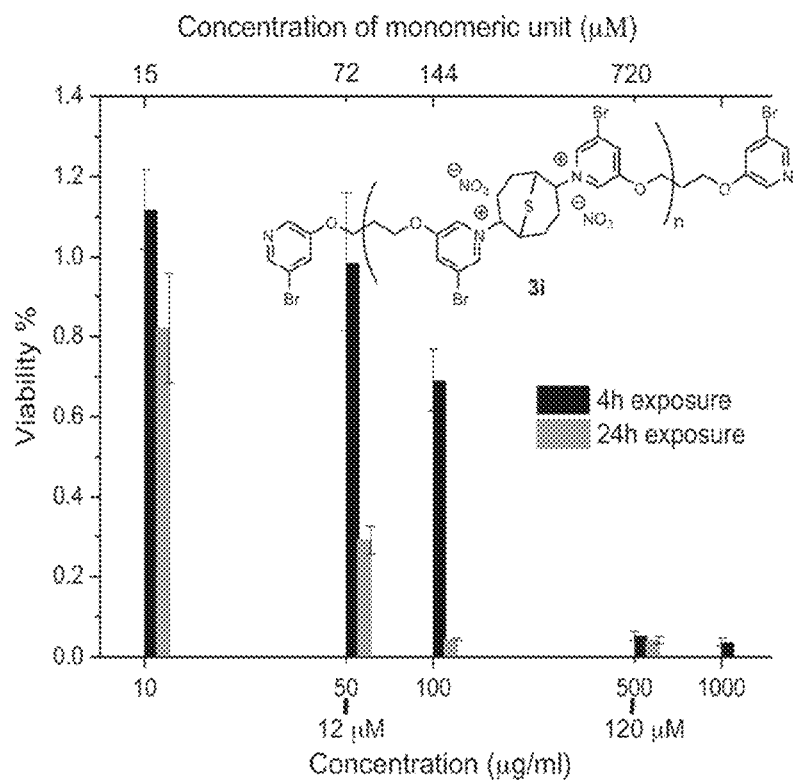
FIG. 11C is a plot of cytotoxicity tests of polymer 3i towards CHO-K1. Cell viability was measured after 4 h (black bars) or 24 h (red bars) treatment at the indicated concentration.
Figure 11D:
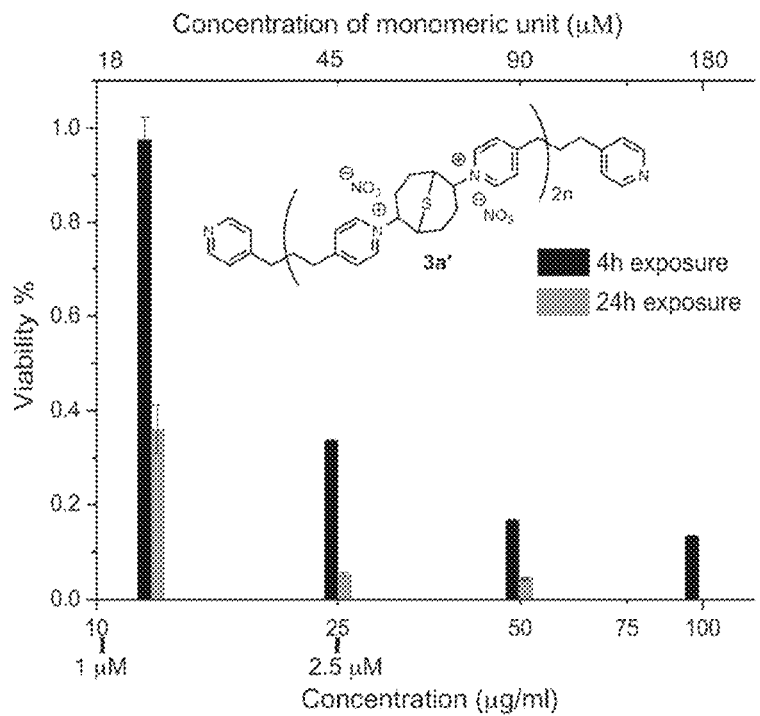
FIG. 11D is a plot of cytotoxicity tests of polymer 3a' towards CHO-K1. Cell viability was measured after 4 h (black bars) or 24 h (red bars) treatment at the indicated concentration.
Figure 12A:
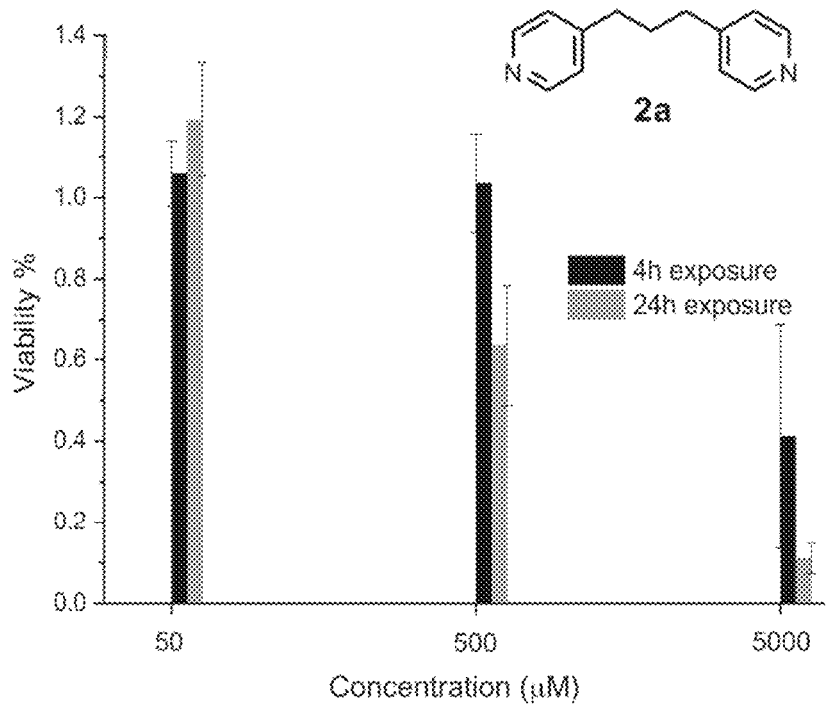
FIG. 12A is a plot of cytotoxicity tests of monomer 2a towards CHO-K1. Cell viability was measured after 4 h (black bars) or 24 h (red bars) treatment at the indicated concentration.
Figure 12B:
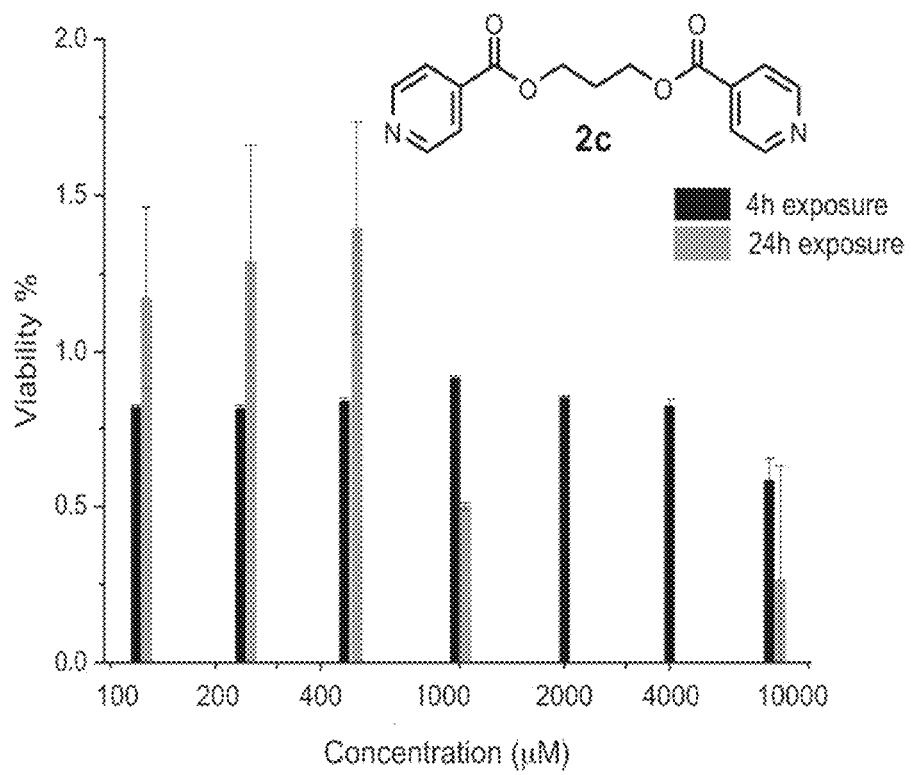
FIG. 12B is a plot of cytotoxicity tests of monomer 2c towards CHO-K1. Cell viability was measured after 4 h (black bars) or 24 h (red bars) treatment at the indicated concentration.
Figure 12C:
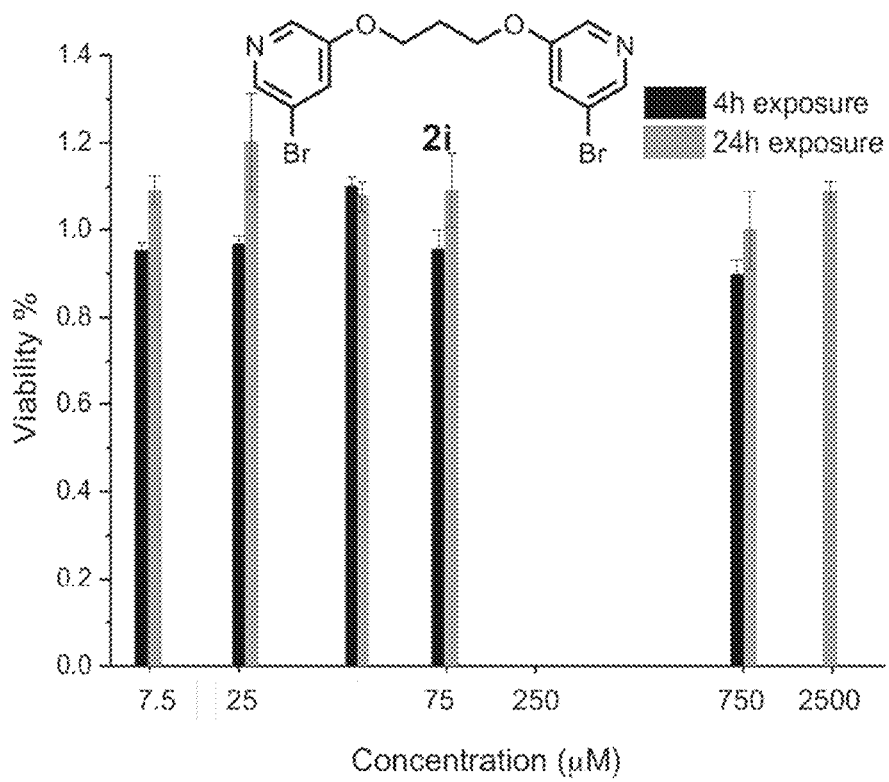
FIG. 12C is a plot of cytotoxicity tests of monomer 2i towards CHO-K1. Cell viability was measured after 4 h (black bars) or 24 h (red bars) treatment at the indicated concentration.
Figure 12D:
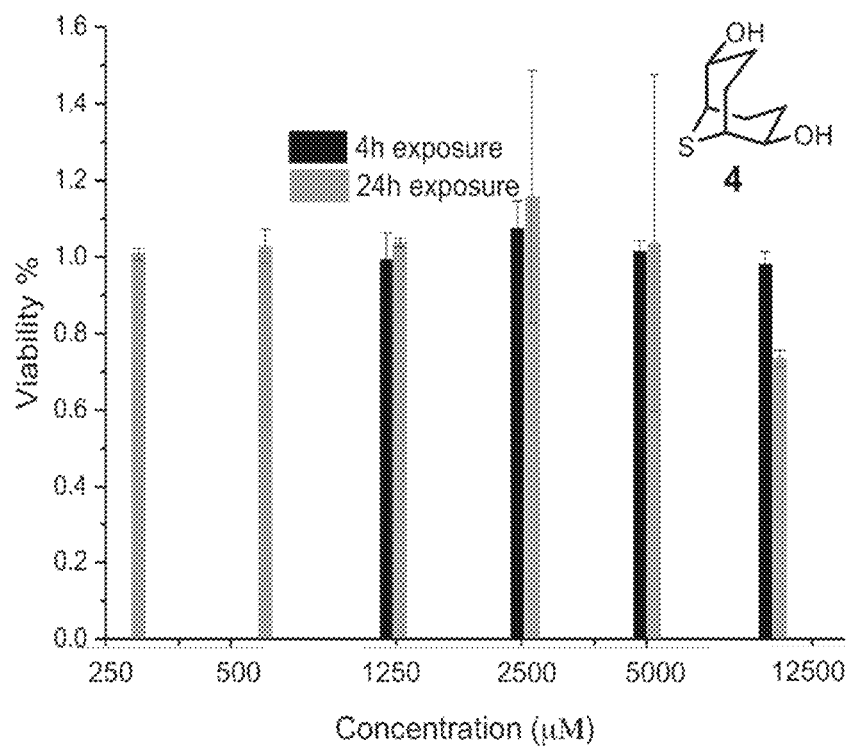
FIG. 12D is a plot of cytotoxicity tests of monomer 4 towards CHO-K1. Cell viability was measured after 4 h (black bars) or 24 h (red bars) treatment at the indicated concentration.
Figure 12E:
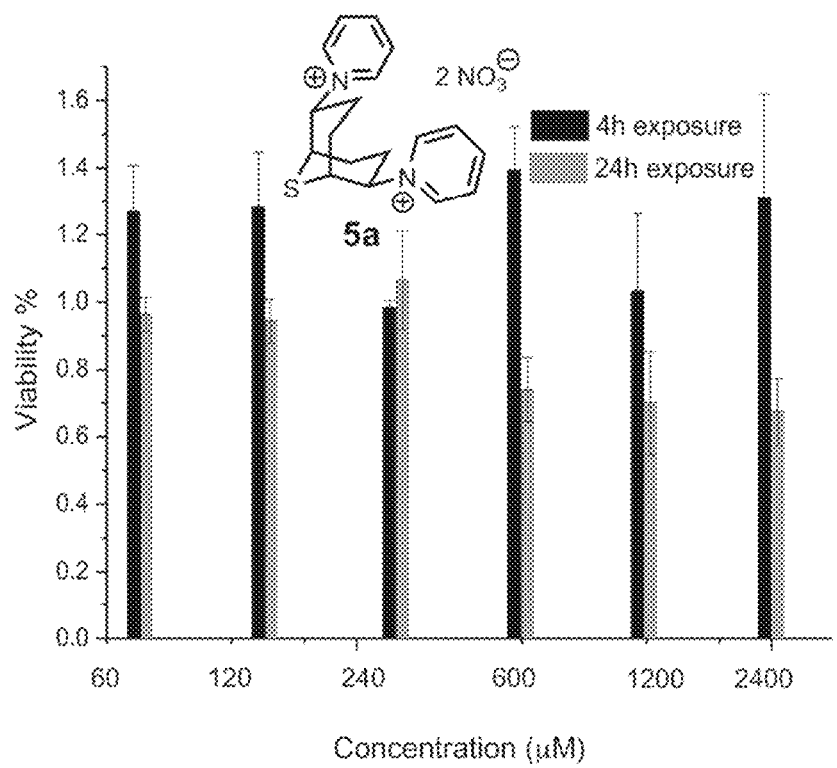
FIG. 12E is a plot of cytotoxicity tests of compound 5a towards CHO-K1. Cell viability was measured after 4 h (black bars) or 24 h (red bars) treatment at the indicated concentration.
Figure 12F:
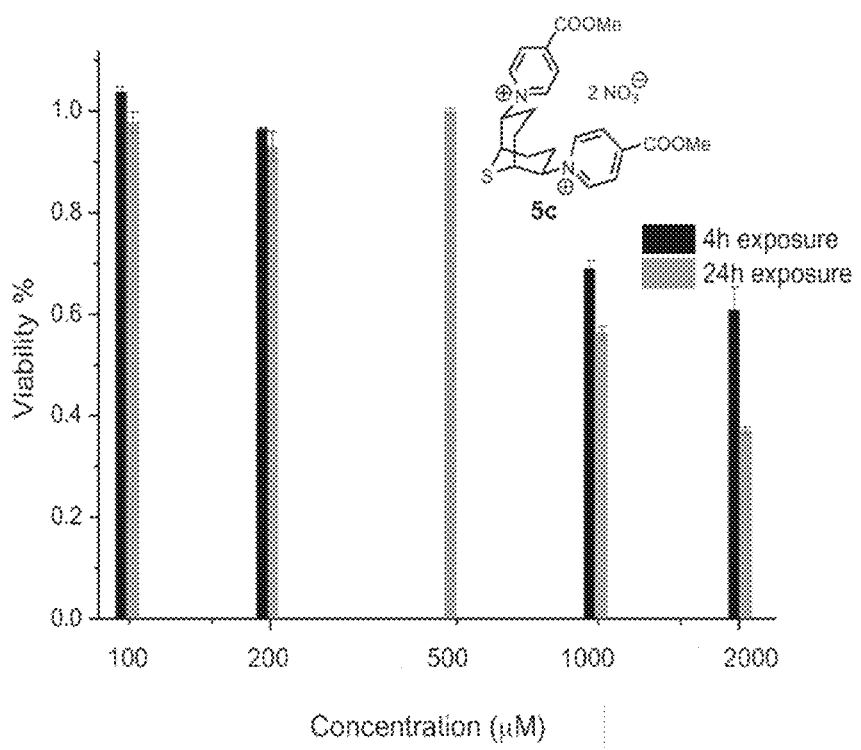
FIG. 12F is a plot of cytotoxicity tests of compound 5c towards CHO-K1. Cell viability was measured after 4 h (black bars) or 24 h (red bars) treatment at the indicated concentration.
Figure 12G:
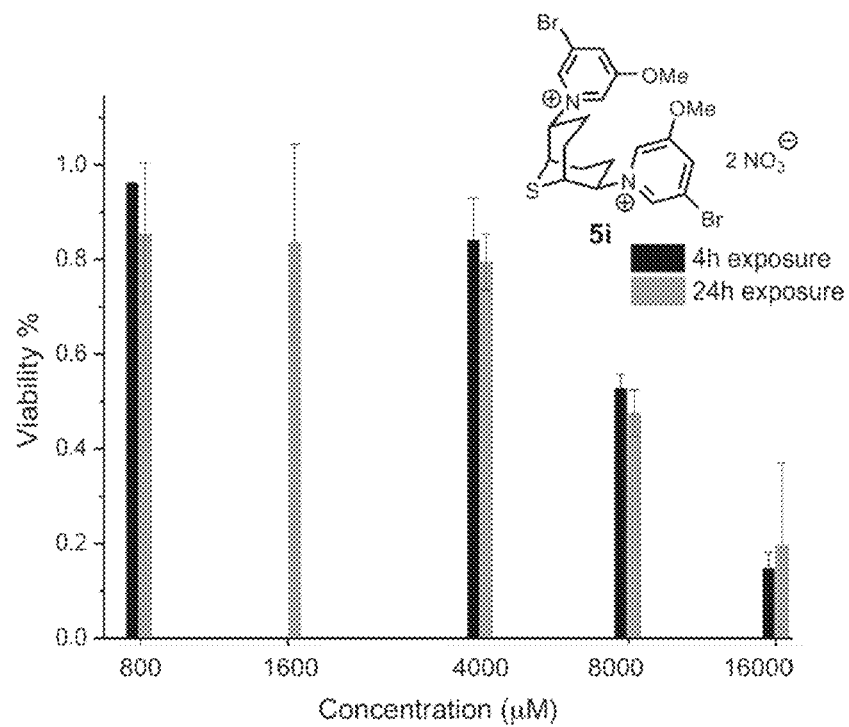
FIG. 12G is a plot of cytotoxicity tests of compound 5i towards CHO-K1. Cell viability was measured after 4 h (black bars) or 24 h (red bars) treatment at the indicated concentration.
Figure 12H:
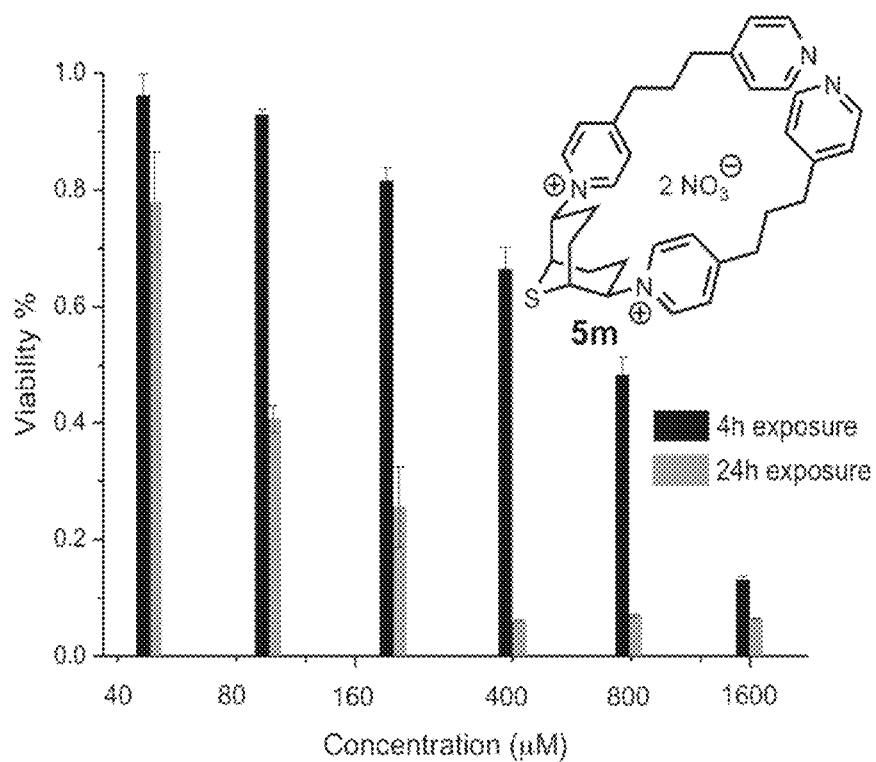
FIG. 12H is a plot of cytotoxicity tests of compound 5m towards CHO-K1. Cell viability was measured after 4 h (black bars) or 24 h (red bars) treatment at the indicated concentration.

As shown in FIGS. 11A-11C, polymers 3a, 3c, and 3i engendered significant toxicity after 24 hours exposure at 2 μM, 200 μM and 12 μM respectively (concentrations refer to that of the chains, not the monomeric units, calculated based on average molecular weights established by NMR); toxicities were much lower for 4 h exposure. The milder toxicity of 3c could be due to ester cleavage in the cell or culture media. Polymers 3a and 3c should not fragment significantly by anchimeric substitution during 24 h incubation at 37° C.; 3i may experience significant fragmentation over that time, since C—N bond breakage should occur to approximately 21% after 24 h. In any event, the dipyridine monomers from which these polymers are constructed (2a, 2c, and 2i) were found to be nontoxic at concentrations below 500 μM, and the other decomposition product (diol 4) had no effect on cellular viability up to 1 mM. Interestingly, the dicationic monomeric adducts 5a, 5c, and 5i were much less toxic than their corresponding polymers (no effect up to 500 μM or greater), and a longer polymer (3a', approximately 18 repeat units; Table 4, entry 7) was significantly more toxic than 3a (approximately 10 repeat units) at 4 h exposure. These observations suggest that cytotoxicity is associated with the polymeric nature of these materials and therefore results from interactions with the cell membrane, rather than being a function of DNA alkylation.

At optimal N/P ratios of 55-65, polymer 3a was able to mediate transfection with efficiencies near that of a standard commercial reagent (Lipofectamine, RNAiMAX) with similarly modest cytotoxicity (FIG. 16A), but these materials are, as discussed above, more toxic overall toward cultured cells. Polymer 3i exhibited no separation between cellular toxicity and apparent siRNA knockdown (FIG. 16B). Preliminary show that transfection and expression of plasmid DNA in HeLa cells can also be mediated by polymer 3a.

Conclusions

A new class of fragmentable polycations has been developed through facile nucleophilic substitution of WCL scaffolds by divalent pyridines. The efficiency of this process depends on the leaving group ability of the group being substituted, consistent with rate-limiting activation of the electrophile by formation of a highly reactive episulfonium ion. Degrees of polymerization from approximately 3 to 30 were observed for these condensation polymerization processes. A range of polymer stabilities could be engineered by tuning the nucleophilicity and leaving group ability of the pyridine units, with pyridine basicity serving as a reasonably good guide to these properties. The resulting polymers were highly efficient in complexing DNA and showed functional behavior (transfection and cytotoxicity) associated with some other classes of polycationic materials.

Example 2: Preparation of Polycations Bearing Cationic Side Chains Formed by the Condensation of 9-azabicyclo[3.3.1]nonyl Electrophiles with Nucleophiles Polycationic polymers bearing cationic side chains formed by the condensation of a 9-azabicyclo[3.3.1]nonyl electrophile with nucleophiles were prepared using the synthetic methodology outlined in Schemes 2 and 3.

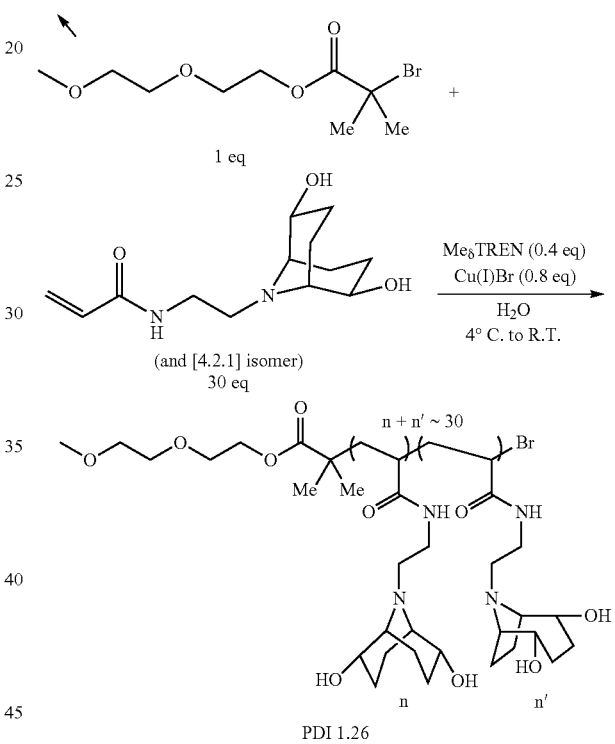

Scheme 2. Synthetic methodology used to prepare precursor polymers bearing 9-azabicyclo[3.3.1]nonyl diol sidechains.

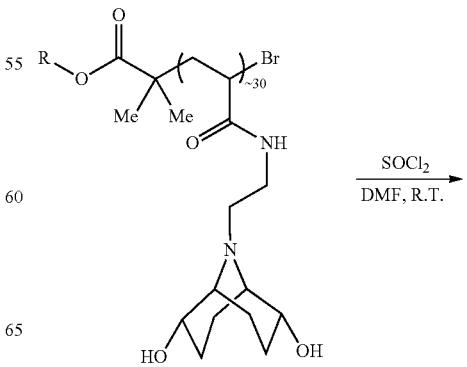

Scheme 3. Preparation polycationic polymers from precursor polymers bearing 9-azabicyclo[3.3.1]nonyl diol sidechains.

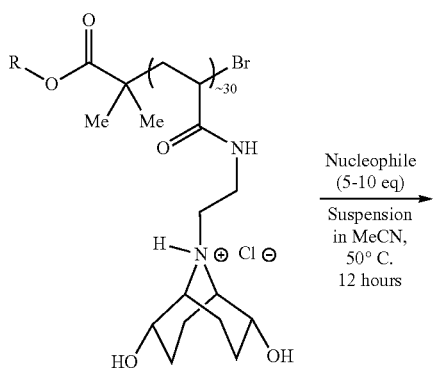
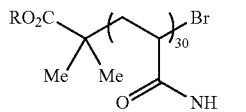
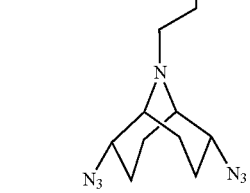
Using the synthetic methodology detailed in schemes 2 and 3, the polymers below were successfully prepared.
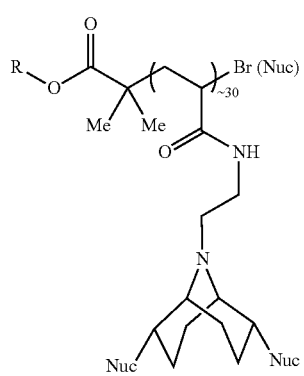
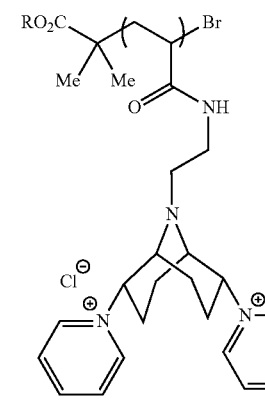
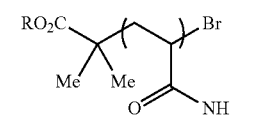
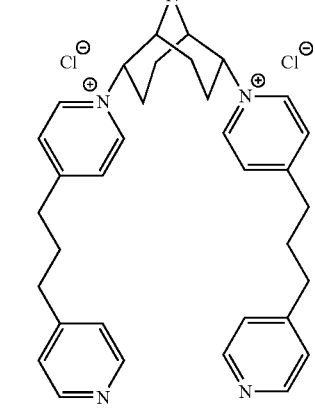
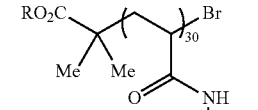
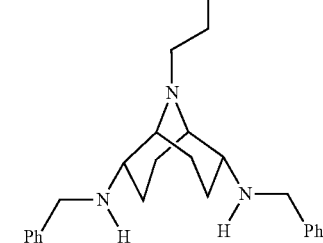

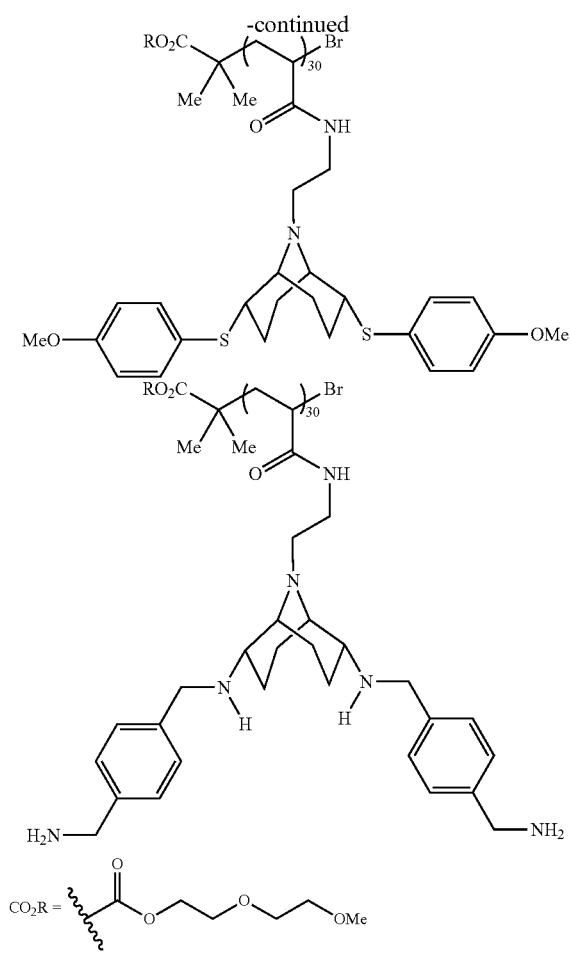

Example 3: Cytotoxicity Activity of Polycationic Materials

As detailed in Example 1, condensation of 9-thia/aza/selenabicyclo[3.3.1]nonyl electrophiles with polynucleophiles, with each bond-forming event creating a positively charged center, provides access to a wide range of polycationic materials. These materials are subject to fragmentation by the reverse process, in which the internal nucleophile ejects a heterocyclic nucleophile as a leaving group. In the case of pyridines, fragmentation rates can be efficiently tuned from hours to years at 37° C.

The cytotoxic function of these polycations was evaluated by two methods:

Method A

Bacteria suspensions (*E. coli* and *B. subtilis* ATCC 8037) were grown in Mueller-Hinton Broth (MHB) overnight at 37° C. The resulting culture was used to inoculate a second culture in 2 mL of MHB medium until an optical density of 0.8 at 600 nm was reached. The suspension was diluted with fresh MHB to an optical density of 0.001 (approximately) at 600 nm ($OD_{600}$). This suspension was mixed with different concentrations of freshly prepared polymer solutions in TRIS saline (pH 7.0) in a 96-well plate, and incubated overnight at 37° C. The $OD_{600}$ was measured for bacteria suspensions that were incubated in the presence of polymer solution or only buffer solutions as controls. Antibacterial activity was expressed as minimal inhibitory concentration (MIC), the concentration at which more than 90% inhibition of growth was observed. All experiments were run in triplicate.

Method B

The bacteria were collected by centrifugation at 4,000×g for 3 min at 4° C., washed with sterile PBS (pH 7.4) and finally suspended in PBS to get a final concentration of $6\times10^6$ cells $mL^{-1}$. The polymer solution was added into the bacteria suspension and shaken for 0.5-4 hours. Then 25 µL of suspension was spread onto a sterile Petri dishes covered with a layer of LB medium containing 0.8% agar (previously autoclaved, and cooled to 37° C.). After overnight incubation at 37° C., bacterial colonies became visible and were counted and compared with the untreated bacteria plate. The MIC was defined as the minimum concentration in the diluted series when the CFU number on the agar plate reached no more than 10% of the control plate.

Figure 16:
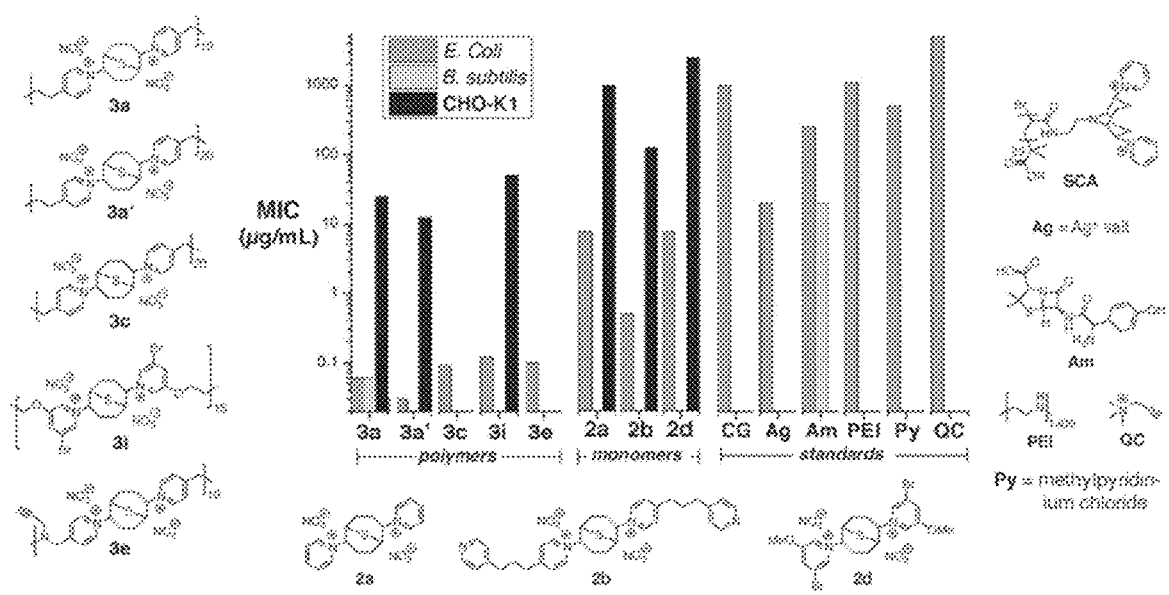
FIG. 16 is an assessment of the cytotoxic activity of example polycations (MIC=minimum concentration required to inhibit the growth of 90% of cells in a standard starting culture). Cytotoxicity was evaluated against *B. subtilis* (a representative Gram-positive strain), *E. Coli* (a representative Gram-negative strain), and CHO-K1 (a representative mammalian cell). Certain commercially-available antibacterial agents (e.g., amoxicillin) are shown for reference. Initial studies suggest that the polycations can exhibit broadspectrum activity against bacteria with a large therapeutic window.

As shown in FIG. 16, the polycations exhibited extraordinary cytotoxic activity, with *E. coli* MIC values for the polymers in solution at or below 0.1 µg/mL. These polycations are more than two orders of magnitude more potent than standard antibacterial polymers or compounds. Measurements conducted against Gram-positive *B. subtilis* gave similar results. Polycations employing the same type of positive charge carrier arranged on the side chains of acrylate monomers (as opposed to within the polymer backbone) were much less active, even though the charge density per molecular weight is nearly identical. Furthermore, the polycations were less toxic toward a representative mammalian cell line by 100-fold or more.

Members of this class are also efficient at binding polynucleotides, forming discrete polyplexes at 1:1 positive: negative charge ratios, which are far lower than most polycationic transfection agents. Monomeric adducts analogous to some of the active polymers were also toxic, but significantly less so.

Example 4: Covalent Attachment of Polycations to Glass Substrates

Figure 20:
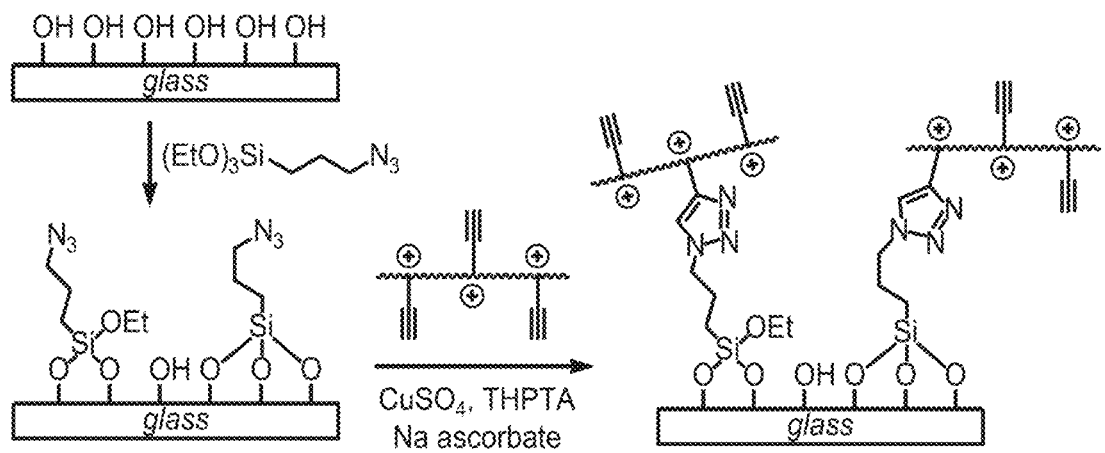
FIG. 20 is a schematic illustration of the strategy used to immobilize the polycations on a glass substrate.

Remarkable levels of bacterial cytotoxicity were also observed when the polycations described above were covalently attached to the surface of substrates. In this example, the polycations were covalently attached to a glass substrate. The strategy used to immobilize the polycations on a glass substrate are schematically illustrated in FIG. 20.

To facilitate covalent attachment to the glass substrate, polycations bearing alkynyl moieties were prepared. These polycations could then participate in click reactions with azide moieties introduced onto the glass substrate, thereby covalently bonding the polycation to the glass substrate. Polycations bearing alkynyl moieties were prepare using the synthetic methodology outlined in Scheme 4 below.

Scheme 4. Synthetic methodology used
to prepare precursor polymers
bearing 9-azabicyclo[3.3.1]nonyl diol sidechains.

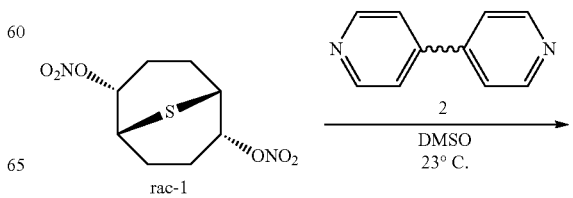

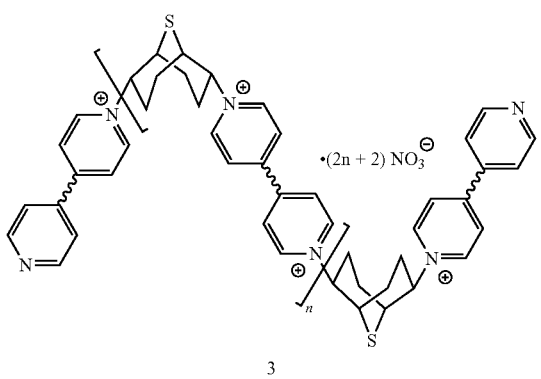

3

Briefly, the cyclic bis-electrophile 1 (21 mg, 0.1 mmol, 1 equiv), silver nitrate (34 mg, 0.2 mmol, 2 equiv) and a bispyridine dinucleophile of interest (0.1 mmol, 1 equiv) were mixed in 0.5 mL DMSO and stirred overnight at room temperature under inert atmosphere. After centrifugation, any solid material was filtered out and the resulting solution was added to 15 mL $CH_2Cl_2$ or toluene to precipitate the desired product. The material was isolated by filtration, washed with $CH_2Cl_2$ and dried to give a yellow sticky solid. The structure of polycations bearing alkynyl moieties prepared using this methodology, along with preliminary characterization data, are included in Table 7.

TABLE 7

Examples of polycations bearing alkynyl moieties prepared using the methodology outlined in Scheme 2 (but with varying nucleophilic monomers.

| nucleophile monomer | Polymer | $n^a$ | Mn (Da) | $R_h^b$ (nm) |
|---|---|---|---|---|
| 2b | 3b | 12 | 6200 | 77 |
| 2c | 3c | 8 | 5800 | — |
| 2d | 3d | 10 | 5500 | 35 |
| | 3i | 18 | 8800 | 151 |

TABLE 7-continued

Examples of polycations bearing alkynyl moieties prepared using the methodology outlined in Scheme 2 (but with varying nucleophilic monomers.

| nucleophile monomer | Polymer | $n^a$ | Mn (Da) | $R_h^b$ (nm) |
|---|---|---|---|---|
| 2a (1 equiv) 2b (9 equiv) | 3k | 18 | 8400 | — |
| 2a (6 equiv) 2b (4 equiv) | 3l | 18 | 8600 | — |

One prepared, the polycations were covalently attached to the surface of glass cover slips using the procedures detailed below. First, the glass cover slips were rendered amenable to click chemistry modification by initial attachment of azide groups via standard siloxide coating methods. Briefly, 1 cm×1 cm silicon or glass chips or glass beads were cleaned with piranha solution for 30 min, sonicated with deionized water for another 30 min, rinsed with methanol and dried with $N_2$. The resulting clean substrate was immersed in a solution of (3-azidopropyl) triethoxysilane in toluene (20 mM) for 12 hours. The glass or silicon substrate was removed from the reaction mixture, washed with methanol, and dried.

Subsequently, the azide-functionalized slips were reacted with a polycation bearing alkyne groups in a Cu(I)-catalyzed azide-alkyne cycloaddition (CuAAC) reaction. Briefly, the azide-functionalized glass was immersed in a solution of the polycation of interest (1 mg/mL in 80/20 water/t-BuOH mixture) containing copper sulfate (5% equivalents with respect to alkyne), sodium ascorbate (10 mM) and THPTA ligand (1 equivalent with respect to Cu) for 12 hours. After the reaction solution was away from the material, the surface was further cleaned by immersion in a 1 mM solution of cysteine to remove metal ions that may be bound to the surface, followed by washing with methanol and drying.

The cytotoxicity of the polycations deposited on the glass cover slips was then evaluated. Briefly, the bacteria were collected by centrifugation at 4,000×g for 3 min at 4° C., washed with sterile PBS (pH 7.4) and finally suspended in PBS to get a final concentration of $6×10^6$ cells $mL^{-1}$. The glass/silicon substrate (0.01-0.04 $cm^2$ in area) was added into the bacteria suspension and shaked for 0.5-4 hours. Then 25 ul of suspension was spread onto a sterile Petri dishes covered with a layer of LB medium containing 0.8% agar (previously autoclaved, and cooled to 37° C.). After overnight incubation at 37° C., bacterial colonies became visible and were counted and compared with the untreated bacteria plate. The MIC was defined as the minimum concentration in the diluted series when the CFU number on the agar plate reached no more than 10% of the control plate.

Figure 17:
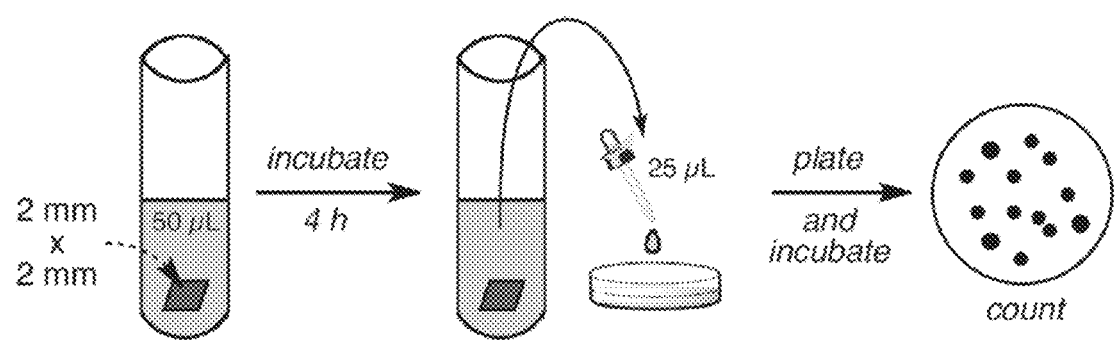
FIG. 17 is a schematic illustration of the methods used to assess the cytotoxicity of glass substrates covalently functionalized with example polycations.

The results are shown in FIG. 17. Polycation-functionalized glass cover slips, approximately 0.01 cm$^2$ in area, were found to abolish (*E. coli*) or significantly inhibit (*P. aeruginosa*) the ability of bacteria to grow on agar plates after exposure. If dispersed in solution, the overall concentration of the polycations would have been approximately 0.01-0.3 µg/mL.).

As a control, azide-functionalized glass cover slips were similarly reacted with a small quaternary alkyne (N,N,N-trimethylprop-2-yn-1-ammonium bromide). These control slips were not effective at reducing bacterial growth, demonstrating that that cytotoxicity resulted from the attached polycationic polymer.

To confirm that cytotoxicity did not result from leaching of the polycation into the culture, the polycation-functionalized glass cover slip was vigorously washed before being immersed in the bacterial culture. The pre-washed polycation-functionalized glass cover slip still deactivated the bacterial culture, suggesting that leaching is not a major component of cytotoxic activity.

Example 5. Covalent Attachment of Polycations to Polyvinyl Chloride (PVC) Substrates Numerous conditions, including ventilator-associated pneumonia and catheter-related urinary tract infections, are linked to the formation of biofilms and colonization of bacteria on medical tubing, which then leads to a bacterial infection. These conditions are associated with high mortality rates, as well as increased hospital stay lengths and medical care costs. Currently, using silver-coated tubing is the main effort to minimize these infections in intubated patients, however, this is not FDA approved for pediatric use.

Figure 18:
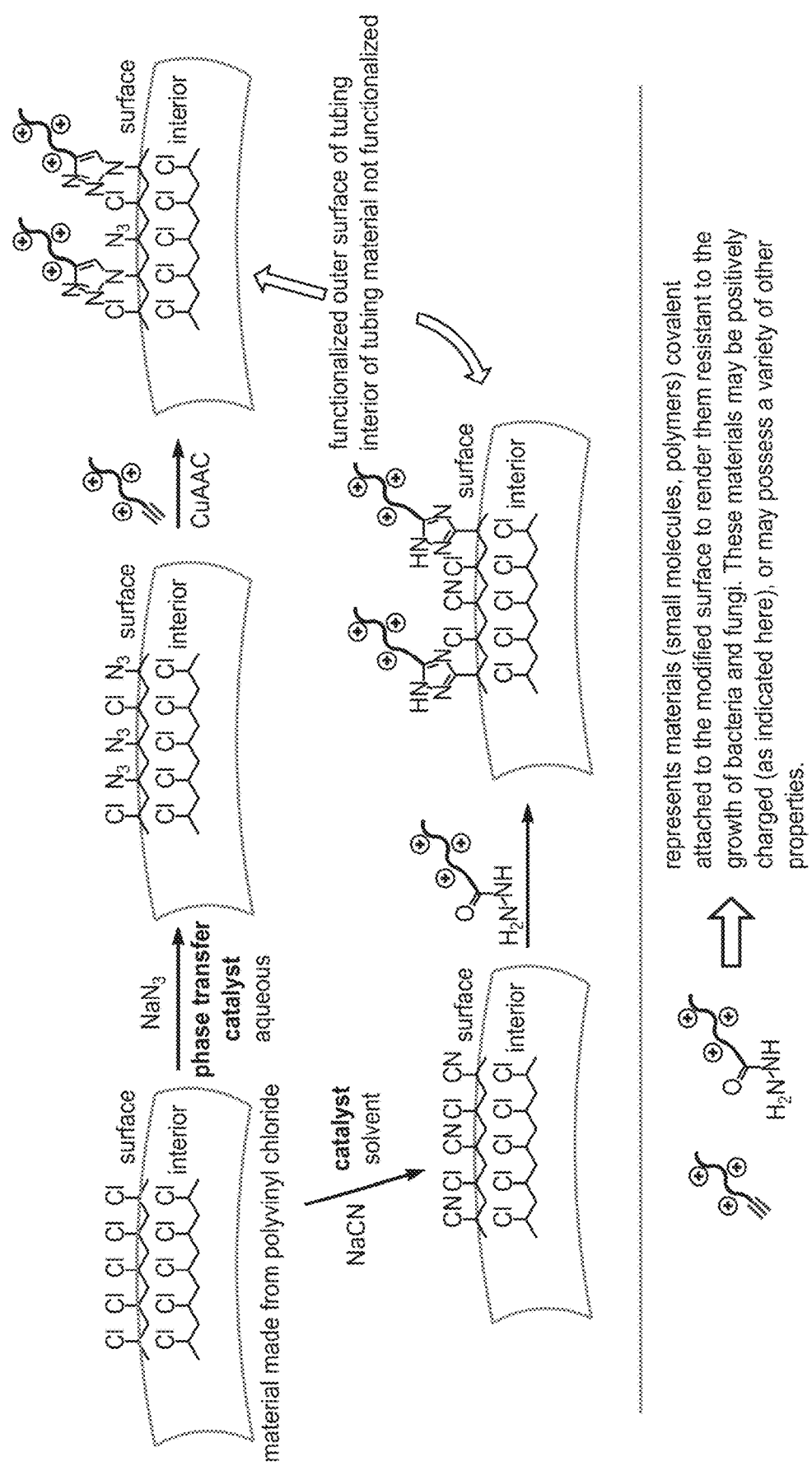
FIG. 18 is a schematic illustration of methods for covalently functionalizing polyvinyl chloride (e.g., medical tubing) to improve resistance to bacterial and fungal colonization and biofilm formation.

To address these needs, the covalent linkage of anti-microbial agents to existing medical tubing to reduce/eliminate the growth of pathogenic bacteria was investigated. Covidien Mallinckrodt cuffless endotracheal tubing (4.00 mm ID; PVC) was used as a substrate for proof of principle studies. Anti-microbial agents were covalently attached to the surface of the medical tubing. The functionalized materials was then be tested for bacterial adhesion using hospital-relevant strains: *P. aeruginosa*, *S. aureus*, *E. coli*. In this way, different modifications of the substrate could be screened in a time-efficient manner to develop alternative strategies for minimizing biofilm and colonization of bacteria and fungi on medical tubing. These strategies are schematically illustrated in FIG. 18.

In a first example, the PVC of an example segment of medical tubing was functionalized with example polycations using a CuAAC) reaction. In the first step, one or more PVC surfaces of the medical tubing (the interior surface, the exterior surface, or both the interior surface and the exterior surface) were derivatized with azide. Subsequently, the azides on the derivatized PVC were reacted with alkynes present in the polycationic polymer in an azide-alkyne cycloaddition reaction to covalently attach the polycationic polymer to the PVC surface.

Figure 21:
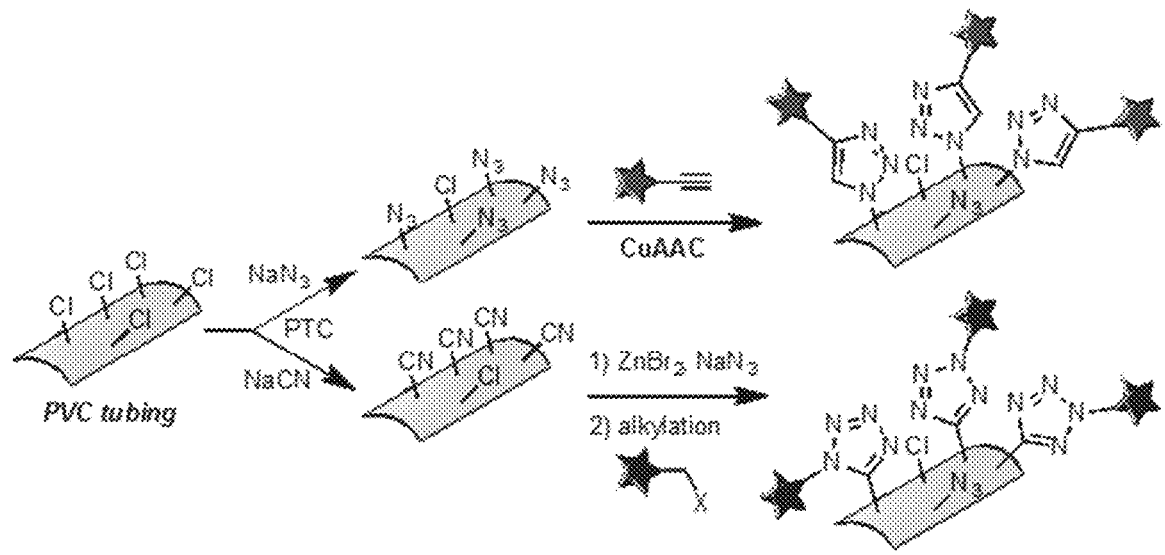
FIG. 21 is a schematic illustration of the strategy used to immobilize the polycations on a PVC substrate.

Strategies used to immobilize the polycations described herein on a PVC substrate (in this case PVC tubing) are outlined in FIG. 21.

In order to introduce azide moieties onto the surface of the PVC, a phase-transfer catalyst was used to facilitate the substitution reaction of chloride for azide on the solvent-exposed surface. Briefly, initial studies were performed using commercial plain endotracheal tubing (ET) (Covidien Mallinckrodt Oral/Nasal Tracheal Tube Cuffless, 4.0 mm inner diameter, 5.6 mm outer diameter) and catheter tubing (CT) (GentleCath Intermittent Urinary Catheter, Size 14 Male Nelaton 16") purchased from the indicated vendors. Test reactions were performed as follows.

Small small pieces of clear, cut tubing (approximately 0.5×0.5 cm) were placed in 4 mL of an aqueous solution of 450 mM NaN$_3$ and 9 mM phase transfer catalyst in sealed vials. Each mixture was heated to 60° C., 80° C., or 100° C. for periods from 12 to 48 hours while being shaken vigorously on an orbital shaker. The samples were then placed in water and sonicated for 1 hour to rinse, changing the water at 30 minutes, and then dried in an oven at 60° C. for 4-8 hours. Using this methodology, the amount of azide introduced onto the surface of the PVC tubing could be readily controlled without leaching plasticizers or changing the bulk mechanical properties of the PVC.

Figure 19:
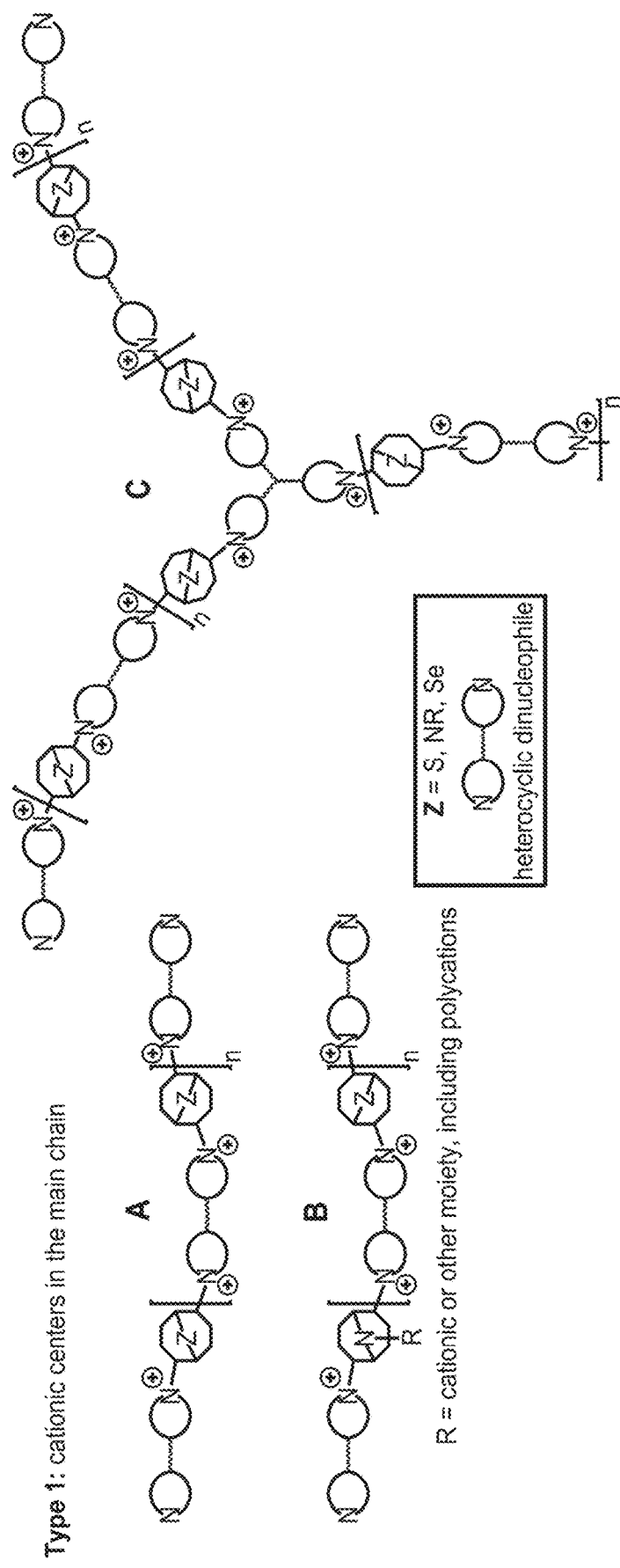
FIG. 19 is a schematic illustrated of classes of polycationic materials based on the reaction of a 9-thia/aza/selenabicyclo[3.3.1]nonyl electrophile with a nucleophile.
Figure 19:
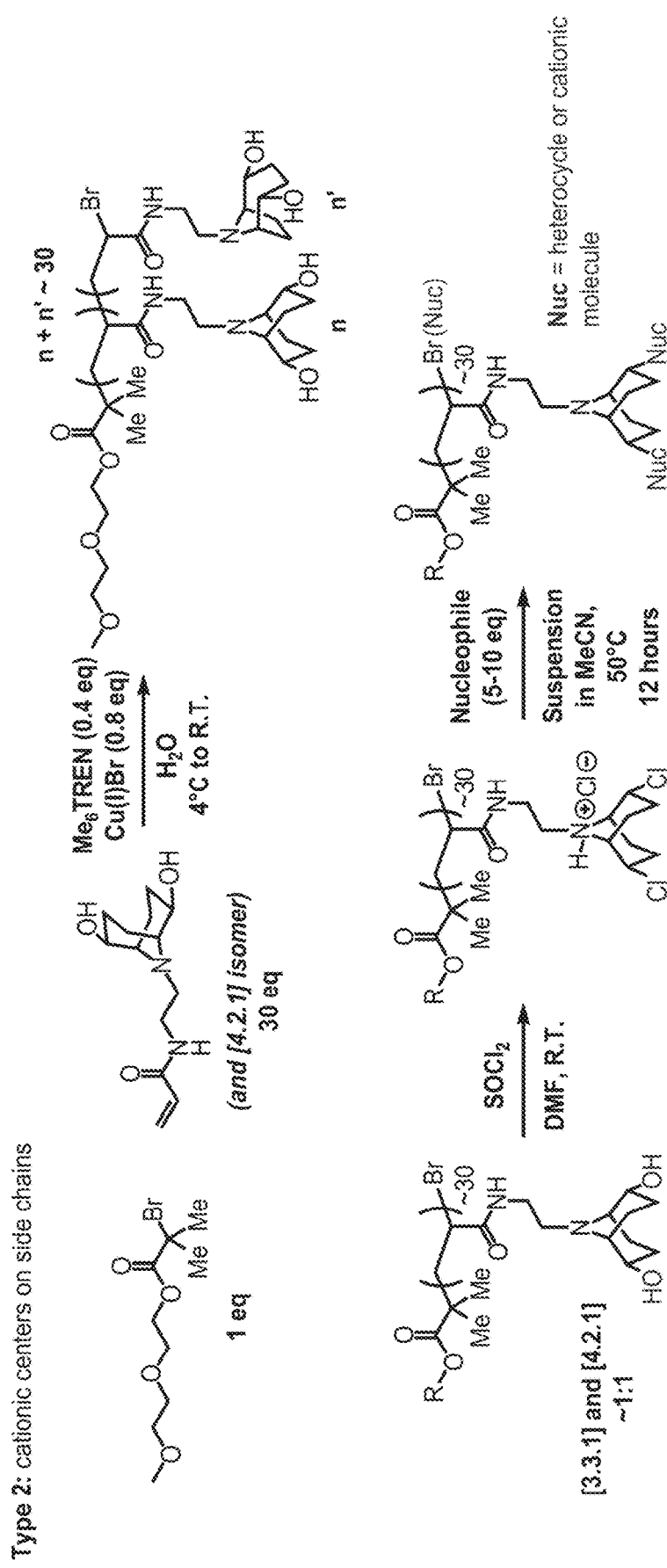

Subsequently, anti-bacterial and anti-fungal molecules were covalently attached to the PVC. In these proof of principle studies, polycationic polymers based on cationic centers formed by the reaction of a 9-thia/aza/selenabicyclo[3.3.1]nonyl electrophile with a nucleophile. Each bond-forming event generates a positive charge. FIG. 19 illustrates examples of polycationic polymers that can be prepared through the reaction of a 9-thia/aza/selenabicyclo[3.3.1]nonyl electrophile with a nucleophile. Type I materials are prepared through the condensation of 9-thia/aza/selenabicyclo[3.3.1]nonyl dielectrophiles with polynucleophiles (e.g., dinucleophiles). Each bond-forming event in this condensation polymerization process generates a positively charged center within the polymer backbone. Type II materials contain cationic sidechains. Type II materials can be formed, for example, by polymerization of monomers (e.g., acrylate monomers) containing pendant 9-azabicyclo[3.3.1]nonyl electrophiles. Following polymerization, the pendant 9-azabicyclo[3.3.1]nonyl electrophiles can be reacted with nucleophiles to introduce positively charged centers within the polymer sidechains. If desired, conventional anti-microbial compounds (e.g., antibiotics) can be used in place of (or in addition to) these polycationic polymers.

In a second example, the PVC was derivatized with alternative functional groups (other than azides) that could subsequently be reacted with anti-bacterial and/or anti-fungal molecules. Other moieties that can serve as reactive functional groups to facilitate surface functionalization include, for example, thiolate, thiocyanate (SCN$^-$), hydroxide, iodide, and nitrile groups. In a second example, the PVC was cyano-functionalized. Briefly, small pieces of clear, cut tubing (approximately 0.5×0.5 cm) were placed in 4 mL of an aqueous solution of 450 mM NaCN and 9 mM phase transfer catalyst in sealed vials. Each mixture was heated to 60° C., 80° C., or 100° C. for periods from 12 to 48 hours while being shaken vigorously on an orbital shaker. The samples were then placed in water and sonicated for 1 hour to rinse, changing the water at 30 minutes, and then dried in an oven at 60° C. for 4-8 hours.

Subsequently, the nitrile groups on the derivatized PVC were reacted sodium azide to produce 1H-tetrazoles. Briefly, the cyanated PVC samples were immersed in an aqueous solution of sodium azide (485 mM) zinc bromide (440 mM) at 100° C. for 72 h to form 5-substituted 1H-tetrazoles on the material surface. These surfaces were then alkylated with an antimicrobial compound or with a compound containing an azide or alkyne group to which subsequent connection can be made by azide-alkyne cycloaddition. By way of example, the samples were further immersed in a solution of 360 mM potassium carbonate and 48 mM of the electrophile 2,3,4, 5,6-pentafluorobenzyl bromide, and shaken at 80° C. for 12 hours. Alternatively, nitrile groups on the derivatized PVC could be reacted with polycationic polymers bearing hydrazone moieties (which condense with the nitrile groups to form 1,2,4-triazoles).

The compositions, devices, systems, and methods of the appended claims are not limited in scope by the specific compositions, devices, systems, and methods described herein, which are intended as illustrations of a few aspects of the claims. Any compositions, devices, systems, and methods that are functionally equivalent are intended to fall within the scope of the claims. Various modifications of the compositions, devices, systems, and methods in addition to those shown and described herein are intended to fall within the scope of the appended claims. Further, while only certain representative compositions, devices, systems, and method steps disclosed herein are specifically described, other combinations of the compositions, devices, systems, and method steps also are intended to fall within the scope of the appended claims, even if not specifically recited. Thus, a combination of steps, elements, components, or constituents may be explicitly mentioned herein or less, however, other combinations of steps, elements, components, and constituents are included, even though not explicitly stated.

The term "comprising" and variations thereof as used herein is used synonymously with the term "including" and variations thereof and are open, non-limiting terms. Although the terms "comprising" and "including" have been used herein to describe various embodiments, the terms "consisting essentially of" and "consisting of" can be used in place of "comprising" and "including" to provide for more specific embodiments of the invention and are also disclosed. Other than where noted, all numbers expressing geometries, dimensions, and so forth used in the specification and claims are to be understood at the very least, and not as an attempt to limit the application of the doctrine of equivalents to the scope of the claims, to be construed in light of the number of significant digits and ordinary rounding approaches.

Unless defined otherwise, all technical and scientific terms used herein have the same meanings as commonly understood by one of skill in the art to which the disclosed invention belongs. Publications cited herein and the materials for which they are cited are specifically incorporated by reference.

What is claimed is:

1. A polycationic polymer derived from the condensation of a cyclic bis-electrophile, a first polynucleophilic monomer, and a second polynucleophilic monomer,
wherein the cyclic bis-electrophile is defined by Formula II below

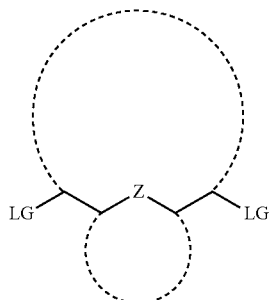

Formula II wherein
each dotted line represents a cyclic moiety;
LG represents a leaving group;
Z represents S, Se, or $NR^3$; and
$R^3$ represents alkyl, alkenyl, alkynyl, alkoxy, aryl, heteroaryl, alkylaryl, alkylheteroaryl, cycloalkyl alkylcycloalkyl, heterocycloalkyl, alkylheterocycloalkyl, peptidyl, polyamino, or polyalkyleneoxy;

wherein the first polynucleophilic monomer is defined by Formula III below

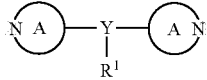

Formula III wherein
A represents a heterocyclic ring comprising a tertiary nitrogen atom;
Y is absent or represents a linking group; and
R¹ is absent, or represents halogen, hydroxy, amino, cyano, azido, hydrazone, alkyl, alkenyl, alkynyl, alkoxy, aryl, heteroaryl, alkylaryl, alkylheteroaryl, cycloalkyl alkylcycloalkyl, heterocycloalkyl, alkylheterocycloalkyl, alkylthio, alkylsulfinyl, alkylsulfonyl, alkylamino, dialkylamino, alkylcarbonyl, alkoxycarbonyl, alkylaminocarbonyl, dialkylaminocarbonyl, peptidyl, polyamino, or polyalkyleneoxy; and
wherein the second polynucleophilic monomer is defined by Formula IV below

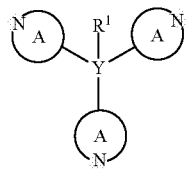

Formula IV wherein
A represents a heterocyclic ring comprising a tertiary nitrogen atom;
Y is absent or represents a linking group; and
R¹ is absent, or represents halogen, hydroxy, amino, cyano, azido, hydrazone, alkyl, alkenyl, alkynyl, alkoxy, aryl, heteroaryl, alkylaryl, alkylheteroaryl, cycloalkyl alkylcycloalkyl, heterocycloalkyl, alkylheterocycloalkyl, alkylthio, alkylsulfinyl, alkylsulfonyl, alkylamino, dialkylamino, alkylcarbonyl, alkoxycarbonyl, alkylaminocarbonyl, dialkylaminocarbonyl, peptidyl, polyamino, or polyalkyleneoxy.

2. The polycationic polymer of claim 1, wherein the cyclic bis-electrophile is defined by Formula IIA, Formula IIB, or Formula IIC below

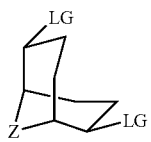

Formula IIA

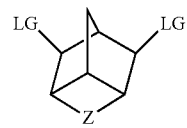

Formula IIB

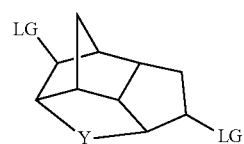

Formula IIC wherein LG and Z are as defined above with respect to Formula II.

3. A polycationic polymer comprising a recurring unit defined by Formula V below

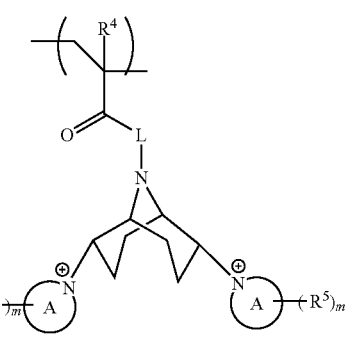

Formula V wherein
R⁴ represents H or methyl;
L is absent or represents a linking group;
A represents, individually for each occurrence, a heterocyclic ring comprising a cationic nitrogen center;
R⁵ is absent, or represents, individually for each occurrence, halogen, hydroxy, amino, cyano, azido, hydrazone, alkyl, alkenyl, alkynyl, alkoxy, aryl, heteroaryl, alkylaryl, alkylheteroaryl, cycloalkyl alkylcycloalkyl, heterocycloalkyl, alkylheterocycloalkyl, alkylthio, alkylsulfinyl, alkyl sulfonyl, alkylamino, dialkylamino, alkylcarbonyl, alkoxycarbonyl, alkylaminocarbonyl, dialkylaminocarbonyl, peptidyl, polyamino, or polyalkyleneoxy; and
m is an integer from 0 to 5.

4. The polycationic polymer of claim 3, wherein the polycationic polymer further comprises a recurring unit derived from the polymerization of one or more ethylenically-unsaturated monomers.

5. The polycationic polymer of claim 4, wherein the one or more ethylenically-unsaturated monomers are chosen from the group consisting of styrene, butadiene, meth(acrylate) monomers, vinyl acetate, vinyl ester monomers and combinations thereof.

* * * * *

SEQUENCE LISTING

<160> NUMBER OF SEQ ID NOS: 2

<210> SEQ ID NO 1
<211> LENGTH: 21
<212> TYPE: RNA
<213> ORGANISM: Artificial Sequence
<220> FEATURE:
<223> OTHER INFORMATION: Synthetic construct

<400> SEQUENCE: 1
caagcugacc cugaaguucu u                                              21

<210> SEQ ID NO 2
<211> LENGTH: 21
<212> TYPE: RNA
<213> ORGANISM: Artificial Sequence
<220> FEATURE:
<223> OTHER INFORMATION: Synthetic construct

<400> SEQUENCE: 2
gaacuucagg gucagcuugu u                                              21